United States Patent [19]

Beal, III et al.

[11] 3,984,455
[45] Oct. 5, 1976

[54] PROSTAGLANDIN E₁ ANALOGS

[75] Inventors: Philip F. Beal, III, Kalamazoo; Frank H. Lincoln, Jr., Portage; John E. Pike, Kalamazoo, all of Mich.

[73] Assignee: The Upjohn Company, Kalamazoo, Mich.

[22] Filed: Dec. 16, 1974

[21] Appl. No.: 533,302

Related U.S. Application Data

[62] Division of Ser. No. 379,475, July 16, 1973, Pat. No. 3,896,156, which is a division of Ser. No. 51,370, June 30, 1970, abandoned, which is a division of Ser. No. 809,046, March 20, 1969, Pat. No. 3,524,867, which is a division of Ser. No. 555,283, June 6, 1966, Pat. No. 3,435,053.

[52] U.S. Cl. .................. 260/468 D; 260/247.2 R; 260/268 R; 260/293.65; 260/326.2; 260/410; 260/429.9; 260/430; 260/439 R; 260/448 R; 260/488 R; 260/501.1; 260/501.1 S; 260/501.17; 260/501.2; 260/514 D
[51] Int. Cl.² ........................................ C07C 177/00
[58] Field of Search .................. 260/468 D, 514 D

[56] References Cited
OTHER PUBLICATIONS
Eliel, Stereochemistry of Carbon Compounds, pp. 49–55, (1963).

*Primary Examiner*—Robert Gerstl

[57] ABSTRACT

This invention is a group of optically active or racemic prostaglandin E₁ analogs of the formula:

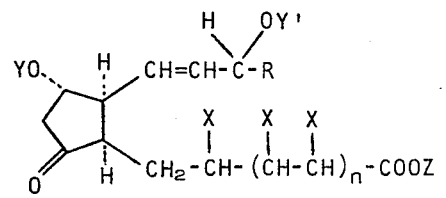

wherein R is an alkyl group containing from one to 8 carbon atoms, inclusive, X is hydrogen or methyl with the proviso that not more than one methyl group can be present in a given side chain, Y and Y' are hydrogen or alkanoyl of one to 12 carbon atoms, inclusive, Z is hydrogen, a hydrocarbyl group of one to 12 carbon atoms, inclusive, or a pharmacologically acceptable cation, and n is 0, 1 or 2. These prostaglandin E₁ analogs are useful for the same pharmacological purposes as $PGE_1$.

5 Claims, No Drawings

PROSTAGLANDIN E₁ ANALOGS

CROSS REFERENCE TO RELATED APPLICATIONS

This application is a division of copending application Ser. No. 379,475, filed July 16, 1973, now U.S. Pat. No. 3,896,156, which is a division of copending application Ser. No. 51,370, filed June 30, 1970, now abandoned, which is a division of copending application Ser. No. 809,046, filed Mar. 20, 1969, now U.S. Pat. No. 3,524,867, which is a division of copending application Ser. No. 555,283, filed June 6, 1966, now U.S. Pat. No. 3,435,053.

This invention relates to compounds related to prostaglandins and having prostaglandin-like activity, and to intermediates used in the manufacture of these compounds. This invention also relates to analogs of prostaglandin $E_1$, and a process and intermediates for their manufacture.

The term prostaglandin is used broadly to designate a material, having hypotensive and smooth muscle-stimulating activity, obtained from accessory genital glands, seminal fluid, and the like. Prostaglandins have been found to be present in the kidney of both male and female animals. A crude material, designated prostaglandin, was obtained by von Euler from extracts of such materials [Arch. Exp. Path. Pharmak. 175, 78 (1934), 181 (1936), J. Physiol, 72, 74 (1931), 81, 102 (1934), 84, 21 (1935), 88, 213 (1936), Klin. Wschr. 14, 118L (1935)]. Recently [Acta Chemica Scandinavia 14, 1693–1704 (1960)] two distinct compounds designated PGE (now known as $PGE_1$) and PGF (now known as $PGF_1$) have been isolated from crude materials such as von Euler's prostaglandin, and their structures have been determined. The structure of $PGE_1$ is:

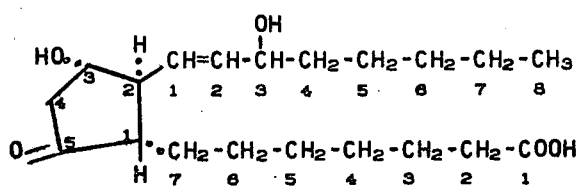

and it is named systematically (using the numbering shown) as 7-[3α-hydroxy-5-oxo-2β-(3-hydroxy-1-octenyl)-1α-yl]heptanoic acid. The dotted line attachments shown in the above formula indicate that these substituents are in the α-configuration, i.e. are below the plane of the cyclopentane nucleus. $PGF_{1\alpha}$ is the same as $PGE_1$ except that the 5-oxo group is replaced by an α-hydroxy group.

The side chain double bond in $PGE_1$ can be selectively reduced to give dihydro $PGE_1$, which exhibits prostaglandin-like activity. Similarly, $PGF_{1\alpha}$ gives the active compound dihydro $PGF_{1\alpha}$. Other chemical alterations, for example introduction of double bonds at other positions in the side chains, or in the nucleus, lead to prostaglandins having a prostaglandin-like activity, but often profoundly altered in the relative intensity of the effects in the spectrum of prostaglandin activity. The prostaglandins having a keto group at the 5-position of the nucleus are known as the PGE series; those having a 5-hydroxy group in place of the keto group are known as the PGF series.

We have discovered that prostaglandin F analogs having cis-side chains (β,β) and a keto group in place of the 3-hydroxy group in the side chain (compounds IA and IB in the flow sheet below) lose water and cyclize with unexpected ease, forming dihydropyran derivatives (compounds IIA and IIB in the flow sheet below) with a α-hydroxy group remaining. The dihydropyran ring was found to hydrolyze very easily in the presence of an acid, giving back the starting material. Oxidation of the hydroxy group in the dihydropyran derivatives, followed by hydrolysis, gives a convenient and valuable process for obtaining prostaglandin E analogs from the prostaglandin F analogs already available, without contamination resulting from oxidation of the hydroxyl group at position 3 on the prostaglandin nucleus.

The novel compounds of this invention and the novel processes and intermediates used in their production are illustratively represented in the following reaction scheme:

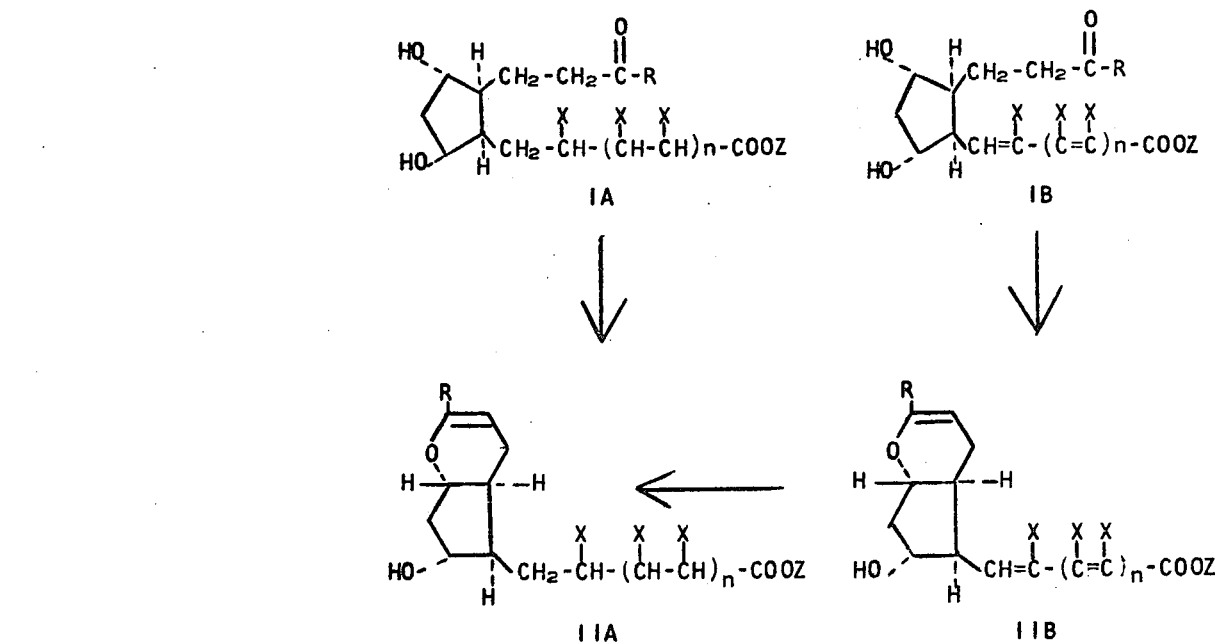

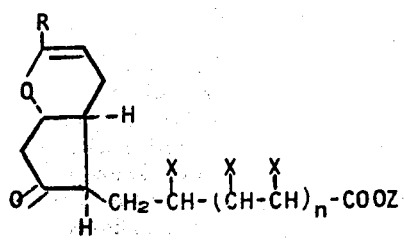
IIIA
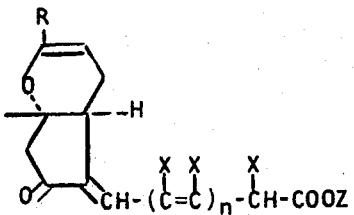
IIIB
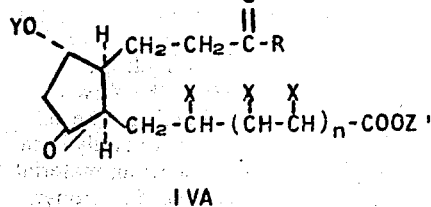
IVA
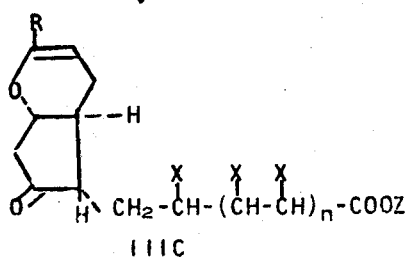
IIIC
IIIB ⟶ 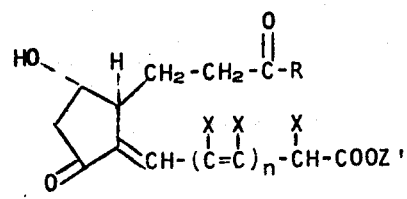
IIIE
IIIC ⟶ 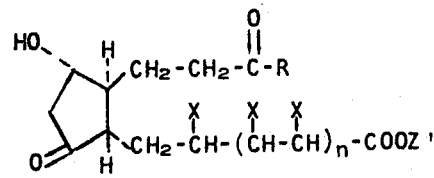
IIID
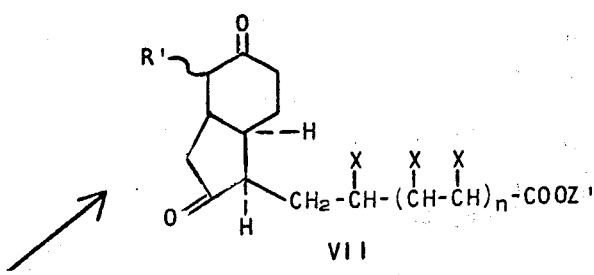
VII

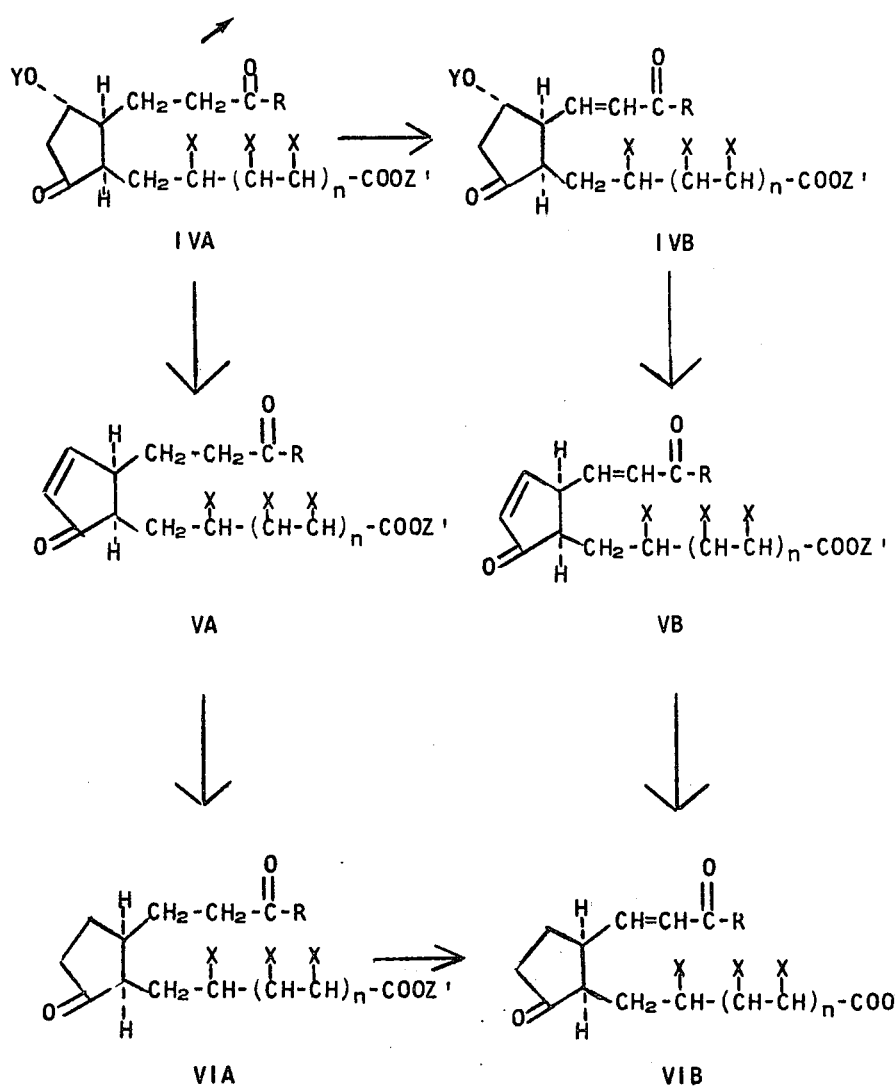
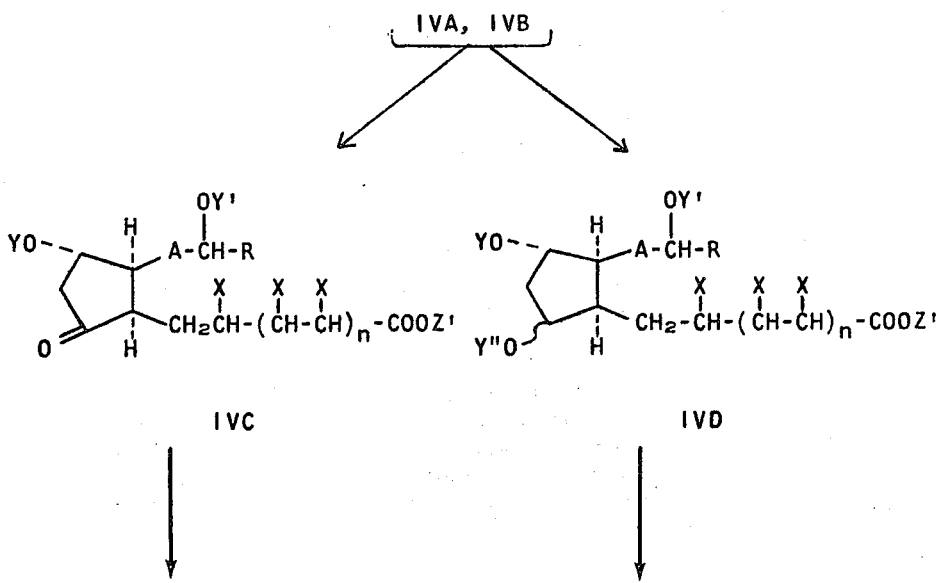

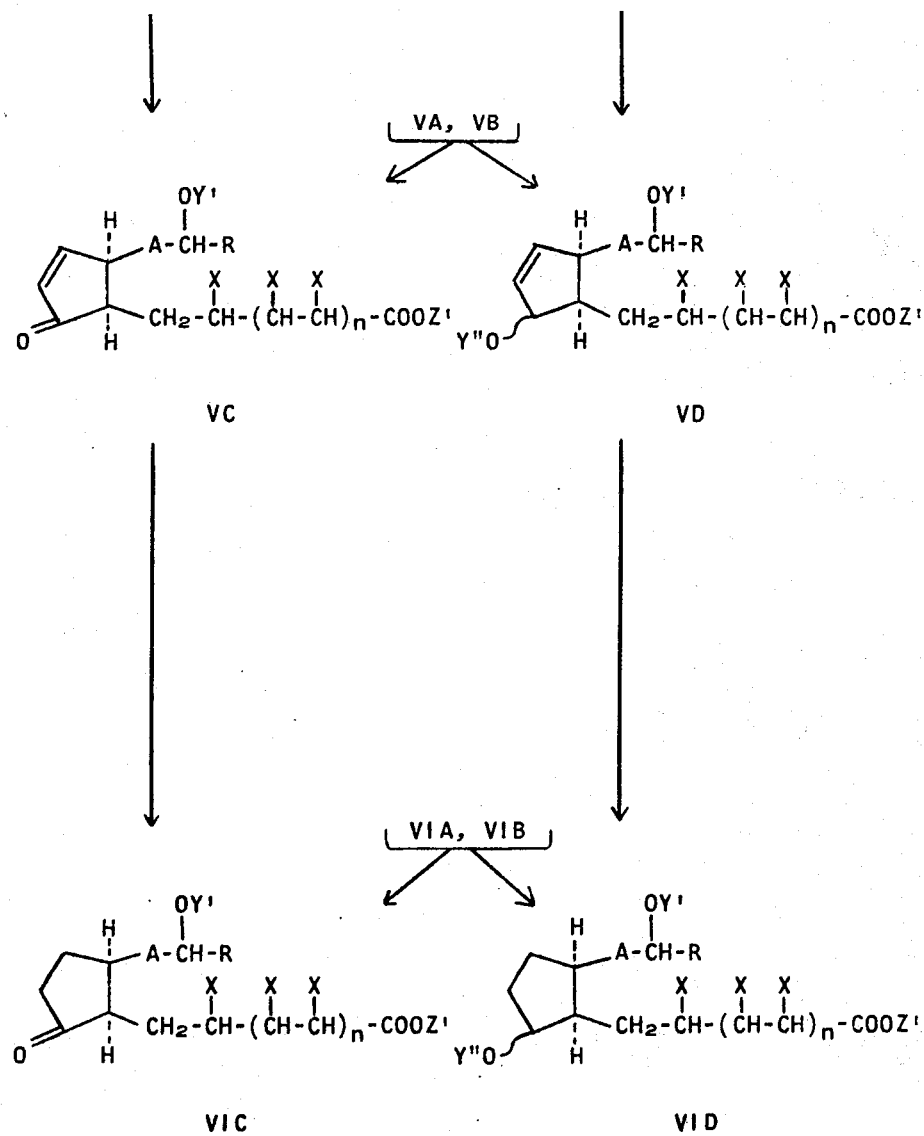

wherein R is an alkyl group, either straight or branched chain, containing from 1 to 8 carbon atoms, inclusive, R' is hydrogen or an alkyl group, either straight or branched chain, containing from 1 to 7 carbon atoms, inclusive, X is hydrogen or methyl with the proviso that not more than one X can be methyl in a given side chain, Y, Y' and Y'' are hydrogen or carboxyacyl, Z is hydrogen, a hydrocarbyl group containing from 1 to 12 carbon atoms, inclusive, Z' is hydrogen, a hydrocarbyl group containing from 1 to 12 carbon atoms inclusive, or a pharmacologically acceptable cation, A is the ethylene radical, —$CH_2$—$CH_2$—, or the vinylene radical, —CH=CH—, and $n$ is 0, 1, or 2.

Examples of alkyl, with one to 8 carbon atoms, are methyl, ethyl, propyl, butyl, pentyl, hexyl, heptyl, octyl, and isomeric forms thereof.

Preferably the carboxyacyl moiety contains one to about 12 carbon atoms. Among the carboxyacyl moieties, lower alkanoyl is preferred.

Examples of lower alkanoyl, i.e., with one to about 12 carbon atoms, are formyl, acetyl, propionyl, butyryl, valeryl, hexanoyl, heptanoyl, octanoyl, decanoyl, undecanoyl, lauroyl, and isomeric forms thereof. Examples of other carboxyacyl moieties within the scope of this invention are crotonyl, cyclohexanecarbonyl, 3-cyclohexenecarbonyl, phenylacetyl, p-chlorophenoxyacetyl, succinyl, benzoyl, p-nitrobenzoyl, naphthoyl, furoyl, 3-pyridinecarbonyl, phthaloyl, and the like.

Preferably the hydrocarbyl moiety contains one to about 12 carbon atoms. Among the hydrocarbyl moieties, alkyl is especially preferred. Examples of alkyl, i.e. with one to about 12 carbon atoms, are methyl, ethyl, propyl, butyl, pentyl, hexyl, heptyl, octyl, nonyl, decyl, undecyl, lauryl, and isomeric forms thereof. Examples of other hydrocarbyl moieties within the scope of this invention are allyl, crotyl, 3-butenyl, 5-hexenyl, propargyl, 4-pentynyl, cyclopentyl, 4-tertbutylcyclohexyl, cyclooctyl, benzyl, 2-naphthylmethyl, and the like.

Pharmacologically acceptable cations within the scope of Z' in formulas IV A-D, V A-D, VI A-D, VII, IIIE, and IIID, can be the cationic form of a metal, ammonia, or an amine, or can be quaternary ammonium ions. Expecially preferred metal cations are those derived from the alkali metals, e.g., lithium, sodium, and potassium, and from the alkaline earth metals, e.g., magnesium, calcium, strontium, and barium, although the cationic form of other metals, e.g., aluminum, zinc, iron, and silver is within the scope of this invention. Pharmacologically acceptable amine cations can be derived from primary, secondary, or tertiary amines. Examples of suitable amines are methylamine, dimethylamine, trimethylamine, ethylamine, dibutylamine, triisopropylamine, N-methylhexylamine, decylamine, allylamine, crotylamine, cyclopentylamine, dicyclohexylamine, benzylamine, dibenzylamine, $\alpha$-phenylethylamine, $\beta$-phenylethylamine, ethylenediamine, diethylenetriamine, and like lower-aliphatic, lower-cycloaliphatic, and lower-araliphatic amines containing up to and including about 18 carbon atoms, as well as heterocyclic amines such as piperidine, morpholine, pyrrolidine, piperazine, and lower-alkyl derivatives thereof, such as 1-methylpiperidine, 4-ethylmorpholine, 1-isopropyl-pyrrolidine, 2-methylpyrrolidine, 1,4-dimethylpiperazine, 2-methylpiperidine, and the like, as well as amines containing water-solubilizing or hydrophilic groups such as mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane N-phenylethanolamine, N-(p-tert-amylphenyl)diethanolamine, galactamine, N-methylglucamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium, and the like.

In the process of this invention all the compounds can be produced as racemic mixtures. Alternatively, the racemic mixtures can be resolved at appropriate stages by methods well known in the art, whereupon subsequent products may be obtained as the corresponding optically pure enantiomers. In the chart both enantiomeric forms as well as the racemic forms are depicted by a single representation which should, however, not be considered to limit the scope of the disclosure.

The natural prostaglandins exhibit a multitude of pharmacological activities (see for example S. Bergstrom and B. Samuelsson, Ann. Rev. of Biochem., 34, 1965). The prostaglandin analogs of the present invention, compounds IVA-D, VA-D and VIA-D, which possess cis-side chains in contrast to the trans-side chains of tne natural prostaglandins, show a different spectrum of activity as compared to the natural prostaglandins. They act as antagonists of particular activities of the prostaglandins and show a separation of activity between desired and associated activities of prostaglandins.

Compounds IIIA, IVA and IVB possess activity as antagonists to epinephrine in lipid mobilization and are essentially inactive in their action on smooth muscle and in lowering blood pressure. The compounds of formulas IIIA, IVA, and IVB are therefore of value in treating disease states in man where an agent is required that blocks mobilization of free fatty acids (see for example Carlson and Bailey, Chapter 57, Section 5, Adipose Tissue, in Am. Physiological Society Handbook of Physiology).

Compounds IVC, VA-D and VIA-D exhibit hypotensive and smooth muscle stimulating activity. The hypotensive activity of these compounds makes them useful in the control of hypertension in man and valuable domestic animals and in laboratory animals such as mice, rats and rabbits.

The compounds of formulas IVA-D VA-D and VIA-D also possess activity as fertility controlling agents, central nervous system regulatory agents, salt- and water-retention regulatory agents, fat metabolic regulatory agents and as serum cholesterol-lowering agents which latter activity makes said compounds useful in the prevention of the onset of atherosclerosis and also in the treatment thereof in man and valuable domestic animals. The activity of said compounds as fat metabolic regulatory agents makes them useful in the control of obesity in man and valuable domestic animals. These compounds may be administered to man by intravenous infusion, subcutaneous injection, or by oral and buccal administration.

Compounds IVC, VA-D, and VIA-D produce pronounced changes in blood pressure and block the action of vasopressin on the bladder, altering fluid transport. Agents which counteract or block the actions of prostaglandin are of great interest in clinical research. To assay large numbers of compounds for prostaglandin blocking activity requires a steady supply both for treatment of control animals and for coadministration to test animals with potential blockers. Thus, the compounds listed above can be substituted for $PGE_1$, a costly and rare material, in laboratory studies for detecting agents which counteract or block the action of $PGE_1$. The compounds listed above are also useful because they can be administered to laboratory animals, preferably rats, to produce a pharmacologic response similar to that produced by $PGE_1$. Animals so treated can then serve as test animals in the serach for and study of compounds which are antagonists of $PGE_1$ and of the administered compounds and which, for that reason, would be useful in blocking or terminating their effects and in blocking endogenously produced prostaglandins. For these purposes, the compounds listed above are advantageously administered to the test animal by continuous intravenous infusion in sterile saline solution, at the rate of about 0.01 to about 10, preferably 0.1 to 1.0 micrograms per kilogram of animal weight per minute and the blocking agent under study admininstered before or during treatment to approximately half the animals. The response is measured in each group and compared to determine the blocking action of the test compound.

In addition, compounds IVA-D, VA-D, and VIA-D have a surprising and unexpected influence on animal cell growth in that they inhibit the usual tendency toward cell differentiation during growth. For example addition of small amounts of the compounds of the formulas listed above to isolated growing segments of chicken skin in a nutrient medium inhibits the formation of feather follicles. Because of that activity, the compounds are useful in experimental medicine, for example in studies of wound healing and of other medical problems involving control of cell differentiation during embryological and subsequent animal growth.

Until recently prostaglandins have been available only in milligram amounts after extraction from semen or seminal vesicle tissue. Recently a biosynthetic procedure has been developed for manufacture of prostaglandins from certain essential fatty acids. This procedure has greatly improved the availability of prostaglandin supplies and has permitted limited screening for prostaglandin-blocking agents. The biosynthetic process is, however, complex, as seminal vesicles from non-castrated rams or bulls are required, essential fatty acids are needed for substrate, and a mixture of products is often encountered, purification of which is difficult and tedious. The cost of producing prostaglandins by this method in sufficient amount to satisfy current needs is so high as to be a limiting factor in research. Thus, in addition to the purposes of this invention stated above, e.g., the control of hypertension, fertility control, fat metabolism regulation, etc., by compounds IVA-D, VA-D and VIA-D it is also a purpose of this invention to provide prostaglandins and prostaglandin-like materials to substitute for natural prostaglandins in the prostaglandin antagonist assays. It is still another purpose to provide a synthetic method for preparing prostaglandins and prostaglandin-like materials in substantial amount and in good purity to provide standard materials for use in prostaglandin antagonist assays. It is a further purpose to prepare sufficient prostaglandins and prostaglandin-like materials to permit a large scale screening of large numbers of compounds in sufficient numbers of animals to obtain statistically significant biological data in prostaglandin antagonist assays.

The hexahydro-2,5-dioxo-1-indanealkanoic acids and esters of formula VII exhibit vasodepressor and lipid mobilizing activity and are useful in the treatment of hypertension and hyperlipemia in man and other animals when administered sublingually, intramuscularly, or intravenously in appropriate dosage forms. An appropriate dosage for ethyl 4-butyl-3a-4,5 6,7,7α-hexahydro-2,5-dioxo-1β-indaneheptanoate is from 0.002 to 0.2 γ/kg.

The compounds of formulas IIA and IIB have prostaglandin-like activity.

In carrying out the process of the present invention, compounds of formula IA are cyclized to produce the compounds of formula IIA. The cyclization can take place under unexpectedly mild conditions, for example by heating at about 100° C or above. The reaction can conveniently be carried out in an inert organic solvent, such as toluene, o-, m- or p-xylene, n-heptane, n-octane, and other hydrocarbon solvents of appropriately high boiling point, about 100° C. or over. Ethers, e.g., dioxane, and like inert solvents can also be used. Water is formed during the reaction, and solvents which form azeotropic mixtures, for example toluene and xylene, are preferred since they provide an efficient means for removing the water.

The time required for reaction depends upon the temperature and the rate at which water is removed. Reaction times of about 1 hour to about 60 hours or longer are operable, about 10 to 50 hours is preferred. To minimize decomposition during the cyclization reaction an inert atmosphere, e.g. nitrogen, is preferred.

If the attached carbon atom in the alkyl group "R" of compounds IA and IB carries one or more hydrogen atoms, the cyclized products can have two structures, as shown below for the cyclization of compound IA:

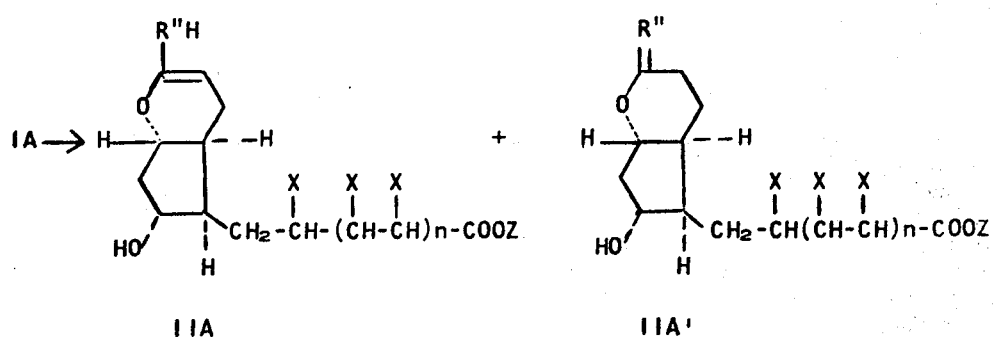

wherein R'' is an alkylidene group containing 1 to 8 carbon atoms, inclusive, and R''H is the same as R. Varying amounts of IIA' can be formed depending on the nature of R'' and the reaction conditions. Separation of IIA and IIA' can be accomplished if desired by repeated chromatography over silica gel and by reversed phase partition chromatography on siliconized celite or preparative thin layer chromatography on silica gel. The products can be characterized by mass spectroscopic analysis and nuclear magnetic resonance analysis, and by their characteristic behaviour after ozonolysis. Separation is not necessary for the process of this invention, since the hydroxy group of compounds of formula IIA' can be oxidized and the oxidized product then hydrolyzed in the same manner to give the same product as described for compounds of structure IIA.

Compounds designated IIB', IIIA', IIIB' and IIIC', analogous to IIA' in having an R' group attached by an exocyclic double bond but coresponding otherwise to the compounds of formulas IIB, IIIA, IIIB, and IIIC can likewise be obtained in carrying out the process of this invention. Compounds IIB', IIIA', IIIB' and IIIC', either pure or mixed with the corresponding compounds IIB, IIIA, IIIB and IIIC, can be used in carrying out the process of this invention in the same manner as compounds IIB, IIIA, IIIB and IIIC. Formulas IIA, IIB, IIIA, IIIB and IIIC in the flowsheet above are intended to represent compounds IIA', IIB', IIIA', IIIB' and IIIC' as well.

Compounds of formula IIB are prepared by cyclization of the compounds of formula IB in the same manner as described above for the cyclization of compounds of formula IA. Hydrogenation of the compounds of formula IIB produces compounds of formula IIA. The hydrogenation is carried out under conditions usual for the hydrogenation of ethenoid compounds, and common hydrogenation catalysts can be used;

palladium and rhodium are preferred. The hydrogenation is stopped when about the theoretical amount of hydrogen for saturation of the unsaturated carboxylic acid side chain has been absorbed.

The keto compounds of formula IIIA are prepared by oxidation of the hydroxy compounds of formula IIA. Since these compounds are sensitive to acid, acid conditions are preferably avoided during the oxidation reaction. Suitable oxidants are, for example, chromic anhydride in pyridine, dimethylsulfoxide and dicyclohexylcarbodiimide or diisopropylcarbodiimide, and activated manganese dioxide, or the Oppenaeur reaction can be used. Isolation of the oxidized product can be accomplished by conventional procedures. During the isolation procedures care must be exercized to avoid acid conditions otherwise some hydrolysis of the pyran ring can take place, giving the prostaglandin analogs of formula IVA. These can be separated if desired from the compounds of formula IIIA by, for example, chromatography over silica gel. For the preparation of compounds of formula IVA, the mixture comprising a compound of formula IIIA and a compound of formula IVA can be used.

The compounds of formula IVA are obtained by acid hydrolysis of the compounds of formula IIIA. The hydrolysis is preferably carried out in an aqueous-organic solvent mixture. Methanol, ethanol, acetone, dioxane, dimethylsulfoxide and the like are suitable solvents. Suitable acids include, for example, acetic acid, benzoic acid, succinic acid, lactic acid, chloroacetic acid, p-toluenesulfonic acid, hydrochloric acid, hydrobromic acid and sulfuric acid. The time required for the hydrolysis to reach completion varies from a few minutes to a few hours, depending upon the temperature and the acidity of the hydrolysis mixture. Preferably the hydrolysis is carried out at room temperature or below, with dilute acids, and the reaction mixture is neutralized as soon as substantial hydrolysis has taken place as a precaution against loss of the 3-hydroxyl group, which can occur in substantial amounts in an acid medium. Loss of the hydroxyl group results in formation of compounds of formula VA, which can be separated from the compounds of formula IVA by, for example, chromatography over silica gel.

Isolation of the compounds of formula IVA can be accomplished by conventional methods, for example by neutralizing the acid reaction mixture with a base such as sodium bicarbonate, potassium carbonate, ammonium hydroxide, sodium hydroxide and the like and extracting the product. Purification can be accomplished by conventional methods as described above.

Oxidation of the hydroxyl group of compounds of formula IIB leads to the keto compounds of formula IIIB, wherein the keto group is conjugated with the double bonds in the side chain. This oxidation is carried out in the same manner as the oxidation of compounds of formula IIA to give IIIA. Since the compounds of formula IIB and IIIB are more susceptible to destruction by excess reagent or harsh reaction conditions than compounds of formula IIA and IIIA, careful oxidation under mild conditions is employed. Suitable oxidizing agents are, for example, dicyclohexylcarbodiimide, diisopropylcarbodiimide, together with dimethyl sulfoxide [Moffet et al., JACS 87, 5661 and 5670 (1965)], catalytic oxygenation, the treatment of the chloroformate with dimethyl sulfoxide [Barton procedure, J. Chem. Soc., 1855 (1964)] and the Oppenauer process. Preferably the reaction is interrupted as soon as the oxidation is substantially complete. Isolation of the product is by conventional methods well known in the art for working up the oxidation reactions named above.

Compounds of formula VA can be prepared by mixing the compounds of formula IVA with a carboxylic acid and maintaining the mixture until a substantial proportion of the formula IVA reactant is transformed to the desired product. Other acids than carboxylic acids, for example, hydrochloric acid, sulfuric acid, and perchloric acid can be used for this transformation of formula IVA compounds to formula VA compounds, but it is usually preferred to use the carboxylic acid because higher yields of relatively pure formula VA compounds are usually obtained thereby.

Although substantially any carboxylic acid can be used as a reagent in the novel process of this invention, it is preferred to use a lower alkanoic acid, i.e., with two to about 8 carbon atoms. Examples of lower alkanoic acids are acetic acid, propionic acid, butyric acid, valeric acid, hexanoic acid, heptanoic acid, octanoic acid, and isomeric forms thereof, e.g., pivalic acid. Especially preferred as a reactant is acetic acid. Other suitable acids are decanoic acid, crotonic acid, chloroacetic acid, succinic acid, tartaric acid, cyclohexaneacetic acid, maleic acid, adipic acid, benzoic acid, p-nitrobenzoic acid, phenylacetic acid, nicotinic acid, and the like.

It is often advantageous, especially with such lower alkanoic acids as acetic acid, to add a small amount of water to the reaction mixture, preferably about one to about 25 percent by weight of the acid reagent. For reasons not completely understood, the water appears to accelerate the reaction and to produce better yields of higher purity product. This is especially true when $R_2$ and $R_3$ are hydrogen in the formula IVA prostaglandin analog reactant.

The amount of the carboxylic acid reagent is not critical although it is usually advantageous to use at least one molecular equivalent of the acid reagent per molecular equivalent of the formula IVA prostaglandin analog derivative reactant. It is preferred to use a substantial excess of the carboxylic acid reagent, e.g., about 5 to about 5,000 molecular equivalents or even more, per molecular equivalent of the formula IVA reactants, especially when the carboxylic acid reagent is sufficiently volatile to be removed by evaporation or distillation at reduced pressure.

When the carboxylic acid reactant is a liquid at the reaction temperature, excess acid can act as a reaction diluent. An inert diluent can also be added, and use of one is preferred when the acid reactant is a solid at the reaction temperature. Examples of suitable inert diluents are lower alkanols, e.g., ethanol and butanol; lower alkyl lower alkanoates, e.g., ethyl acetate and methyl butyrate; lower alkanones, e.g., acetone and diethyl ketone; dioxane; dialkyl formamides, e.g., dimethyl formamide; dialkyl sulfoxides, e.g., dimethyl sulfoxide; and the like.

The preferred reaction temperature range is about 40° to about 150° C. Especially preferred is the range about 50° to about 100° C. The time necessary to transform a substantial proportion of the formula IVA reactant to the desired formula VA derivative product will depend on such factors as the reaction temperature, the nature and amount of the carboxylic acid reagent, and the nature and amount of the diluent, if one is used. When acetic acid containing 10 percent by weight of water is used with the formula IVA reactant wherein R is pentyl, X and Y are hydrogen, Z is ethyl and $n$ is 2, heating at 60° C. for 20 hours gives satisfactory results.

The formula VA products of the novel process of this invention are usually less polar than the formula IVA reactants. For that reason, a product and the corresponding reactant can easily be separated by chromatography, preferably by thin layer chromatography.

By that thin layer chromatography, the course of the novel process of this invention can readily be followed by observing the gradual appearance of the desired formula VA product and the gradual disappearance of the formula IVA reactant on thin layer chromatograms. Small aliquots of the reaction mixture can be taken during the reaction. When a chromatographic spot corresponding to the formula IVA reactant no longer appears, the reaction is complete.

The desired formula VA product can be isolated from the reaction mixture, if desired, by conventional methods, for example, by evaporation of diluent and excess carboxylic acid, if the latter is sufficiently volatile, or by conventional chromatographic or selective extraction procedures. The formula VA product can also be further purified, if desired, by conventional procedures, preferably by chromatography.

The novel compounds of formula VIA can be prepared by catalytic hydrogenation of the compounds of formula VA. Rhodium and palladium catalysts, especially on a carbon carrier, are preferred for this catalytic hydrogenation. It is also preferred that the hydrogenation by carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 10° to about 100° C. are preferred. The formula VIA product can be isolated by conventional techniques, for example, removal of the catalyst by filtration, followed by evaporation of the solvent. The product can then be purified, advantageously by chromatography. Silica gel and diatomcaeous earth are especially preferred as the chromatography solids.

The compounds of formula IVB are prepared from the compounds of formula IVA by treatment with excess selenium dioxide in an inert solvent, for example tetrahydrofuran, benzene, toluene, dioxane, and the like. The reaction temperature is preferably from 40° to 100° C.; usually the reaction is carried out at the boiling point of the solvent employed. The product is isolated by conventional means, for example by removing the insoluble selenium dioxide from the reaction mixture by filtration, centrifugation, or the like, and extracting or evaporating the resulting solution. The formula IVA product can be further purified by chromatography, for example over silica gel or Florisil (synthetic magnesium silicate), by countercurrent extraction, or by other conventional means.

Compounds of formula VIB are produced from compounds of formula VIA by treatment with selenium dioxide as described above.

Reduction of the compounds of formulas: IVA, VA, and VIA with 0.25 molecular equivalent of a borohydride or lithium aluminum (tri-tert.-butoxy)hydride transforms the side chain keto group of the formula IVA, VA, or VIA reactant to an hydroxy group giving the corresponding compounds of formulas IVC, VC and VIC, wherein A is —CH$_2$—CH$_2$. Similar reduction of the compounds of formulas IVB, VB and VIB gives the corresponding compounds of formulas IVC, VC, and VIC, wherein A is —CH=CH—. These reductions can be carried out by methods known in the art for borohydride reductions of other prostanoic acid derivatives. See, for example, Bergström et al., Acta Chem. Scand. 16, 969 (1962) and Änggård et al., J. Biol. Chem. 239, 4101 (1964). Sodium borohydride, potassium borohydride, or lithium aluminum (tri-tert-butoxy)hydride are preferred for these reductions. Lower alkanols, e.g., methanol and ethanol, are preferred as reaction solvents, although other solvents, e.g., dioxane and diethylene glycol dimethyl ether can also be used, especially in combination with the lower alkanol. It is preferred to add a solution or suspension of the reducing agent to the ketone reactant, although the reverse order can also be used. A reaction temperature in the range about 0° to about 50° C. is usually satisfactory. At about 25° C., the desired reaction is usually complete in about 0.5 to 5 hours. The resulting complex compound is then transformed to the desired product in the usual manner by treatment with aqueous acid, advantageously dilute hydrochloric acid.

The desired formula IVC, VC or VIC reduction product can be isolated by conventional techniques, for example, evaporation of the reaction solvent and extraction of the residual aqueous mixture with a water-immiscible solvent, for example, diethyl ether. Evaporation of the latter solvent then gives the desired product.

These borohydride or lithium aluminum (tri-tert-butoxy)hydride reductions of the side chain keto group of formula IVA, VA, VIA, IVB, VB and VIB reactants each produce a mixture of an αhydroxy compound and an isomeric (epimeric) β-hydroxy compound. These mixtures of isomeric hydroxy compounds can be used for the purposes described herein for compounds of formulas IVC, VC and VIC. Alternatively, the isomeric compounds in a pair of hydroxy compounds can be separated from each other by methods known in the art for the separation of analogous pairs of isomeric prostanoic acid derivatives. See, for example, Bergström et al., Acta Chem. Scand. 16, 969 (1962), Granström et al., J. Biol. Chem. 240, 457 (1965), and Green et al., ibid. Especially preferred as separation methods are partition chromatographic procedures, both normal and reversed phase, thin layer chromatography, and countercurrent distribution procedures.

An alternate route for the production of compounds of formula IVC from compounds of formula IIA begins with the acylation of the 6α-hydroxy group of the formula IIA compound, for example with acetic anhydride and pyridine. The formula IIA acylate is then treated with dilute acid, as described above for the hydrolysis of formula IIIA compounds to produce formula IVA compounds, giving the 5-monoacylate of a formula I compound, which is treated with sodium borohydride to reduce the side chain keto group. The thus obtained diol is treated with dihydropyran in the presence of an acid to etherify the hydroxy groups, then the 5-acyl group is removed by alkaline hydrolysis and the free 5-hydroxy group is transformed to a keto group by oxidation with, for example, chromium trioxide in pyridine giving the di-tetrahydropyranyl ether of the formula IVC compound. The formula IVC compound can then be obtained by removal of the ether protecting groups, for example by treatment with 90% acetic acid.

Reduction of the compounds of formulas IVA, VA, VIA, IVB, VB and VIB as described above but with excess borohydride or lithium aluminum (tri-tertbutoxy) hydride produces the corresponding compounds of formulas IVD, VD and VID, wherein both the side chain and the nuclear keto groups are reduced to hydroxy. Preferably about 1 to about 15 molecular equivalents of reducing agent is used per molecular equivalent of ketone reactant. The compounds of formulas IVD, VD and VID can be separated and purified as described above for the products IVC, VC and VIC.

Compounds of formulas IVB, IVC, and IVD possess hydroxy or acyloxy groups at position 3 of the cyclopentane nucleus and can be dehydrated in the presence of an acid to give the 3-unsaturated compounds of formulas VB, VC, and VD under the conditions described above for the preparation of compounds of formula VA from the compounds of formula IVA. The 3-unsaturated compounds VB, VC and VD can then be hydrogenated to give the compounds of formulas VIB, VIC and VID under the conditions described above for the hydrogenation of the compounds of formula VA to produce the compounds of formula VIA. When the side chain at position 2 is also unsaturated as in VB, VC(A= —CH=CH—), and VIC (A= —CH=CH—)hydrogenation with one equivalent of hydrogen results in a mixture of products. If about two equivalents of hydrogen is used, then only the formula VI products with both ring and side chain saturated are isolated, i.e. compounds of formulas VIA, VIC (A= —CH$_2$—CH$_2$—) and VID (A= —CH$_2$—CH$_2$—).

The compounds of formula IIIA, when treated with an acid, give prostaglandin analogs having a cis side chain configuration, i.e. the compounds of formula IVA. Prostaglandin analogs having a trans side chain configuration can be obtained from the compounds of formula IIIB, i.e. the compounds of formula IIID. When compounds of formula IIIB are treated with an acid, as described above for the preparation of compounds of formula IVA from the compounds of formula IIIA, the ylidene compounds of formula IIIE are obtained and these can be hydrogenated to give the compounds of formula IIID following the procedure used for the reduction of the compounds of formula IIB to give the compounds of formula IIA. Alternatively the compounds of formula IIIB can be first hydrogenated to give compounds of formula IIIC, and these on acid treatment as described above give the compounds of formula IIID. The compounds of formula IIID have PGE antagonist activity and anti-lipolytic activity and are therefore useful in treating disease of abnormal lipid transport or metabolism.

The prostaglandin analogs of formulas IVA-D, VA-D, VIA-D, IIID and IIIE, and compound VII can all possess an esterified carboxyl group. Hydrolysis of the ester group is carried out in a conventional manner, preferably with a dilute alkali such as sodium or potassium hydroxide, or sodium or potassium carbonate or bicarbonate, in an aqueous-organic solvent mixture. The product is recovered in a conventional manner, for example, by acidification of the reaction mixture and extraction with a water-immiscible solvent, use of an ion exchange resin etc.

The compounds of formula IVA, when heated with a base such as sodium or potassium hydroxide, sodium or potassium carbonate, and the like in an organic or aqueous organic solvent, for example methanol, ethanol, propanol, butanol, t-butanol, dioxane and the like, preferably at the reflux temperature of the solvent, are transformed to the hexahydro-2,5-dioxo-1-indane alkanoic acids of formula VII. The formula VII product is recovered in a conventional manner, for example, by acidification of the reaction mixture and extraction with a water-immiscible solvent, use of an ion exchange resin, etc. The product is purified in a conventional manner, for example by chromatography over acid-washed silica gel and elution with ethyl acetate, ethyl acetate-benzene mixture, and the like.

The thus obtained free acids of formulas IVA-D, VA-D, VIA-D, IIID, IIIE and VII can be converted to their corresponding esters. This reaction is carried out by reacting the selected acid with a diazoalkane, e.g., diazomethane, diazoethane, diazobutane, 1-diazo-2-ethylhexane, cyclohexyldiazomethane, diazododecane, and the like, in the presence of an inert organic solvent, e.g., methanol, diethyl ether, tetrahydrofuran, dioxane, chloroform, and the like, or a mixture thereof, preferably in a 10% methanol - 90% diethyl ether mixture at a temperature of 0° to 50° C., with room temperature (25° C.) being preferred. The products are then purified by conventional means, e.g., evaporation to residue, followed by chromatography.

An alternative method for esterification of the free acids of formulas IVA-D, VA-D, VIA-D, IIID, IIIE and VII comprises transformation of the free acid to the corresponding silver salt, followed by interaction of that salt with a hydrocarbyl iodide. Examples of suitable iodides are methyl iodide, ethyl iodide, butyl iodide, isobutyl iodide, tert-butyl iodide, decyl iodide, benzyl iodide, cyclohexyl iodide, crotyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Carboxyacylation of the hydroxy moiety or moieties in formula IIA, IIB, IVA-D, VC, VD, VIC, VID, IIIE and IIID prostaglandin analogs is accomplished by interaction of the hydroxy compound with a carboxyacylating agent.

Although substantially any carboxyacylating agent can be used to produce these carboxyacylates, especially suitable are the anhydrides, mixed anhydrides, and acid chlorides of alkanoic, cycloalkanoic, alkenoic, cycloalkenoic, aralkanoic, aromatic, and heterocyclic carboxylic acids. These anhydrides and acid chlorides can also be substituted with any of a wide variety of atomic or molecular moieties. Examples of such substituents are alkyl, e.g., methyl, butyl, decyl; alkoxy, e.g., methoxy, ethoxy, pentyloxy; alkylthio, e.g., methylthio, propylthio, heptylthio; dialkylamino, e.g., dimethylamino, diethylamino, dihexylamino; alkoxycarbonyl, e.g., methoxycarbonyl, propoxycarbonyl, nonoxycarbonyl; carboxyacyl, e.g., acetyl, butyryl; carboxamido, e.g., benzamido, acetamido; nitro; fluoro; cyano; and the like. Chlorine, bromine, and iodine can also be substituents on aromatic portions of the carboxyacylating agents.

Examples of suitable anhydrides are acetic anhydride, propionic anhydride, butyric anhydride, isobutyric anhydride, acrylic anhydride, crotonic anhydride, cyclohexanecarboxylic anhydride, benzoic anhydride, naphthoic anhydride, furoic anhydride, and the like, as well as the corresponding anhydrides substituted with one or more of the above-mentioned substituents. Examples of suitable acid chlorides are acetyl chloride, propionyl chloride, butyryl chloride, isobutyryl chloride, decanoyl chloride, acryloyl chloride, crotonoyl chloride, cyclohexanecarbonyl chloride, 3-cyclohexenecarbonyl chloride, phenylacetyl chloride, succinyl chloride, benzoyl chloride, naphthoyl chloride, furoyl chloride, 3-pyridinecarbonyl chloride, phthaloyl chloride, and the like, as well as the corresponding acid chlorides substituted with one or more of the above-mentioned substituents.

The carboxyacylation is advantageously carried out by mixing the hydroxy compound and the acid anhydride preferably in the presence of a tertiary amine such as pyridine or triethylamine. A substantial excess of the anhydride should be used, preferably about 10 to about 10,000 moles of anhydride per mole of the hydroxy compound reactant. The excess anhydride serves as a reaction diluent and solvent. An inert organic diluent, for example, dioxane, can be added. It is preferred to use enough of the tertiary amine to neutralize the carboxylic acid produced by the reaction as well as any free carboxyl groups present in the hydroxy compound reactant.

The carboxyacylation reaction is preferably carried out in the range about 0° to about 60° C. The necessary reaction time will depend on such factors as the reaction temperature and the nature of the anhydride and tertiary amine reactants. With acetic anhydride, pyridine, and a 25° C. reaction temperature, a 12 to 24-hour reaction time should be used.

The carboxyacylated product is isolated from the reaction mixture by conventional methods. For example, the excess anhydride can be decomposed with water, and the resulting mixture acidified and then extracted with a solvent such as diethyl ether. The desired carboxyacylate will usually be extracted by the ether and is recoverable therefrom by evaporation. If desired, the carboxyacylate can be purified by conventional methods, preferably by chromatography.

The free acids of formulas IVA-D, VA-D, VIA-D, IIID, IIIE and VII can be transformed to pharmacologically acceptable salts by neutralization with appropriate amounts of the corresponding inorganic or organic base, examples of which correspond to the cations listed above. These transformations can be carried out by a variety of procedures known in the art to be generally useful for the preparation of inorganic, i.e., metal or ammonium, salts, amine acid addition salts, and quaternary ammonium salts. The choice of procedure will depend in part upon the solubility characteristics of the particular salt to be prepared. In the case of the inorganic salts, it is usually suitable to dissolve the acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt of the prostaglandin analog derivative. Evaporation of the water or addition of a water-miscible solvent of moderate polarity, for example, a lower alkanol or a lower alkanone gives the solid inorganic salt if that form is desired.

To produce an amine salt, the prostaglandin analog derivative can be dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it can usually be obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the prostaglandin analog derivative with the stoichiometric amount of the corresponding quaternary ammonium hydroxide in water solution, followed by evaporation of the water.

The racemic products and intermediates of this invention can be resolved into their optically active components by a number of methods of resolution well known in the art. Those compounds which are free acids or capable of being converted to free acids are treated with an optically active base, e.g., cinchonine, quinine, brucine or d- and l- α-phenylethylamine to produce diastereoisomeric salts which can be separated by crystallization. Alternatively, the acid may be esterified with an optically active alcohol, e.g., d- and l-menthol, estradiol 3-acetate, and the diastereoisomeric esters then resolved. In addition, the compounds containing free hydroxyl groups can be acylated with the acid chloride or anhydride of an optically active acid, or the free acid in the presence of an esterification catalyst, e.g., d-camphorsulfonic acid, α-bromocamphorsulfonic acid, and d- and 1-6,6'-dinitrodiphenic acid, to give diastereoisomeric esters which are resolvable by crystallization.

Resolution of the racemic prostaglandins and prostaglandin-like compounds of this invention can also be accomplished by reverse phase and adsorption chromatography on an optically active support and adsorbent and by selective transformation of one isomer with a biologically-active prostaglandin transforming system, for example, the 15-dehydrogenating system present in lung such as guinea-pig, rat, and pig lung and in microorganisms such as fungi. Such transformation can be carried out by incubation or perfusion using methods well established in the art, followed by isolation and recovery of both the isomer resistant to the metabolic transformation applied, and the product formed by the enzymatic transformation.

The starting materials for this invention, the compounds of formulas IA and IB, can be prepared by the processes shown in Preparations 1 to 34, below, and represented by the following sequence of formulas:

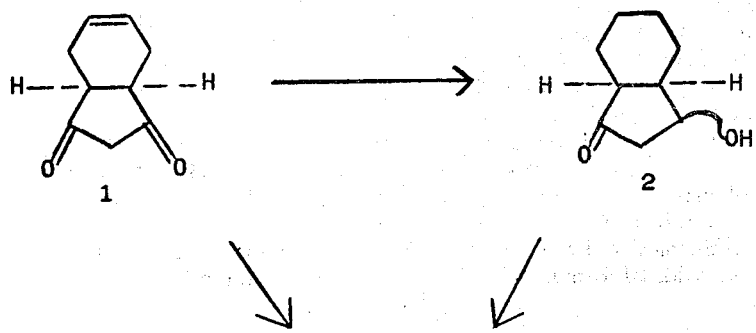

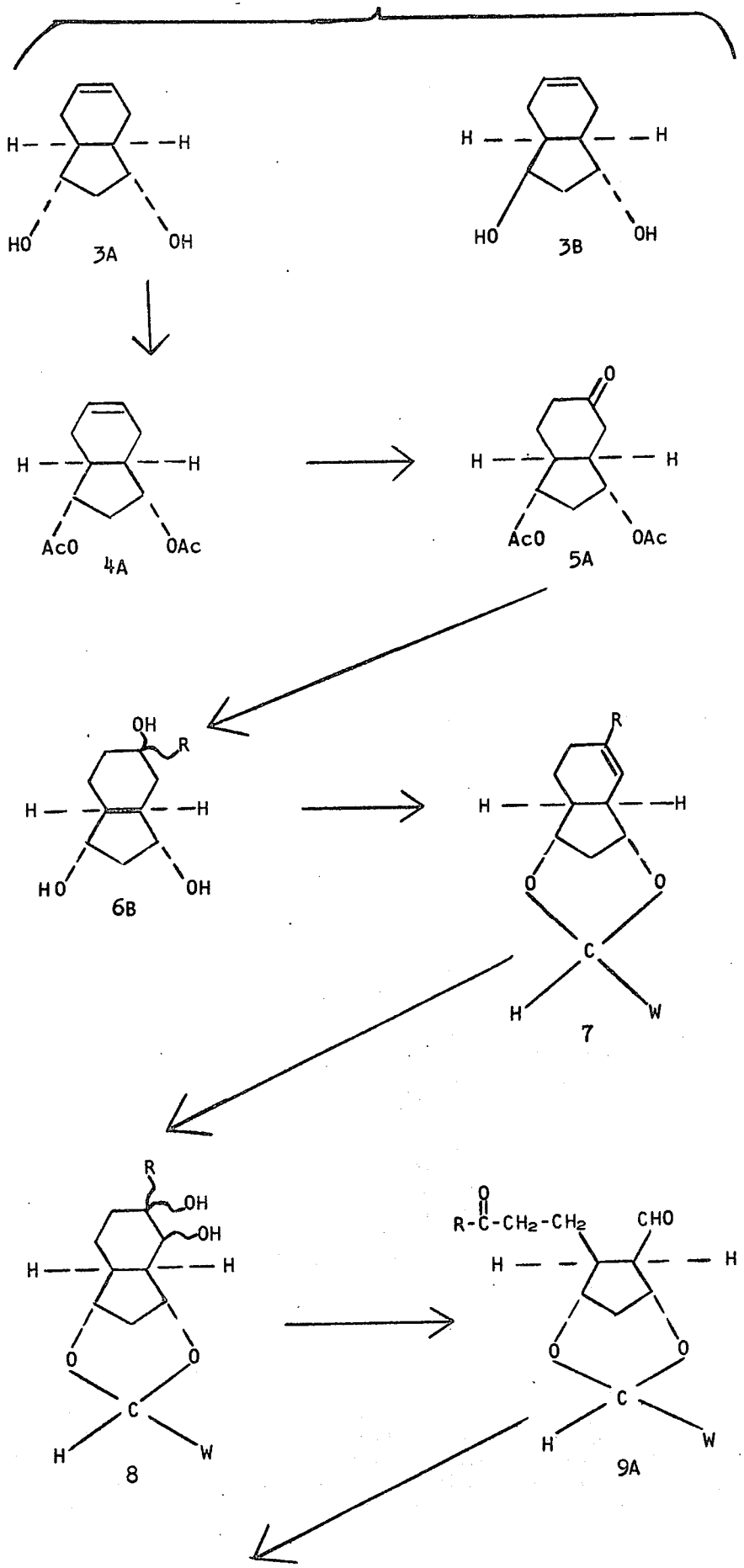

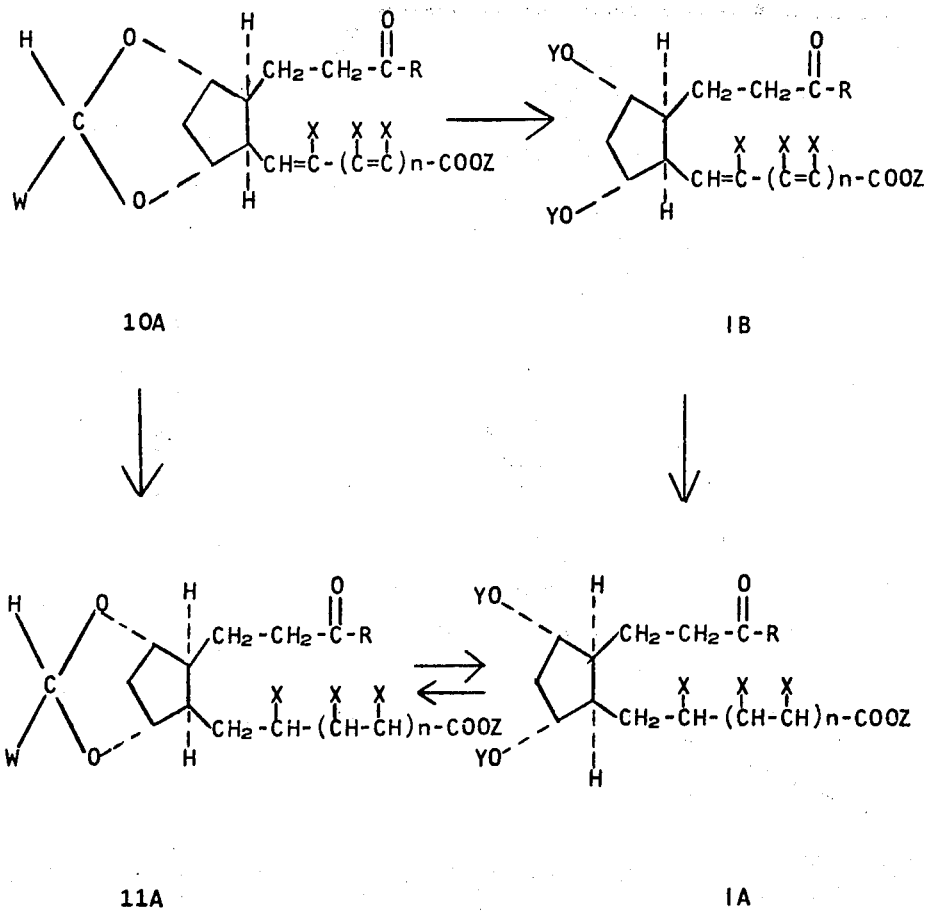

wherein Ac is the acyl radical of a hydrocarbon carboxylic acid containing from 1 to 12 carbon atoms, inclusive, R is an alkyl group, either straight or branched chain, containing from 1 to 8 carbon atoms, inclusive, Z is hydrogen or an alkyl group containing from 1 to 12 carbon atoms, inclusive, W is hydrogen, an alkyl or substituted alkyl group containing from 1 to 8 carbon atoms, inclusive, or an aryl or substituted aryl group containing from 6 to 8 carbon atoms, inclusive, Y and Y' are hydrogen or the acyl radical of a hydrocarbon carboxylic acid containing from 1 to 12 carbon atoms, inclusive, $n$ is an integer selected from the group consisting of 0, 1 and 2, and X is hydrogen or methyl with the proviso that not more than one X can be methyl in a given side chain.

In a number of the examples which follow, nuclear magnetic resonance spectroscopy (N.M.R.) has been used along with other instrumental properties, such as infra-red (I.R.) and ultraviolet (U.V.) spectroscopy and mass spectroscopy to characterize and define the products obtained. For discussions of N.M.R. spectroscopy and its application as a definitive measurement and identification of chemical compositions see Bhaca and Williams, Applications of N.M.R. Spectroscopy in Organic Chemistry, Holden Day (1964); L. M. Jackman, Applications of Nuclear Magnetic Resonance Spectroscopy in Organic Chemistry, Pergamon, London (1959); J. D. Roberts, Nuclear Magnetic Resonance, McGraw Hill, N.Y. (1959); Wilberg and Nest, The Interpretation of N.M.R. Spectra, Benjamin, N.Y. (1962).

All N.M.R. data were obtained on the Varian N.M.R. instrument, Model A-60 (run at 60 megacycles) and reported in cycles per second (cps) downfield from the standard tetramethylsilane.

The following preparations and examples illustrate the best mode contemplated by the inventors for carrying out their invention.

PREPARATION 1

3aα,4,7,7aα-tetrahydro-1,3-indanedione (1)

A solution of 26 g. of 4-cyclopentene-1,3-dione and 0.1 g. of pyrogallol in 60 ml. of benzene and 1.5 ml. of acetic acid was cooled in an ice bath and 40 ml. of liquid butadiene was added. The mixture was sealed in a glass pressure vessel and allowed to stand at room temperature for 12 days. The product precipitated and was removed by filtration to give 33.6 g. of 3aα,4,7,7aα-tetrahydro-1,3-indanedione having a melting point of 163°–165° C. A portion was recrystallized from tetrahydrofuran giving pure 3aα,4,7,7aα-tetrahydro-1,3-indanedione having a melting point of 163°–165° C., U.V. absorption $\lambda_{EtOH}^{max.}$ 244 mμ, ∈=15,000, infrared absorption maxima at 3034, 2680, 2520, 2500, 1642, 1582, 1525, 1232, and 1170 cm.$^{-1}$, and the analysis:

Calcd. for $C_9H_{10}O_2$: C, 71.98; H, 7.51. Found: C, 71.51; H, 6.80.

PREPARATION 2

3aα,4,7,7aα-tetrahydro-1,3-indanedione (1)

A mixture of 455 g. of 4-cyclopentene-1,3-dione, 26.2 ml. of glacial acetic acid, 1.75 g. of pyrogallol and 1050 ml. of benzene was placed in an autoclave and cooled to −5° C. or lower, then 700 ml. of liquid butadiene was added. The autoclave and contents was allowed to warm to room temperature while stirring for two hours, then was allowed to stand at room temperature for 12 days. The precipitated solid was removed by filtration and dried at 50° C. under diminished pressure to give 472 g. of 3aα,4,7,7aα-tetrahydro-1,3-indanedione having a melting point of 158°–161° C. and a U.V. absorption $\lambda_{EtOH}^{max.}$ 244 mμ, ∈ = 15,150.

PREPARATION 3

3aα,4,7,7aα-tetrahydro-1α,3α-indanediol (3A) and racemic 3aα,4,7,7aα-tetrahydro-1α,3β-indanediol (3B)

A solution of 10.0 g. of 3aα,4,7,7aα-tetrahydro-1,3-indanedione in 220 ml. of absolute ethanol was heated at reflux under nitrogen while 18.0 g. of sodium in small chunks was added as rapidly as possible without foaming over. The mixture was heated at reflux for a total of 3 hours, then was cooled, diluted with 500 ml. of water and extracted with ethyl acetate. The ethyl acetate extract was concentrated by evaporation under diminished pressure to yield a neutral yellow oil comprising 3aα,4,7,7aα-tetrahydro-1α,3α-indanediol and racemic 3aα,4,7,7aα-tetrahydro-1α,3β-indanediol. The yellow oil was chromatographed over Florisil (synthetic magnesium silicates) and eluted with increasing proportions of acetone in Skellysolve B (mixed hexanes). The first two product fractions in the 15% acetone in Skellysolve B eluates were combined and gave 0.525 g. of crystals melting at 102°–106° C., which on recrystallization from acetone-Skellysolve B mixture gave racemic 3aα,4,7,7aα-tetrahydro-1α,3β-indanediol having a melting point of 106°–107° C., infrared absorption maxima (Nujol) at 3300, 3060, 1650, 1215, 1152, 1100 and 1050 cm.$^{-1}$ and the following analysis:

Calcd. for $C_9H_{14}O_2$: C, 70.10; H, 9.15. Found: C, 70.34; H, 9.15.

Nuclear magnetic resonance analysis showed two CH-O absorption peaks, confirming that the diol melting at 106°–107° C. is a trans diol.

The remainder of the 15% acetone in Skellysolve B eluates and the 20% acetone in Skellysolve B eluates were combined and evaporated to give 2.62 g. of crystals comprising 3aα,4,7,7aα-tetrahydro-1α,3α-indanediol having a melting point of 76°–80° C.; on recrystallization from acetone-Skellysolve B an analytical sample was obtained having a melting point of 79°–83° C., infrared absorption maxima (Nujol) at 3300, 3010, 1650, 1090 and 1051 cm.$^{-1}$ and the following analysis:

Calcd. for $C_9H_{14}O_2$: C, 70.10; H, 9.15. Found: C, 70.03; H, 9.15.

Nuclear magnetic resonance analysis showed the presence of one CH-O absorption peak, confirming that the diol melting at 79°–83° C. is a cis diol.

PREPARATION 4

Racemic 3aα,4,7,7aα-tetrahydro-1α-hydroxy-3-indanone (2) and racemic 3aα,4,7,7aα-tetrahydro-1β-hydroxy-3-indanone (2)

A solution of 5.0 g. of 3aα,4,7,7aα-tetrahydro-1,3-indanedione in 150 ml. of isopropyl alcohol was heated at reflux under nitrogen, then 9.0 g. of sodium in pieces was added as rapidly as possible and the mixture was heated at reflux until the sodium dissolved. The mixture was then cooled, diluted with water, and extracted 3 times with ethyl acetate. The ethyl acetate extracts were combined, washed with water, and evaporated to give 2.34 g. of an oil which was chromatographed over Florisil and eluted with acetone-Skellysolve B. On evaporation of the 10% acetone-Skellysolve B eluate there was obtained 1.546 g. of an oil comprising racemic 3aα,4,7,7aα-tetrahydro-1α-hydroxy-3-indanone and racemic 3aα,4,7,7aα-tetrahydro-1β-hydroxy-3-indanone having infrared absorption maxima ($CH_2Cl_2$) at 3700, 3500, and 1735 cm.$^{-1}$. The 1735 cm.$^{-1}$ absorption indicates the presence of a carbonyl group.

PREPARATION 5

Racemic 3aα,4,7,7aα-tetrahydro-1α-hydroxy-3-indanone (2) and racemic 3aα,4,7,7aα-tetrahydro-1β-hydroxy-3-indanone (2)

A solution of 3.0 g. of lithium in 400 ml. of liquid ammonia was prepared and a solution of 5.0 g. of 3aα,4,7,7aα-tetrahydro-1,3-indanedione in 100 ml. of absolute ethanol was added dropwise. When about three-fourths of the solution of indanedione in ethanol had been added the blue color of the Li/NH$_3$ disappeared, and an additional 2 g. of lithium was added, then addition of the indanedione was completed. The mixture was stirred until the blue color disappeared, then the ammonia was evaporated on a steam bath under a stream of air giving a residue which was dissolved by addition of 400 ml. of ethyl acetate and 200 ml. of water and stirring. The ethyl acetate layer was separated and the solvent removed by evaporation to give 5.1 g. of an oil comprising racemic 3aα,4,7,7aα-tetrahydro-1α-hydroxy-3-indanone and racemic 3aα,4,7,7aα-tetrahydro-1β-hydroxy-3-indanone having infrared absorption maxima indentical with that shown by the product obtained in Preparation 4.

PREPARATION 6

3aα,4,7,7aα-tetrahydro-1α,3α-indanediol (3A)

A solution of 5.1 g. of 3aα,4,7,7aα-tetrahydro-1α-hydrozy-3-indanone (obtained in Prepn. 5) was dissolved in 100 ml. of absolute ether and excess lithium aluminum hydride was added. The thus-obtained mixture was stirred at room temperature for 1.5 hours and ethyl acetate was added to destroy the excess lithium aluminum hydride, then saturated aqueous sodium sulfate was added. The mixture was filtered and the organic layer was separated and evaporated to give a residue comprising a mixture of 3aα,4,7,7aα-tetrahydro-1α,3α-indanediol and racemic 3aα,4,7,7aα-tetrahydro-1α,3β-indanediol, which on crystallization from a mixture of methylene chloride and Skellysolve B (mixed hexanes) gave 2.05 g. of 3aα,4,7,7aα-tetrahydro-1α,3α-indanediol having a melting point of 81°–84° C. The mother liquors from this crystallization are evaporated and the thus-obtained residue is chromatographed following the procedure of Preparation 3 to obtain racemic 3aα,4,7,7aα-tetrahydro-1α,3β-indanediol.

PREPARATION 7

3aα,4,7,7aα-tetrahydro-1α,3α-indanediol (3A)

A solution of 4.9 g. of 3aα,4,7,7aα-tetrahydro-1α-hydroxy-3-indanone in 25 ml of methanol was added to 400 ml. of liquid ammonia, then 1.5 g. of lithium metal was added rapidly. A blue color developed which disappeared after about 5 minutes, then 15 g. of ammonium chloride was added and the ammonia was evaporated under a current of air while heating on the steam bath, giving a residue which was taken up in a mixture of ethyl acetate and water. The ethyl acetate layer was separated and the water layer was extracted with a second portion of ethyl acetate. The ethyl acetate solutions were combined and evaporated to yield a crystalline residue which on crystallization from a mixture of methylene chloride and Skellysolve B gave 1.65 g. of 3aα,4,7,7aα-tetrahydro-1α,3α-indanediol having a melting point of 78°–80° C. The mother liquors are evaporated to give a residue which is chromatographed following the procedure of Preparation 3 to obtain racemic 3aα,4,7,7aα-tetrahydro-1α,3β-indanediol.

PREPARATION 8

3aα,4,7,7aα-tetrahydro-1α,3α-indanediol (3A) and racemic 3aα,4,7,7aα-tetrahydro-1α,3β-indanediol (3B)

A solution of 20.0 g. of 1aα,4,7,7aα-tetrahydro-1,3-indanedione in 150 ml. of absolute ethanol was added to a solution of 10.0 g. of lithium wire in 1000 ml. of liquid ammonia and stirred until the blue color disappeared. The mixture was heated on the steam bath and the ammonia was evaporated under a stream of air leaving a residue. The thus-obtained residue was taken up in 1000 ml. of ethyl acetate and 500 ml. of water. The ethyl acetate layer was separated and washed twice with 500-ml. portions of water, then the ethyl acetate was removed by evaporation in vacuo under diminished pressure to give a colorless oil. The thus-obtained oil was dissolved in 250 ml. of absolute ether and 5.0 g. of lithium aluminum hydride was added. The mixture was stirred at room temperature for 1.5 hours, then excess lithium aluminum hydride was destroyed by addition first of ethyl acetate and then saturated aqueous sodium sulfate. The organic layer was separated by decantation and filtered. Addition of methylene chloride and Skellysolve B caused precipitation of crystals. The solvent was removed from the entire mixture by evaporation under diminished pressure giving 16.38 g. of a crystalline residue comprising 3aα,4,7,7aα-tetrahydro-1α,3α-indanediol and racemic 3aα,4,7,7aα-tetrahydro-1α,3β-indanediol.

PREPARATION 9

3aα,4,7,7aα-tetrahydro-1α,3α-indanediol dibenzoate (4A) and racemic 3aα,4,7,7aα-tetrahydro-1α,3β-indanediol dibenzoate (4B)

A solution of 7.5 g. of a mixture of 3aα,4,7,7aα-tetrahydro-1α,3α-indanediol and racemic 3aα,4,7,7aα-tetrahydro-1α,3β-indanediol in 100 ml. of pyridine was cooled in an ice bath and 16 ml. of benzoyl chloride was added with stirring. The mixture was allowed to stir about 18 hours while the temperature rose gradually to room temperature. The mixture was then poured into ice and water and neutralized with saturated aqueous sodium bicarbonate. The resulting mixture was extracted with methylene chloride and the methylene chloride extract was separated and washed first with dilute hydrochloric acid then with saturated aqueous sodium bicarbonate. The methylene chloride solution was evaporated to give a residue comprising 3aα,4,7,7aα-tetrahydro-1α,3α-indanediol dibenzoate and racemic 3aα,4,7,7aα-tetrahydro-1α,3β-indanediol dibenzoate which was dissolved in Skellysolve B and chromatographed over Florisil. On elution with 1% acetone in Skellysolve B the first three product-containing fractions gave partially crystalline residues. These were triturated with methanol, then recrystallized from methanol to give 1.73 g. of racemic 3aα,4,7,7aα-tetrahydro-1α,3β-indanediol dibenzoate having a melting point of 88°–89° C., infrared absorption maxima in Nujol at 1710, 1600, 1585, 1115, 1070, 1050, and 710 cm$^{-1}$., and the following analysis:

Calcd. for $C_{25}H_{22}O_4$: C, 76.22; H, 6.12. Found: C, 76.17; H, 6.27.

Nuclear magnetic resonance analysis showed that this compound was the trans dibenzoate.

The mother liquors from the above trituration-recrystallization of the trans dibenzoate were combined with the remaining product containing fractions from the above chromatogram and the solvents were removed by evaporation, giving a residue which was chromatographed over Florisil and eluted in 20 fractions with a gradient of 0 to 1% acetone in Skellysolve B. Fractions 10–15 were combined to give 5.911 g. of residue which on trituration with methanol in a dry-ice bath gave 1.76 g. of racemic 3aα,4,7,7aα-tetrahydro-1α,3β-indanediol dibenzoate having a melting point of 80°–86° C. Fractions 16–20 were combined to give 1.76 g. of residue comprising 3aα,4,7,7aα-tetrahydro-1α,3α-indanediol dibenzoate. Fraction 18 was shown by nuclear magnetic resonance analysis to be pure cis dibenzoate.

PREPARATION 10

3aα,4,7,7aα-tetrahydro-1α,3αindanediol dibenzoate (4A) and racemic 3aα,4,7,7aα-tetrahydro-1α,3β-indanediol dibenzoate (4B)

A solution of 44.4 g. of a mixture of 3aα,4,7,7aα-tetrahydroindane-1α,3α-diol and racemic 3aα,4,7,7aα-tetrahydroindane-1α,3β-diol in 600 ml. of pyridine was cooled in an ice bath and 120 ml. of benzoyl chloride was added dropwise with stirring. The ice bath was removed and the mixture was stirred at room temperature for 5½ hours. The mixture was then diluted with 2000 ml. of methylene chloride and washed with 1500 ml. of a mixture of 1 vol. of concentrated hydrochloric acid to 1 volume of water. The aqueous wash was rewashed with about 500 ml. of methylene chloride. The methylene chloride solutions were combined and washed with saturated aqueous sodium bicarbonate and then with water. The thus-obtained methylene chloride solution was poured onto a 700 g. Florisil column and eluted with 5000 ml. of methylene chloride. The methylene chloride eluates were concentrated to a sirupy residue by evaporation under diminished pressure. The above residue was dissolved in 500 ml. of methanol and filtered through a sintered glass funnel. The mixture was cooled by evaporation under a stream of air and seeded with racemic 3aα,4,7,7aα-tetrahydro-1α,3β-indanediol dibenzoate. The trans dibenzoate separated by crystallization and was removed by filtration. The filtrate was again cooled under a stream of air and seeded, and the above procedure was repeated until no more crystals were obtained. By this process 49.5 g. of racemic 3aα,4,7,7aα-tetrahydroindane-1α,3β-diol dibenzoate having a melting point of 78°–82° C. was obtained. The methanol was then removed from the filtrate by evaporation under diminished pressure to yield a 64.5 g. sirup comprising 3aα,4,7,7aα-tetrahydroindane-1α,3α-diol dibenzoate.

PREPARATION 11

Racemic 3aα,6,7,7aα-tetrahydro-1α,3α-dihydroxy-5(4H)-indanone dibenzoate (5A)

A solution of 7.29 g. of crude 3aα,4,7,7aα-tetrahydro-1α,3α-indanediol dibenzoate (shown by vapor phase chromatography to be 75% 1α,3α-diol dibenzoate and 25% 1α,3β-diol dibenzoate) in 75 ml. of absolute ether was cooled in an ice bath and 8 ml. of a 1.9 molar solution of diborane in tetrahydrofuran was added. The mixture was stirred for an hour and then the excess hydride was decomposed by addition of water. A mixture of 6.4 ml. of concentrated sulfuric acid, 8.0 g. of sodium dichromate and 30 ml. of water was added cautiously and the resulting mixture was stirred for about 18 hours at room temperature. The ether layer was separated and the aqueous layer was extracted with ether and methylene chloride. The ether layer and extracts were combined, washed with saturated aqueous sodium bicarbonate and then with water, and evaporated to give a residue which was chromatographed over Florisil and eluted with 5% and 10% acetone in Skellysolve B. The 5% acetone eluates were evaporated to give 0.31 g. of racemic 3aα,6,7,7aα-tetrahydro-1β,3α-dihydroxy-5(4H)indanone dibenzoate having a melting point of 137°–142° C.

The 10% acetone eluates of the above chromatogram were combined and evaporated to give 3.164 g. of a residue which on crystallization from ether gave 2.05 g. of racemic 3aα,6,7,7aα-tetrahydro-1α,3α-dihydroxy-5[4H]-indanone dibenzoate having a melting point of 108°–112° C., infrared absorption maxima at 3060, 3050, 1710, 1605, 1505, 1470, 1280, 1113 and 705 cm$^{-1}$.

PREPARATION 12

Racemic 3aα,6,7,7aα-tetrahydro-1α,3α-dihydroxy-5(4H)-indanone dibenzoate (5A)

A. Racemic 3aα,4,7,7aα-tetrahydro-1α-hydroxy-3-indanone (2)

A solution of 20 g. of 3aα,4,7,7aα-tetrahydro-1,3-indanedione in 150 ml. of absolute ether was added to a solution of 10 g. of lithium in 1000 ml. of liquid ammonia. The blue colored mixture was stirred until the color disappeared, then the ammonia was evaporated under a stream of air while heating on a steam bath and 1000 ml. of ethyl acetate was added, followed by 500 ml. of water. The ethyl acetate layer was separated and washed twice with 500 ml. portions of water, then the ethyl acetate was removed by evaporation leaving a residue comprising racemic 3aα,4,7,7aα-tetrahydro-1α-hydroxy-3-indanone.

B. 3aα,4,7,7aα-tetrahydro-1α,3α-indanediol (3A) and racemic 3aα,4,7,7aα-tetrahydro-1α,3β-indanediol (3B)

The residue of racemic 3aα,4,7,7aα-tetrahydro-1α-hydroxy-3-indanone (from A, above) was dissolved in 250 ml. of absolute ether and excess lithium aluminum hydride was added with stirring. The resulting mixture was stirred at room temperature for 1.5 hours then the excess hydride was decomposed by adding first ethyl acetate then saturated aqueous sodium sulfate. The mixture was filtered and the ether layer was separated. The ether was removed by evaporation and methylene chloride and Skellysolve B were added, resulting in crystallization of the residue. The solvents were removed by evaporation under diminished pressure to give 16.38 g. of crystalline residue comprising a mixture of 3aα,4,7,7aα-tetrahydro-1α,3α-indanediol and racemic 3aα,4,7,7aα-tetrahydro-1α,3β-indanediol.

C. 3aα,4,7,7aα-tetrahydro-1α,3αindanediol dibenzoate (4A) and racemic 3aα,4,7,7aα-tetrahydro-1α,3β-indanediol dibenzoate (4B)

A mixture of 30.2 g. of crude 3aα,4,7,7aα-tetrahydro-1α,3α-indanediol and racemic 3aα,4,7,7aα-tetrahydro-1α,3β-indanediol (prepared in two runs as in B, above) was dissolved in 225 ml. of pyridine and cooled in an ice bath, then 60 ml. of benzoyl chloride was added slowly with stirring. The reaction mixture was then stirred for about 18 hours at room temperature, then was diluted with methylene chloride and washed with water. The methylene chloride layer was separated and the aqueous layer extracted with methylene chloride. The methylene chloride extracts were combined and washed with saturated aqueous sodium bicarbonate, then with dilute ice cold hydrochloric acid and again with aqueous saturated sodium bicarbonate. The methylene chloride was removed by evaporation and the residual syrup was dissolved in methylene chloride and passed over a 200 g. Florisil column. The column was eluted with 2000 ml. of methylene chloride and the solvent was removed from the eluate by evaporation under diminished pressure to yield 78 g. of a mixture comprising 3aα,4,7,7aα-tetrahydro-1α,3αindanediol dibenzoate and racemic 3aα,4,7,7aα-tetrahydro-1α,3β-indanediol dibenzoate.

D. Racemic 3aα,6,7,7aα-tetrahydro-1α,3α-dihydroxy-5(4H)-indanone dibenzoate (5A) and racemic 3aα,6,7,7aα-tetrahydro-1β,3αdihydroxy-5(4H)-indanone dibenzoate (5B)

A solution of 78 g. of a mixture of crude 3aα,4,7,-7,aα-tetrahydro-1α,3α-indanediol dibenzoate and racemic 3aα,4,7,7aα,tetrahydro-1α,3β-indanediol dibenzoate (from C, above) in 800 ml. of absolute ether was cooled in an ice bath, and 100 ml. of a solution of 1.9 molar diborane in tetrahydrofuran was added. After 1.5 hours no excess hydride was present, and a further 30 ml. of 1.9 molar diborane solution was added. The mixture was then stirred for 4 hours at room temperature after which excess hydride was decomposed by the addition of water and an oxidizing mixture of 86 g. of sodium dichromate, 75 ml. of sulfuric acid and 400 ml. of water was added cautiously. The resulting mixture was stirred for about 18 hours at room temperature and the aqueous layer again extracted with ether. The ether extracts were combined and washed first with water and then with aqueous saturated sodium bicarbonate. The solvents were removed by evaporation and the residue was mixed with 300 ml. of ether and refrigerated to give 28.03 g. of crystalline product comprising a mixture of racemic 3aα,6,7,7aα-tetrahydro-1α,3α-dihydroxy-5(4H)-indanone dibenzoate and racemic 3aα,6,7,7aα-tetrahydro-1β,3α-dihydroxy-5(4H)-indanone dibenzoate having a melting point of 101°–102° C. Nuclear magnetic resonance analysis established that this product was 90% cis (1α,3α) isomer.

PREPARATION 13

Racemic 3aα,6,7,7aα-tetrahydro-1α,3α-dihydroxy-5(4H)-indanone dibenzoate (5A)

A solution of 112.5. g. of crude 3aα,4,7,7aα-tetrahydro-1α,3α-indanediol dibenzoate (prepared as in Preparation 10) in 1130 ml. of absolute ether and 110 ml. of tetrahydrofuran was stirred while the reaction system was flushed with nitrogen to remove air. Stirring was continued while diborane was passed in until an excess was present, as shown by bubbling when a drop of the reaction mixture was added to 1 ml. of water. Addition of the diborane required about 5 minutes. The reaction mixture was allowed to stand at room temperature for about 4.5 hours, then excess diborane was decomposed by dropwise addition of water. The mixture was then cooled in an ice bath and stirred while a mixture of 130 g. of sodium dichromate, 650 ml. of water, and 115 ml. of concentrated sulfuric acid was added cautiously, then stirring was continued at room temperature for about 18 hours. The organic layer was then separated and the aqueous layer was twice extracted with ether and once with methylene chloride. The organic layers were combined and washed with water, saturated aqueous sodium bicarbonate, and again with water. The solvent was removed by evaporation under diminished pressure yielding a light yellow syrup which was dissolved in about 400 ml. of absolute ether and refrigerated to allow crystallization. The crystals were separated by filtration to give 46.1 g. of racemic 3aα,6,7,7aα-tetrahydro-1α,3α-dihydroxy-5(4H)-indanone dibenzoate having a melting point of 100°–109° C.

PREPARATION 14

Racemic 3aα,4,5,6,7,7aα-hexahydro-5α-pentyl-1α,3α,5β-indanetriol (6B)

An ether solution of n-amyl magnesium bromide was prepared from 30 ml. of 1-bromopentane in 200 ml. of ether and 10 g. of magnesium, then 130 ml. of this Grignard solution was added to a solution of 11.5 g. of racemic 3aα,6,7,7aα-tetrahydro-1α,3α-dihydroxy-5(4H)-indanone dibenzoate in 80 ml. of benzene and the mixture was heated for one hour under reflux. Excess Grignard reagent was then decomposed by addition of water. Rochelle salts were added, then ether and tetrahydrofuran and the solid residue was removed by filtration. The solid residue was leached several times with boiling ethyl acetate. The leachings were combined and concentrated by evaporation to give a residue which was crystallized from ethyl acetate to give 3.14 g. of racemic 3aα,4,5,6,7,7aα-hexahydro-5α-pentyl-1α,3α,5β-indanetriol having a melting point of 165°–167° C. and infrared absorption maxima (Nujol solution) of 3300 and 1077 cm$^{-1}$.

Analysis: Calc'd for $C_{14}H_{26}O_3$: C, 69.38; H, 10.81. Found: C, 68.77; H, 10.81.

Nuclear magnetic resonance analysis showed the structure to be correct.

PREPARATION 15

Racemic 3aα,4,5,6,7,7,aα-hexahydro-5α-pentyl-1α,3α,5β-indanetriol (6B) and racemic 3aα,4,5,6,7,7aα-hexahydro-5β-pentyl-1α,3α,5α-indanetriol (6B)

A solution of n-amyl magnesium bromide was prepared by adding a solution of 273 ml. of 1-bromopentane in 500 ml. of absolute ether to a suspension of 53.5 g. of magnesium turnings in 400 ml. of absolute ether, and 120 ml. of this amyl magnesium bromide solution (1.88 M) was added dropwise with stirring to a solution of 10.08 g. of 3aα,6,7,7aα-tetrahydro-1α,3α-dihydroxy-5(4H)-indanone dibenzoate (prepared as in Preparation 13) in 75 ml. of benzene at room temperature. The mixture was then heated under reflux for 2 hours. The excess Grignard reagent was decomposed by addition of water until the inorganic material was a freely stirring white solid. The mixture was then diluted with 250 ml. of Skellysolve B mixed hexanes and the solids were removed by filtration. The solid fiter cake was leached with six 250-ml. portions of boiling ethyl acetate and the leachings were combined and evaporated to give 7.23 g. of crystalline residue comprising racemic 3aα,4,5,6,7,7aα-hexahydro-5α-pentyl-1α,3α,5β-idanetriol and racemic 3aα,4,5,6,7,7aα-hexahydro-5β-pentyl-1α,3α,5α-indanetriol. This residue was leached at room temperature with 250 ml. of Skellysolve B and filtered to give 4.53 g. of a crystalline mixture of racemic 3aα,4,5,6,7,7aα-hexahydro-5α-pentyl-1α,3α,5β-indanetriol and racemic 3aα,4,5,6,7,7aα-hexahydro-5β-pentyl-1α,3α,5α-indanetriol having a melting point of 162°–166° C. Further crystallization affords essentially pure racemic 3aα,4,5,6,7,7aα-hexahydro-5α-pentyl-1α,3α,5β-indanetriol. If desired, the combined mother liquors from the crystallizations can be chromatographed, e.g., over Florisil, to give additional quantities of the above racemic 3aα,4,5,6,7,7aα-hexahydro-5α-pentyl-1α,3α,5β-indanetriol as well as essentially purified fractions comprising the racemic 3aα,4,5,6,7,7aα-hexahydro-5β-pentyl-1α,3α,5α-indanetriol.

Following the procedure of Preparations 14 and 15 above, but replacing racemic 3aα,6,7,7aα-tetrahydro-1α,3α-dihydroxy-5(4H)-indanone dibenzoate as starting material with other 1,3-diacylates of racemic 3aα,6,7,7aα-tetrahydro-1α,3α-dihydroxy-5[4H]-indanone, e.g., the 1,3-diacetate, dipropionate, dibutyrate, dihexanoate, dilaurate, di(phenylacetate), di(phenylpropionate) and the like is productive of racemic 3aα,4,5,6,7,7aα-hexahydro-5α-pentyl-1α,3α,5β-indanetriol and racemic 3aα,4,5,6,7,7aα-hexahydro-5β-pentyl-1α,3α,5α-indanetriol.

Following the procedure of Preparations 14 and 15 above, but substituting other alkyl metal halides or dialkyl cadmium compounds for n-amyl magnesium bromide is productive of the corresponding racemic 3aα,4,5,6,7,7aα-hexahydro-5α (and 5β)-alkyl-1α,-3α,5β (and 5α)-indanetriol. For example, treating racemic 3aα,6,7,7aα-tetrahydro-1α,3α-dihydroxy-5(4H)-indanone dibenzoate (or other 1,3-diacylate) with methyl magnesium iodide, methyl lithium, diethyl cadmium, propyl cadmium bromide, isopropyl magnesium bromide, butyl magnesium iodide, butyl lithium, 2-butyl magnesium bromide, t-butyl magnesium bromide, 2-amyl magnesium bromide, 3-amyl magnesium bromide, hexyl magnesium iodide, 2-hexyl magnesium bromide, heptyl magnesium bromide, octyl magnesium bromide, 2-octyl magnesium bromide, 3-octyl magnesium bromide and phenyl magnesium bromide is productive of racemic 3aα,4,5,6,7,7aα-hexahydro-5α (and 5β)-methyl-1α,3α,5β (and 5α)-indanetriol, racemic 3aα,4,5,6,7,7aα-hexahydro-5α (and 5β)-ethyl-1α,-3α,5β (and 5α)-indanetriol, racemic 3aα,4,5,6,7,7aα-hexahydro-5α (and 5β)-propyl-1α,3α,5β (and 5α)-indanetriol, racemic 3aα,4,5,6,7,7aα-hexahydro-5α (and 5β)-isopropyl-1α,3α,5β-(and 5α)-indanetriol, racemic 3aα,4,5,6,7,7aα-hexahydro-5α(and 5β)-butyl-1α,3α,5β-(and 5α)-indanetriol, racemic 3aα,4,5,6,7,-,7aα-hexahydro-5α (and 5β)-(2-butyl)-1α,3α,5β(and 5α)-indanetroil, racemic 3aα,4,5,6,7,7aα-hexahydro-5α(and 5β)-t-butyl-1α,3α,5β-(and 5α)-indanetriol, racemic 3aα,4,5,6,7,7aα-hexahydro5α (and 5β)-(2-amyl)-1α,3α,5β-(and 5α)-indanetriol, racemic 3aα,4,5,6,7,7aα-hexahydro-5α (and 5β)-(3-amyl)-1α,-3α,5β-(and 5α)-indanetriol, racemic 3aα,4,5,6,7,7aα-hexahydro-5α (and 5β)-hexyl-1α,3α,5β-(and 5α)indanetriol, racemic 3aα,4,5,6,7,7aα-hexahydro-5α (and 5β)-(2-hexyl)-1α,3α,5β (and 5α)-indanetriol, racemic 3aα,4,5,6,7,7aα-hexahydro-5α (and 5β)-heptyl-1α,-3α,5β (and 5α)-indanetriol, racemic 3aα,4,5,6,7,7aα-hexahydro-5α(and 5β)-octyl-1α,3α,5β(and 5α)-indanetriol, racemic 3aα,4,5,6,7,7aα-hexahydro-5α(and 5β)-(2-octyl)-1α,3α,5β(and 5α)-indanetriol, racemic 3aα,4,5,6,7,7aα-hexahydro-5α(and 5β)-(3-octyl)-1α,3α,5β-(and 5α)-indanetriol and racemic 3aα,4,5,6,7,7aα-hexahydro-5α (and 5β)-phenyl-1α,-3α,5β(and 5α)-indanetriol.

PREPARATION 16 1α,3α-p-nitrobenzylidene derivative of racemic 3aα,6,7,7aα-tetrahydro-5-amyl-1α,3α-indanediol (7)

A mixture of 0.50 g. of racemic 3aα,4,5,6,7,7aα-hexahydro-5α-n-amyl-1α,3α,5β-indanetriol, 0.50 g. of p-nitrobenzaldehyde, 10 ml. of benzene, 10 ml. of xylene and 0.10 g. of p-toluenesulfonic acid was heated at reflux under a calcium carbide drying trap for 2.5 hours, thus accomplishing both dehydration and acetal formation, then was cooled and shaken first with aqueous saturated sodium bisulfite then with aqueous saturated sodium bicarbonate. The organic solution was separated and the solvent was removed by evaporation leaving a residue which was dissolved in Skellysolve B and chromatographed over Florisil then eluted with Skellysolve B containing acetone. The 3% acetone in Skellysolve B eluates contained 0.498 g. of the 1α,3α-p-nitrobenzylidene derivative of racemic 3aα,6,7,7aα-tetrahydro-5-amyl-1α,3α-indanediol which after crystallization from methanol melted at 49°–53° C. and had infrared absorption maxima (Nujol solution) at 3100, 3000, 1609, 1525, 1350, 1087, 1034, 745 and 692 cm$^{-1}$. The structure was confirmed by nuclear magnetic resonance analysis.

PREPARATION 17

1α,3α-p-nitrobenzylidene derivative of racemic 3aα,6,7,7aα-tetrahydro-5-amyl-1α,3α-indanediol (7)

A mixture of 16.9 g. of mixed racemic 3aα,4,5,6,7,-,7aα-hexahydro -5α-amyl-1α,3α,5β-indanetriol and racemic 3aα,4,5,6,7,7aα-hexhydro-5β-amyl-1α,3α,5α-indanetriol (prepared as in Preparation 15), 250 ml. of benzene, 250 ml. of p-xylene, 16.9 g. of p-nitrobenzaldehyde and 1.0 g. of p-toluenesulfonic acid was heated at reflux under a Dean Stark water trap and in an atmosphere of nitrogen for 3 hours. This accomplished both dehydration and acetal formation. The mixture was cooled and shaken with saturated aqueous sodium bisulfite, then the solids were removed by filtration and the aqueous and organic layers separated. The organic layer was again washed with saturated aqueous sodium bisulfite, then with saturated aqueous sodium bicarbonate and finally with water. The organic layer was evaporated under reduced pressure and the resulting residue was dissolved in methylene chloride and chromatographed over Florisil. Elution was with 1% acetone in Skellysolve B. The eluates were evaporated and the crystalline residues were recrystallized by dissolving in ether and adding methanol. There was thus obtained a first crop of 14.02 g. of crystals comprising the 1α,3α-nitrobenzylidene derivative of racemic 3aα,6,7,7aα-tetrahydro-5-amyl-1α,3α-indanediol having a melting point of 54°–56° C. A further 2.41 g. was obtained by removing the solvent from the mother liquors.

Following the procedure of Preparations 16 and 17 but replacing 3aα,4,5,6,7,7aα-hexahydro-5α(and 5β)-amyl-1α,3α,5β-(and 5α)-indanetriol with other 3aα,4,5,6,7,7aα-hexahydro-5α(and 5β)-alkyl-1α,-3α,5β-(and 5α)-indanetriols, for example those named following Example 18 is productive of the 1α,3α-p-nitrobenzylidene derivative of the corresponding racemic 3aα,6,7,7aα-tetrahydro-5-alkyl-1α,3α-indanediol.

Following the procedure of Preparations 16 and 17 but replacing p-nitrobenzaldehyde with other aldehydes such as formaldehyde, acetaldehyde, propionaldehyde, chloral, p-bromobenzaldehyde, p-chlorobenzaldehyde, p-fluorobenzaldehyde, 2,4,6-trichlorobenzaldehyde and p-carbomethoxybenzaldehyde is productive of the corresponding racemic 1α,3α-acetal of 3aα,6,7,7aα-tetrahydro-5-amyl-1α,3α-indanediol. Similarly, following the procedure of Examples 19 and 20 but replacing p-nitrobenzaldhyde with other aldehydes such as those mentioned above and replacing racemic 3aα,4,5,6,7,7aα-hexahydro-5α(and 5β)-amyl-1α,-3α,5β(and 5α)-indanetriol with another racemic 3aα,4,5,6,7,7aα-hexahydro-5α(and 5β)-alkyl-1α,-3α,5β(and 5α)-indanetriol, for example, one named following Preparation 15 is productive of the corresponding racemic 1α,3α-acetal of racemic 3aα,6,7,-,7aα-tetrahydro-5-alkyl-1α,3α-indanediol.

PREPARATION 18

1α,3α-p-nitrobenzylidene derivative of racemic 3aα,4,5,6,7,7aα-hexahydro-5β-amyl-1α,3α,4α,5α-indanetetrol (8)

A solution of 0.55 g. of the p-nitrobenzylidene derivative of 3aα,6,7,7aα-tetrahydro-5-amyl-1α,3α-indanediol and 0.44 g. of osmium tetroxide in 25 ml. of absolute ether was stirred at room temperature for about 18 hours, then the mixture was diluted with 25 ml. of tetrahydrofuran and cooled in an ice bath while gaseous hydrogen sulfide was bubbled through for 5 minutes. The solution was then filtered and the solvent was removed from the filtrate by evaporation under diminished pressure giving 0.435 g. of a crystalline residue which was recrystallized from a mixture of ether and Skellysolve B to give 0.106 g. of the 1α,3α-p-nitrobenzylidene derivative of racemic 3aα,4,5,6,7,7aα-hexahydro-5β-amyl-1α,3α,4α,5α-indanetetrol having a melting point of 167°–170° C. A further crystallization from acetone gave an analytical sample of the 1α,3α-p-nitrobenzylidene derivative of racemic 3aα,4,5,6,7,7aα-hexahydro-5β-amyl-1α,3α,4α,5α-indanetetrol having a melting point of 170°–175° C.

Analysis: Calc'd for $C_{21}H_{29}O_6N$: C, 64.43; H, 7.47; N, 3.58. Found: C, 64.10; H, 7.94; N, 3.58.

The structure was confirmed by nuclear magnetic resonance analysis.

PREPARATION 19

1α,3α-p-nitrobenzylidene derivative of racemic 3aα,4,5,6,7,7aα-hexahydro-5β-amyl-1α,3α,4α,5α-indanetetraol (8) and 1α,3α-p-nitrobenzylidene derivative of racemic 3aα,4,5,6,7,7aα-hexahydro-5α-amyl-1α,3α,4β,5β-indanetetraol (8)

A solution of 14.02 g. of the 1α,3α-p-nitrobenzylidene derivative of racemic 3aα,6,7,7aα-tetrahydro-5-amyl-1α,3α-indanediol (prepared as in Preparation 17) in 400 ml. of absolute ether was cooled in an ice bath and 12.3 g. of osmium tetroxide was added with stirring. The mixture was stirred for about 18 hours while the temperature rose gradually to room temperature. Hydrogen sulfide was then bubbled through the mixture for 10 minutes. The mixture was filtered through Celite (diatomaceous earth filter aid) and the solvent was removed from the filtrate by evaporation under diminished pressure leaving 10.75 g. of residue comprising a mixture of the 1α,3α-p-nitrobenzylidene derivative of racemic 3aα,4,5,6,7,7aα-hexahydro-5β-amyl-1α,3α,4α,5α-indanetetrol and the 1α,3α-p-nitrobenzylidene derivative of racemic 3aα,4,5,6,7,7aα-hexahydrp-5α-amyl-1α,3α,4β,5β-indanetetrol. This residue was recrystallized from a mixture of acetone and Skellysolve B to give 1.22 g. of crude 1α,3α-p-nitrobenzylidene derivative of racemic 3aα,4,5,6,7,7aα-hexahydro-5β-amyl-1α,3α,4β,5α-indanetetrol having a melting point of 163°–166° C. The mother liquors from this crystallization were chromatographed over Florisil and eluted with Skellysolve B containing 10 to 20% acetone to give 4.66 g. of crystalline product comprising the 1α,3α-nitrobenzylidene derivative of racemic 3aα,4,5,6,7,7aα-hexahydro-5α-amyl-1α,3α,4β,5β-indanetetrol having a melting point of 30°–40° C. On recrystallization from a mixture of ether and Skellysolve B an analytical sample of the 5α-amyl compound was obtained having a melting point of 41°–44° C.

PREPARATION 20

1α,3α-p-nitrobenzylidene derivative of racemic 3aα,4,5,6,7,7aα-hexahydro-5β-amyl-1α,3α,4α,5α-indanetetrol (8) and 1α,3α-p-nitrobenzylidene derivative of racemic 3aα,4,5,6,7,7aα-hexahydro-5α-amyl-1α,3α,4β,5β-indanetetraol (8)

A solution of 1.00 g. of the 1α,3α-p-nitrobenzylidene derivative of racemic 3aα,6,7,7aα-tetrahydro-5-amyl-1α,3α-indanediol in 50 ml. of tetrahydrofuran was stirred while 25 mg. of osmium tetroxide was added. A solution of 0.60 g. of sodium metaperiodate in 10 ml. of water was then added, followed by 0.60 g. of sodium acetate. The resulting mixture was heated under reflux with constant stirring for 24 hours, then it was concentrated to about a half volume by distillation under reduced pressure. The residual mixture was cooled, diluted with an equal volume of water, and extracted three times with methylene chloride. The methylene cholride extracts were combined, washed with aqueous sodium sulfite, dried over sodium sulfate, and evaporated under reduced pressure to yield a residue which was crystallized from a mixture of acetone and Skellysolve B to give 0.30 g. of the 1α,3α-p-nitrobenzylidene derivative of racemic 3aα,4,5,6,7,7aα-hexahydro-5β-amyl-1α,3α,4α,5α-indanetetrol having a melting point of 155°–162° C. The mother liquors from the above crystallization were concentrated to dryness, dissolved in a minimum volume of a mixture of 30% ethyl acetate and 70% cyclohexane, and placed on a 75 g. column of silica gel. The column was eluted with 25 ml. portions of the same solvent mixture. Fractions 2–4 contained 300 mg. of unreacted starting material. Fractions 11–20 contained 336 mg. of a mixture of the 1α,3α-p-nitrobenzylidene derivative of racemic 3aα,4,5,6,7,7aα-hexahydro-5β-amyl-1α,3α,4α,5α-indanetetrol and the 1α,3α-p-nitrobenzylidene derivative of racemic 3aα,4,5,6,7,7aα-hexahydro-5α,amyl-1α,3α,4β,5β-indanetetrol.

Following the procedure of Preparations 18, 19 and 20 but substituting for the 1α,3α-nitrobenzylidene derivative of racemic 3aα,6,7,7aα-tetrahydro-5-amyl-1α,3α-indanediol as starting material other 5-alkyl indanediols, e.g., the 1α,3α-p-nitrobenzylidene derivative of racemic 3aα,6,7,7aα-tetrahydro-5-alkyl-1α,3α-indanediol wherein the alkyl group is methyl, ethyl, propyl, isopropyl, butyl, 2-butyl, t-butyl, 2-amyl, 3-amyl, hexyl, 2-hexyl, heptyl, octyl, 2octyl, 3-octyl, and the like is productive of the corresponding 1α,3α-p-nitrobenzylidene derivative of racemic 3aα,4,5,6,7,7aα-hexahydro-5β-alkyl1α,3α,4α,5α-indanetetrol and the 1α,3α-p-nitrobenzylidene derivative of racemic 3aα,4,5,6,7,7aα-hexahydro-5α-alkyl1α,3α,4β,5β-indanetetrol.

Following the procedures of Preparations 18, 19 and 20 but substituting for the 1α,3α-p-nitrobenzylidene derivative of racemic 3aα,6,7,7aα-tetrahydro-5-alkyl-1α,3α-indanediol other 1α,3α-acetals of racemic 3aα,6,7,7aα-tetrahydro-5-alkyl-1α,3α-indanediol wherein the acetal group is derived from, for example, formaldehyde, acetaldehyde, propionaldehyde, chloral, p-bromobenzaldehyde, p-chlorobenzaldehyde, p-fluorobenzaldehyde, 2,4,6-trichlorobenzaldehyde, p-carbomethoxybenzaldehyde and the like is productive of the corresponding 1α,3α-acetals of racemic 3aα,4,5,6,7,7aα-hexahydro-5β-alkyl-1α,3α, 4α, 5α-indanetetrol and of racemic 3aα,4,5,6,7,7aα-hexahydro-5α-alkyl-1α,3α,4β,5β-indanetetrol.

PREPARATION 21

3α,5α-p-nitrobenzylidene derivative of racemic 3α,5α-dihydroxy-2β-(3-oxooctyl)cyclopentane-1β-carboxaldehyde (9A)

A mixture of 0.05 g. of lead tetraacetate and 10 ml. of benzene was added to a mixture of 0.15 g. of the p-nitrobenzylidene derivative of racemic 3aα,4,5,6,7-

,7aα-hexahydro-5β-amyl-1α,3α,4α,5α-indanetetrol in 10 ml. of benzene, then 15 ml. of toluene was added. After stirring at room temperature for one hour, saturated aqueous sodium thiosulfate was added and the organic layer was separated and filtered through Celite (diatomaceous filter aid). The solvent was removed from the filtrate by evaporation under diminished pressure to yield 0.147 g. of a colorless viscous oil comprising the 3α,5α-p-nitrobenzylidene derivative of racemic 3α,5α-dihydroxy-2β-(3-oxooctyl)cyclopentane-1β-carboxaldehyde. The structure was confirmed by nuclear magnetic resonance analysis.

PREPARATION 22

3α,5α-p-nitrobenzylidene derivative of racemic 3α,5α-dihydroxy-2β-(3-oxooctyl)cyclopentane-1β-carboxaldehyde. (9A)

A suspension of 0.5 g. of a mixture comprising the 1α,3α-p-nitrobenzylidene derivative of racemic 3aα,4,5,6,7,7aα-hexahydro-5β-amyl-1α,3α,4α,5α-indanetetrol and the 1α,3α-p-nitrobenzylidene derivative of racemic 3aα,4,5,6,7,7aα-hexahydro-5α-amyl-1α,3α,4β,5β-indanetetrol (prepared as in Preparation 19) in 50 ml. of benzene was stirred at room temperature and 1.5 g. of lead tetraacetate was added. Stirring was continued for two hours then 10 ml. of ether and about 10 ml. of water was added. The mixture was filtered through Celite and the organic layer was separated, washed twice with water, and evaporated under diminished pressure to give 0.465 g. of the 3α,5α-p-nitrobenzylidene derivative of racemic 3α,5α-dihydroxy-2β-(3-oxooctyl)cyclopentane-1β-carboxaldehyde. The structure was confirmed by infrared absorption analysis.

Following the procedure of Preparations 21 and 22 but substituting for the 1α,3α-p-nitrobenzylidene derivative of racemic 3aα,4,5,6,7,7aα-hexahydro-5β(and 5α)-amyl-1α,3α,4α,(and 4β), 5α(and 5β)-indanetetrol as starting material the 1α,3α-p-nitrobenzylidene derivative of racemic 3aα,4,5,6,7,7aα-hexahydro-5β(and 5α)-alkyl-1α,3α,4α(and 4β),5α(and 5β)-indanetetrol in which the alkyl group is, for example, methyl, ethyl, propyl, isopropyl, butyl, 2-butyl, t-butyl, 2amyl, 3-amyl, hexyl, 2-hexyl, heptyl, octyl, 2-octyl and 3-octyl is productive of the 3α,5α-p-nitrobenzylidene derivative of the corresponding racemic 3α,5α-dihydroxy-2β-(3-oxoalkyl)cyclopentane-1β-carboxaldehyde, e.g., the 3α,5α-p-nitrobenzylidene derivative of racemic 3α,5α-dihydroxy-2β-(3-oxobutyl)cyclopentane-1β-carboxaldehyde, racemic 3α,5α-dihydroxy-2β-(3-oxohexyl)cyclopentane-1β-carboxaldehyde, racemic 3α,5α-dihydroxy-2β-(3-oxo-4-methylpentyl)cyclopentane-1β-carboxaldehyde, racemic 3α,5α-dihydroxy-2β-(3-oxoheptyl)cyclopentane-1β-carboxaldehyde, racemic 3α,5α-dihydroxy-2β-(3-oxo-4-methylhexyl)-cyclopentane-1β-carboxaldehyde, racemic 3α,5α-dihydroxy-2β-(3-oxo-4,4-dimethylpentyl)-cyclopentane-1β-carboxaldehyde, racemic 3α,5α-dihydroxy-2β-(3-oxo-4-methylheptyl)cyclopentane-1β-carboxaldehyde, racemic 3α,5α-dihydroxy-2β-(3-oxo-4-ethylhexyl)cyclopentane-1β-carboxaldehyde, racemic 3α,5α-dihydroxy-2β-(3-oxononyl)cyclopentane-1β-carboxaldehyde, racemic 3α,5α-dihydroxy-2β-(3-oxo-4-methyloctyl)cyclopentane-1β-carboxaldehyde, racemic 3α,5α-dihydroxy-2β-(3-oxodecyl)cyclopentane-1β-carboxaldehyde, racemic 3α,5α-dihydroxy-2β-(3-oxoundecyl)cyclopentane-1β-carboxaldehyde, racemic 3α,5α-dihydroxy-2β-(3-oxo-4-methyldecyl)cyclopentane-1β-carboxaldehyde, and racemic 3α,5α-dihydroxy-2β-(3-oxo-4-ethylnonyl)cyclopentane-1β-carboxaldehyde, respectively.

Following the procedure of Preparations 21 and 22 but substituting for the 1α,3α-p-nitrobenzylidene derivative of racemic 3α,4,5,6,7,7aα-hexahydro-5β(and 5α)-amyl-1α,3α,4α(and 4β),5α(and 5β)-indanetetrol as starting material other 1α,3α-acetals of racemic 3aα,4,5,6,7,7aα-hexahydro-5β(and 5α)-amyl-1α,3α,-4α(and 4β),5α(and 5β)-indanetetrol wherein the acetal group is derived from, e.g., formaldehyde, acetaldehyde, propionaldehyde, chloral, p-bromobenzaldehyde, p-chlorobenzaldehyde, p-fluorobenzaldehyde, 2,4,6-trichlorobenzaldehyde, p-carbomethoxybenzaldehyde and the like is productive of the corresponding 3α,5α-acetals of racemic 3α5α-dihydroxy-2β-(3-oxooctyl)-cyclopentane-1β-carboxaldehyde.

Following the procedure of Preparations 21 and 22 but substituting for the 1α,3α-p-nitrobenzylidene derivative of racemic 3aα,4,5,6,7,7aα-hexahydro-5β(and 5α)-amyl-1α,3α,4α(and 4β),5α(and 5β)-indanetetrol as starting material other 1α,3α-acetals of racemic 3aα,4,5,6,7,7aα-hexahydro-5β(and 5α)-alkyl-1α,3α,-4α(and 4β),5α(and 5β)-indanetetrol is productive of the corresponding 3α,5α-acetals of racemic 3α,5α-dihydroxy-2β-(3-oxoalkyl)cyclopentane-1β-carboxaldehyde.

PREPARATION 23

3α,5α-p-nitrobenzylidene derivative of racemic ethyl trans-[3α,5α-dihydroxy-2β-(3-oxooctyl)cyclopent-1β-yl] acrylate (10A)

A mixture of 3.00 g. of a mixture of the 1α,3α-p-nitrobenzylidene derivative of racemic 3aα,4,5,6,7-,7aα-hexahydro-5β-amyl-1α,3α,4α,5α-indanetetrol and the 1α,3α-p-nitrobenzylidene derivative of racemic 3aα,4,5,6,7,7aα-hexahydro-5α-amyl-1α,3α,4β,5β-indanetetrol, 250 ml. of benzene and 9.0 g. of lead tetraacetate was stirred for one hour at room temperature. The mixture was then diluted with ether and water and filtered through Celite (diatomaceous earth). The filtrate was washed twice with water, and the solvent removed by evaporation at room temperature under reduced pressure to give 2.46 g. of the 3α,5α-p-nitrobenzylidene derivative of racemic 3α,5α-dihydroxy-2β-(3-oxooctyl)cyclopentane-1β-carboxaldehyde as an oil.

The thus-obtained aldehyde was dissolved in 150 ml. of methylene chloride and the solution was cooled in an ice bath, then 6.00 g. of carbethoxymethylenetriphenylphosphorane was added the mixture was allowed to warm to room temperature. Stirring was continued for about 70 hours then the solvent was removed by evaporation under diminished pressure and the thus-obtained residue comprising the 3α,5α-p-nitrobenzylidene derivative of racemic ethyl trans-[3α,5α-dihydroxy-2β-(3-oxooctyl)cyclopent-1β-yl] acrylate was chromatographed over Florisil. The 8% acetone in Skellysolve B eluates where evaporated to give 2.152 g. of crystalline 3α,5α-p-nitrobenzylidene derivative of racemic ethyl trans-[3α,5α-dihydroxy-2β-(3-oxooctyl)cyclpent-1β-yl] acrylate which after recrystallization from a mixture of ether and Skellysolve B had a melting point of 58°–60° C., infrared absorption maxima (Nujol solution) at 1710, 1650, 1610, 1520, 1350, 1220, 1180, 1170, 1115, 1080, 1040, 1000, 855, 850, and 755 cm$^{-1}$. and the following analysis:

Analysis: Cal'd for $C_{25}H_{33}O_7N$: C, 65.34; H, 7.24; N, 3.05. Found: C, 65.33; H, 7.30; N, 3.34.

PREPARATION 24

3α,5α-p-nitrobenzylidene derivative of racemic ethyl trans-[3α,5α-dihydroxy-2β-(3-oxooctyl)cyclopent-1β-yl] acrylate (10A)

A solution of 0.465 g. of the 3α,5α-p-nitrobenzylidene derivative of racemic 3α,5α-dihydroxy-2β-(3-oxooctyl)cyclopentane-1β-carboxaldehyde (prepared as in Preparation 22) in 25 ml. of methylene chloride was cooled in an ice bath and 0.80 g. of carbethoxymethylenetriphenylphosphorane was added. The mixture was then allowed to stand for about 70 hours at room temperature and the solvent was removed by evaporation under diminished pressure. The thus-obtained residue was dissolved in 50 ml. of a mixture of 20% ethyl acetate in cyclohexane and filtered through 20 g. of silica gel. The silica gel was washed with an additional 200 ml. of 20% ethyl acetate in cyclohexane and the filtrate and washings together were evaporated under diminished pressure to give 0.433 g. of crystalline 3α,5α-p-nitrobenzylidene derivative of racemic ethyl trans-[3α,5α-dihydroxy-2β-(3-oxooctyl)cyclopent-1β-yl] acrylate which after recrystallization from a mixture of acetone and Skellysolve B had a melting point of 56°–58° C.

Following the procedures of Preparations 23 and 24, but substituting for the 3α,5α-p-nitrobenzylidene derivative of racemic 3α,5α-dihydroxy-2β-(3-oxooctyl)cyclopentane-1β-carboxaldehyde as starting material the 3α,5α-p-nitrobenzylidene derivative of a racemic 3α,5α-dihydroxy-2β-(3-oxoalkyl)cyclopentane-1β-carboxaldehyde, e.g., the 3α,5α-p-nitrobenzylidene derivative of racemic 3α,5α-dihydroxy-2β-(3-oxobutyl)cyclopentane-1β-carboxaldehyde or another 2β-(3-oxoalkyl) aldehyde named following Example 25 is productive of the 3α,5α-p-nitrobenzylidene derivative of the corresponding racemic ethyl trans-[3α,5α-dihydroxy-2β-(3-oxoalkyl)cyclopent-1β-yl] acrylate, e.g., the 3α,5α-p-nitrobenzylidene derivative of racemic ethyl trans-[3α,5α-dihydroxy-2β-(3-oxobutyl)cyclopent-1β-yl] acrylate.

Following the procedures of Preparations 23 and 24 but substituting for the 3α,5α-p-nitrobenzylidene derivative of racemic 3α,5α-dihydroxy-2β-(3-oxooctyl)cyclopentane-1β-carboxaldehyde as starting material other 3α,5α-acetals of racemic 3α,5α-dihydroxy-2β-(3-oxooctyl)cyclopentane-1β-carboxaldehyde wherein the acetal group is derived from, for example, formaldehyde, acetaldehyde, propionaldehyde, chloral, p-bromobenzaldehyde, p-fluorobenzaldehyde, p-carbomethoxybenzaldehyde, p-chlorobenzaldehyde, 2,4,6-trichlorobenzaldehyde and the like is productive of the corresponding 3α,5α-acetals of racemic ethyl trans-[3α,5α-dihydroxy-2β-(3-oxooctyl)cyclopent-1β-yl] acrylate.

Following the procedures of Preparations 23 and 24 but substituting for the 3α,5α-p-nitrobenzylidene derivative of racemic 3α,5α-dihydroxy-2β-(3-oxooctyl)cyclopentane-1β-carboxaldehyde as starting material other 3α,5α-acetals of racemic 3α,5α-dihydroxy-2β-(3-oxoalkyl)cyclopentane-1β-carboxaldehyde is productive of the corresponding 3α,5α-acetals of racemic ethyl trans-[3α,5α-dihydroxy-2β-(3-oxoalkyl)cyclopent-1β-yl] acrylate.

Substituting carbomethoxymethylenetriphenylphosphorane for carbethoxymethylenetriphenylphosphorane in Preparations 23 and 24 is productive of the corresponding methyl acrylates.

PREPARATION 25

3α,5α-p-nitrobenzylidene derivative of racemic methyl 5-[3α,5α-dihydroxy-2β-(3-oxooctyl)cyclopent-1β-yl]-2,4-pentadienoate (10A)

A. 3α,5α-p-nitrobenzylidene derivative of racemic 3α,5α-dihydroxy-2β-(3-oxooctyl)cyclopentane-1β-carboxaldehyde (9A)

A suspension of 5.00 g. (0.0128 mole) of a mixture of the 1α,3α-p-nitrobenzylidene derivative of racemic 3aα,4,5,6,7,7aα-hexahydro-5β-amyl-1α,3α,4α,5α-indanetetrol and the 1α,3α-p-nitrobenzylidene derivative of racemic 3aα,4,5,6,7,7aα-hexahydro-5α-amyl-1α,3α,4β,5β-indanetetrol in 25 ml. of acetic acid was stirred at room temperature and 6.8 g. of lead tetraacetate was added. The mixture was stirred for 5 minutes then 25 ml. of water and 25 ml. of benzene were added and the organic phase separated. The aqueous phase was washed twice more with benzene after which the combined organic layers were washed with water, dried, and evaporated under diminished pressure to give a residue comprising the 3α,5α-p-nitrobenzylidene derivative of racemic 3α,5α-dihydroxy-2β-(3-oxooctyl)cyclopentane-1β-carboxaldehyde.

B. Methylcrotylphosphorane (carbomethoxyallylidenetriphenylphosphorane)

A mixture of 5.74 g. (0.032 mole) of methyl 4-bromocrotonate, 8.83 g. of triphenylphosphine and 25 ml. of chloroform was stirred at 0° C. until a clear solution formed. The solution was allowed to stand 5 hrs. at room temperature, then 39 ml. of ice-cold aqueous 5% sodium hydroxide was added and the mixture was shaken for 10 minutes. The organic layer was then separated, washed with water, dried and evaporated under diminished pressure to give a dark orange oil consisting of the phosphorane from triphenylphosphine and methyl 4-bromocrotonate which crystallized on standing.

C. 3α,5α-p-nitrobenzylidene derivative of racemic methyl 5-[3α,5α-dihydroxy-2β-(3-oxooctyl)cyclopent-1β-yl]-2,4-pentadienoate (10A)

The crude 3α,5α-p-nitrobenzylidene derivative of racemic 3α,5α-dihydroxy-2β-(3-oxooctyl)cyclopentane-1β-carboxaldehyde obtained as in A, above, and the methyl crotyl phosphorane obtained as in B, above, were each dissolved in 10 to 15 ml. of chloroform, cooled in an ice bath, and then mixed under a nitrogen atmosphere. The resulting mixture was allowed to stand about 18 hrs. at 5° C., then was allowed to warm to room temperature and was poured onto a chromatographic column of 500 g. of Florisil. The column was eluted with 5000 ml. portions of Skellysolve B containing 2, 5, 5 and 7.5% acetone. The 5% acetone in Skellysolve B eluates were evaporated to give 3.6 g. of residue comprising the 3α,5α-p-nitrobenzylidene derivative of racemic methyl 5-[3α,5α-dihydroxy-2β-(3-oxooctyl)cyclopent-1β-yl]-2,4-pentadienoate which was further purified by chromatography over 180 g. of silica gel. Elution with a mixture of 20% ethyl acetate-80% cyclohexane gave 2.7 g. of product which after several crystallizations from methanol had a melting point of 88°–89° C., infrared absorption maxima at 1720, 1695, 1640, 1610, 1605, 1490, 1515, 1355, 1340, 1310, 1225, 1170, 1140, 1085, 1040, 1010, 1000, 855, 850, 750, and 745 cm$^{-1}$., and the following analysis:

Calc'd. for $C_{26}H_{33}O_7N$: C, 66.22; H, 7.05; N, 2.97. Found: C, 66.18; H, 6.91; N, 3.09.

Nuclear magnetic resonance analysis supported the proposed structure.

Following the procedure of Preparation 25 but substituting for the 3α,5α-p-nitrobenzylidene derivative of racemic 3α,5α-dihydroxy-2β-(3-oxooctyl)cyclopentane-1β-carboxaldehyde as starting material the 3α,5α-p-nitrobenzylidene derivative of a racemic 3α,5α-dihydroxy-2β-(3-oxoalkyl)cyclopentane-1β-carboxaldehyde, e.g., the 3α,5α-p-nitrobenzylidene derivative of racemic 3α,5α-dihydroxy-2β-(3-oxobutyl)cyclopentane-1β-carboxaldehyde or another 2β-(3-oxoalkyl)aldehyde named following Preparation 22 is productive of the 3α,5α-p-nitrobenzylidene derivative of the corresponding racemic methyl 5-[3α,5α-dihydroxy-2β-(3-oxoalkyl)cyclopent-1β-yl]-2,4-pentadienoate, for example, the 3α,5α-p-nitrobenzylidene derivative of racemic methyl 5-[3α,5α-dihydroxy-2β-(3-oxobutyl)-cyclopent-1β-yl]-2,4-pentadienoate.

Following the procedure of Preparation 25 but substituting for the 3α,5α-p-nitrobenzylidene derivative of racemic 3α,5α-dihydroxy-2β-(3-oxooctyl)cyclopentane-1β-carboxaldehyde as starting material other 3α,5α-acetals of racemic 3α,5α-dihydroxy-2β-(3-oxooctyl)cyclopentane-1β-carboxaldehyde wherein the acetal group is derived, for example, from formaldehyde, acetaldehyde, propionaldehyde, chloral, p-bromobenzaldehyde, p-chlorobenzaldehyde, p-fluorobenzaldehyde, p-carbomethoxybenzaldehyde, 2,4,6-trichlorobenzaldehyde and the like is productive of the corresponding 3α,5α-acetals of racemic methyl 5-[3α,5α-dihydroxy-2β-(3-oxooctyl)cyclopent-1β-yl]-2,4-pentadienoate.

Following the procedure of Preparation 25 but substituting for the 3α,5α-p-nitrobenzylidene derivative of racemic 3α,5α-dihydroxy-2β-(3-oxooctyl)cyclopentane-1β-carboxaldehyde as starting material another 3α,5α-acetal of a racemic 3α,5α-dihydroxy-2β-(3-oxoalkyl)cyclopentane-1β-carboxaldehyde is productive of the corresponding 3α,5α-acetal of racemic methyl 5-[3α,5α-dihydroxy-2β-(3-oxoalkyl)cyclopent-1β-yl]-2,4-pentadienoate.

Following the procedure of Preparation 25 but substituting ethyl 4-bromocrotonate for methyl 4-bromocrotonate is productive of the corresponding ethyl esters.

Preparation 26

3α,5α-p-nitrobenzylidene derivative of racemic ethyl 7-[3α,5α-dihydroxy-2β-(3-oxooctyl)cyclopent-1β-yl]-2,4,6-heptatrienoate (10A)

A. Ethylsorbylphosphorane solution

A solution of 15.0 g. of triphenylphosphine in 50 ml. of benzene was cooled in an ice bath and a solution of 12.1 g. of ethyl ω-bromosorbate in 25 ml. of benzene was added. The mixture was stirred at room temperature for about 72 hours, then was filtered to obtain a sticky solid which was washed with ether to obtain 12.3 g. of a granular solid comprising the triphenylphosphonium salt of ethyl ω-bromosorbate. A suspension of 4.00 g. of the thus obtained triphenylphosphonium salt of ω-bromosorbate in 200 ml. of methylene chloride was mixed with 100 ml. of water and the mixture was stirred until the solid dissolved. The mixture was then cooled in an ice bath and stirred under a nitrogen atmosphere while a solution of 0.32 g. of sodium hydroxide in 5 ml. of water was added dropwise. The organic phase became a deep red color. When addition was complete the organic phase was separated and washed four times with water until the washes were neutral to a pH test paper, giving a solution comprising ethylsorbylphosphorane in methylene chloride.

B. 3α,5α-p-nitrobenzylidene derivative of racemic 3α,5α-dihydroxy-2β-(3-oxooctyl)cyclopentane-1β-carboxaldehyde A suspension of 1.22 g. of a mixture comprising the 1α,3α-p-nitrobenzylidene derivative of racemic 3aα,4,5,6,7,7aα-hexahydro-5β-amyl-1α,3α,4α,5α-indanetetrol and the 1α,3α-p-nitrobenzylidene derivative of racemic 3aα,4,5,6,7,7aα-hexahydro-5α-amyl-1α,3α,4β,5β-indanetetrol in 150 ml. of benzene was cooled with an ice bath and stirred while adding 1.5 g. of lead tetraacetate. After stirring for 1 hour the ice bath was removed and the mixture was stirred for an additional hour at room temperature, then 50 ml. of water and 50 ml. of ether were added. The mixture was filtered through Celite (diatomaceous earth filter aid) and the organic phase was separated, washed twice with water, then evaporated to dryness under diminished pressure at room temperature to give 1.28 g. of a residue comprising the 3α,5α-p-nitrobenzylidene derivative of racemic 3α,5α-dihydroxy-2β-(3-oxooctyl)cyclopentane-1β-carboxaldehyde.

C. 3α,5α-p-nitrobenzylidene derivative of racemic ethyl 7-[3α,5α-dihydroxy-2-(3-oxooctyl)cyclopent-1β-yl]-2,4,6-heptatrienoate The 1.28 g. of the 3α,5α-p-nitrobenzylidene derivative of racemic 3α,5α-dihydroxy-2β-(3-oxooctyl)cyclopentane-1β-carboxaldehyde prepared as in B, above, was dissolved in 50 ml. of methylene chloride and one half of this solution was added drop-wise to the solution of ethylsorbylphosphorane in methylene chloride prepared as in A, above, while cooling in an ice bath. The mixture was stirred at room temperature for 3 days, then the solvent was removed by evaporation under diminished pressure. The residue was dissolved in 50 ml. of methylene chloride and chromatographed over silica gel and eluted with 5%, 10% and 20% ethyl acetate in cyclohexane. Following removal of a small amount of ethyl 7-(p-nitrophenyl)-hepta-2,4,6-trienoate with 10% ethyl acetate in cyclohexane, the 20% ethyl acetate in cyclohexane fractions were collected and evaporated to give 0.112 g. of a residue comprising the 3α,5α-p-nitrobenzylidene derivative of racemic ethyl 7-[3α,5α-dihydroxy-2-(3-oxooctyl)cyclopent-1β-yl]-2,4,6-heptatrienoate having an ultraviolet absorption maximum at 295 mμ. The structure was confirmed by infrared and nuclear magnetic resonance analyses.

PREPARATION 27

3α,5α-p-nitrobenzylidene derivative of racemic ethyl 7-[3α,5α-dihydroxy-2β-(3-oxooctyl)cyclopent-1β-yl]-2,4,6-heptatrienoate (10A)

A. 3α,5α-p-nitrobenzylidene derivative of racemic 3α,5α-dihydroxy-2β-(3-oxooctyl)-cyclopentane-1β-carboxaldehyde A suspension of 2.0 g. of a mixture of the 1α,3α-p-nitrobenzylidene derivative of racemic 3aα,4,5,6,7-

,7aα-hexahydro-5β-amyl-1α,3α,4α,5α-indanetetrol and the 1α,3α-p-nitrobenzylidene derivative of racemic 3aα,4,5,6,7,7aα-hexahydro-5α-amyl-1α,3α,4β,5β-indanetetrol in 18 ml. of acetic acid at room temperature was treated with stirring with 2.7 g. of dry lead tetraacetate. After 5 minutes water and benzene were added, then the benzene layer was separated, washed twice with water and evaporated under diminished pressure to give a residue comprising the 3α,5α-p-nitrobenzylidene derivative of racemic 3α,5α-dihydroxy-2β-(3-oxooctyl)-cyclopentane-1β-carboxaldehyde.

B. Ethylsorbylphosphorane (5-carboethoxy-2,4-pentadienylidenetriphenylphosphorane)

A mixture of 4.38 g. of ethyl ω-bromosorbate, 5.97 g. of triphenylphosphine and 25 ml. of chloroform was prepared with ice-bath cooling and was allowed to stand in the melting ice bath for about 24 hours, then the mixture was stirred vigorously under a nitrogen atmosphere and 25 ml. of cold aqueous 5% sodium hydroxide was added. Stirring was continued for 10 minutes. A deep orange-red organic phase separated, which was washed with water, dried, and concentrated by evaporation under diminished pressure to give an oil comprising ethylsorbylphosphorane.

C. 3α,5α-p-nitrobenzylidene derivative of racemic ethyl 7-[3α,5α-dihydroxy-2β-(3-oxooctyl)-cyclopent-1β-yl]-2,4,6-heptatrienoate (10A)

The 3α,5α-p-nitrobenzylidene derivative of racemic 3α,5α-dihydroxy-2β-(3-oxooctyl)cyclopentane-1β-carboxaldehyde, prepared as in part A, above, was dissolved in 25 ml. of methylene chloride and stirred under nitrogen while cooling in an ice-salt bath, then a solution of the ethylsorbylphosphorane, prepared as in part B, above, in 25 ml. of methylene chloride was added. The resulting mixture was stirred for 30 minutes, then was allowed to stand for about 18 hours at −10° C. The reaction mixture was then allowed to warm to room temperature and was poured onto a 200 g. of Florisil in a chromatograph column. The column was developed with 400-ml. portions of Skellysolve B containing increasing amounts of acetone. The first 3 fractions of 5% acetone in Skellysolve B contained triphenylphosphine. Development was continued with seven 5%-acetone and five 7.5%-acetone in Skellysolve B fractions. These were combined and evaporated to give 2.155 g. of a pale yellow gum comprising the 3α,5α-p-nitrobenzylidene derivative of racemic ethyl 7-[3α,5α-dihydroxy-2β-(3-oxooctyl)-cyclopent-1β-yl]-2,4,6-heptatrienoate. This was twice crystallized from methanol to give an analytical sample of the 3α,5α-p-nitrobenzylidene derivative of racemic ethyl 7-[3α,5α-dihydroxy-2β-(3-oxooctyl)cyclopent-1β-yl]2,4,6-heptatrienoate having a melting point of 92°–93° C., ultraviolet absorption peaks in ethanol of $\lambda_{max.} = 213$ mµ, $\epsilon = 11,800$ and $\lambda_{max.} = 302$ mµ, $\epsilon = 49,350$, I.R. absorption maxima at 1715, 1700, 1620, 1585, 1515, 1360, 1240, 1210, 1135, 1180, 1035, 1010, 845, 750 and 740 cm.$^{-1}$, and the following analysis:

Calc'd for $C_{29}H_{37}O_7N$: C, 68.08; H, 7.29; N, 2.74. Found: C, 68.30; H, 7.34; N, 2.74.

Following the procedure of Preparations 26 and 27, but substituting for the 3α,5α-p-nitrobenzylidene derivative of racemic 3α,5α-dihydroxy-2β-(3-oxooctyl)cyclopentane-1β-carboxaldehyde as starting material the 3α,5α-p-nitrobenzylidene derivative of a racemic 3α,5α-dihydroxy-2β-(3-oxoalkyl)-cyclopentane-1β-carboxaldehyde, e.g., the 3α,5α-p-nitrobenzylidene derivative of racemic 3α,5α-dihydroxy-2β-(3-oxobutyl)cyclopentane-1β-carboxaldehyde or another 2β-(3-oxoalkyl) analog named following Example 25 is productive of the 3α,5α-p-nitrobenzylidene derivative of the corresponding racemic ethyl 7-[3α,5α-dihydroxy-2β-(3-oxoalkyl)cyclopent-1β-yl]-hepta-2,4,6-trienoate, e.g., the 3α,5α-p-nitrobenzylidene derivative of racemic ethyl 7-[3α,5α-dihydroxy-2β-(3-oxobutyl)cyclopent-1β-yl]-hepta-2,4,6-trienoate.

Following the procedure of Preparations 26 and 27 but substituting for the 3α,5α-p-nitrobenzylidene derivative of racemic 3α,5α-dihydroxy-2β-(3-oxooctyl)cyclopentane-1β-carboxaldehyde as starting material other 3α,5α-acetals of racemic 3α,5α-dihydroxy-2β-(3-oxooctyl)cyclopentane-1β-carboxaldehyde wherein the acetal group is derived from, for example, formaldehyde, acetaldehyde, propionaldehyde, chloral, p-bromobenzaldehyde, p-chlorobenzaldehyde, p-fluorobenzaldehyde, p-carbomethoxybenzaldehyde, 2,4,6-trichlorobenzaldehyde and the like is productive of the corresponding 3α,5α-acetals of racemic ethyl 7-[3α,5α-dihydroxy-2β-(3-oxooctyl)cyclopent-1β-yl]-hepta-2,4,6-trienoate.

Following the procedure of Preparations 26 and 27 but substituting for the 3α,5α-p-nitrobenzylidene derivative of racemic 3α,5α-dihydroxy-2β-(3-oxooctyl)cyclopentane-1β-carboxaldehyde as starting material another 3α,5α-acetal of a racemic 3α,5α-dihydroxy-2β-(3-oxoalkyl)cyclopentane-1β-carboxaldehyde is productive of the corresponding 3α,5α-acetal of racemic ethyl 7-[3α,5α-dihydroxy-2β-(3-oxoalkyl)cyclopent-1β-yl]-hepta-2,4,6-trienoate.

Following the procedure of Preparations 26 and 27 but substituting for ethyl ω-bromosorbate other alkyl esters of ω-bromosorbic acid, for example, methyl ω-bromosorbate, is productive of the corresponding alkyl ester of formula 10A, for example, the 3α,5α-p-nitrobenzylidene derivative of racemic methyl 7-[3α,5α-dihydroxy-2β-(3-oxooctyl)cyclopent-1β-yl]-2,4,6-heptatrienoate.

PREPARATION 28

3α,5α-p-nitrobenzylidene derivative of racemic methyl 3-methyl-5-[3α,5α-dihydroxy-2β-(3-oxooctyl)cyclopent-1β-yl]-2,4-pentadienoate (10A)

Following the procedure of Preparation 25 but substituting methyl 3-methyl -4-bromo-2-butenoate for methyl bromocrotonate as starting material in part B is productive of the 3α,5α-p-nitrobenzylidene derivative of racemic methyl 3-methyl-5-[3α,5α-dihydroxy-2β-(3-oxooctyl)cyclopent-1β-yl]-2,4-pentadienoate.

Following the procedure of Preparation 25, parts B and C, but substituting methyl 3-methyl-4-bromo-2-butenoate for methyl bromocrotonate in part B and substituting for the 3α,5αp-nitrobenzylidene derivative of racemic 3α,5α-dihydroxy-2β-(3-oxooctyl)-cyclopentane-1β-carboxaldehyde in part C the 3α,5α-p-nitrobenzylidene derivative of a racemic 3α,5α-dihydroxy-2β-(3-oxoalkyl)-cyclopentane-1β-carboxaldehyde, e.g., the 3α,5α-p-nitrobenzylidene derivative of racemic 3α,5α-dihydroxy-2β-(3-oxobutyl)cyclopentane-1β-carboxaldehyde or another 2β-(3-oxoalkyl) aldehyde named following Example 25 is productive of the 3α,5α-p-nitrobenzylidene derivative of the corresponding racemic methyl 3-methyl-5-[3α,5α-dihydroxy-2β-(3-oxoalkyl)cyclopent-1β-yl]-2,4-pentadienoate, e.g., the 3α,5α-p-nitrobenzylidene derivative of racemic methyl 3-methyl-5-[3α,5α-dihydroxy-2β-(3-oxobutyl)cyclopent-1β-yl]-2,4-pentadienoate.

Following the procedure of Preparation 25, parts B and C, but substituting methyl 3-methyl-4-bromo-2-butenoate for methyl bromocrotonate in part B and substituting for the 3α,5α-p-nitrobenzylidene derivative of racemic 3α,5α-dihydroxy-2β-(3-oxooctyl)cyclopentane-1β-carboxaldehyde in part C other 3α,5α-acetals of racemic 3α,5α-dihydroxy-2β-(3-oxooctyl)-cyclopentane-1β-carboxaldehyde, wherein the acetal group is derived from, for example, formaldehyde, acetaldehyde, propionaldehyde, chloral, p-bromobenzaldehyde, p-chlorobenzaldehyde, p-fluorobenzaldehyde, p-carbomethoxybenzaldehyde, 2,4,6-trichlorobenzaldehyde, and the like is productive of the correponding 3α,5α-acetals of racemic methyl 3-methyl-5-[3α,5α-dihydroxy-2β-(3-oxooctyl)cyclopent-1β-yl]-2,4-pentadienoate.

Following the procedure of Preparation 25, parts B and C, but substituting methyl 3-methyl-4-bromo-2-butenoate for methyl bromocrotonate in part B and substituting for the 3α,5α-p-nitrobenzylidene derivative of racemic 3α,5α-dihydroxy-2β-(3-oxooctyl)cyclopentane-1β-carboxaldehyde in part C another 3α,-5α-acetal of a racemic 3α,5α-dihydroxy-2β-(3-oxoalkyl)cyclopentane-1β-carboxaldehyde is productive of the corresponding 3α,5α-acetal of racemic methyl 3-methyl-5-[3α,5α-dihydroxy-2β-(3-oxoalkyl)cyclopent-1β-yl]-2,4-pentadienoate.

Following the procedure of Preparation 25, parts B and C, but substituting an alkyl 3-methyl-4-bromo-2-butenoate, for example, ethyl 3-methyl-4-bromo-2-butenoate, for methyl bromocrotonate, is productive of the corresponding 3α,5α-p-nitrobenzylidene derivative of racemic alkyl 3-methyl-5-[3α,5α-dihydroxy-2β-(3-oxooctyl)cyclopent-1β-yl]-2,4-pentadienoate, for example, the 3α,5α-p-nitrobenzylidene derivative of racemic ethyl 3-methyl-5-[3α,5α-dihydroxy-2β-(3-oxooctyl)cyclopent-1β-yl]-2,4-pentadienoate.

PREPARATION 29

Racemic ethyl 7-[3α,5α-dihydroxy-2β-(3-oxooctyl)cyclopent-1β-yl]-hepta-2,4,6-trienoate (IB)

A mixture of 300 mg. of the 3α,5α-p-nitrobenzylidene derivative of ethyl 7-[3α,5α-dihydroxy-2β-(3-oxooctyl)-cyclopent-1β-yl]-hepta-2,4,6-trienoate, 15 ml. of acetone, 5 ml. of water and 0.3 ml. of concentrated sulfuric acid was heated under reflux in a nitrogen atmosphere for 3 hrs., then the mixture was evaporated under reduced pressure until most of the acetone had been removed and the residue was extracted with methylene chloride. The methylene chloride extract was washed with aqueous sodium bicarbonate, dried, and evaporated to a partly crystalline residue which was dissolved in a mixture of 33% ethyl acetate and 67% cyclohexane and chromatographed over 15 g. of silica gel. The column was eluted first with a mixture of 50% ethyl acetate and 50% cyclohexane and then with ethyl acetate. The ethyl acetate eluates were evaporated to give 161 mg. of an oil comprising ethyl 7-[3α,-5α-dihydroxy-2β-(3-oxooctyl)cyclopent-1β-yl]-hepta-2,4,6-trienoate, homogenous as shown by thin layer chromatography and showing strong hydroxyl absorption in the infrared and a U.V. absorption peak at 303 mμ.

A crude product prepared and chromatographed over silica gel as above was chromatographed over Florisil and eluted with Skellysolve B (mixed hexanes) containing acetone. The 20% acetone-80% Skellysolve B eluates were evaporated to give a pale yellow syrup which crystallized on standing. The thus obtained crystalline product was recrystallized twice from ether to give racemic ethyl 7-[3α,5α-dihydroxy-2β-(3-oxooctyl)cyclopent-1β-yl]hepta-2,4,6-trienoate having a melting point of 67°–69° C., an ultraviolet absorption maximum at 304 mμ ($\epsilon$ = 44,600), infrared absorption maxima at 3340, 3240, 1705, 1695, 1630, 1615, 1585, 1240, 1135 and 1005 cm.$^{-1}$, and the following analysis:

Calc'd. for $C_{22}H_{34}O_5$: C, 69.81; H, 9.05. Found: C, 69.60; H, 8.96.

Following the procedure of Preparation 29, but substituting for the 3α,5α-p-nitrobenzylidene derivative of racemic ethyl 7-[3,α,5α-dihydroxy-2β-(3-oxooctyl)-cyclopent-1β-yl]-2,4,6-heptatrienoate as starting material for the following compounds:

1. the 3α,5α-p-nitrobenzylidene derivative of racemic ethyl trans-[3α,5α-dihydroxy-2β-(3-oxooctyl)cyclopent-1β-yl] acrylate
2. the 3α,5α-p-nitrobenzylidene derivative of racemic methyl 5-[3α,5α-dihydroxy-2β-(3-oxooctyl)cyclopent-1β-yl]-2,4-pentadienoate
3. the 3α,5α-p-nitrobenzylidene derivative of racemic methyl 3-methyl-5-[3α,5α-dihydroxy-2β-(3-oxooctyl)cyclopent-1β-yl]-2,4-pentadienoate and
4. the 3α,5α-p-nitrobenzylidene derivative of racemic ethyl 7-[3α,5α-dihydroxy-2β-(3-oxobutyl)cyclopent-1β-yl]-2,4,6-heptatrienoate is productive of 1. racemic ethyl trans-[3α,5α-dihydroxy-2β-(3-oxooctyl)cyclopent-1β-yl]acrylate
2. racemic methyl 5-[3α,5α-dihydroxy-2β-(3-oxooctyl)cyclopent-1β-yl]-2,4-pentadienoate
3. racemic methyl 3-methyl-5-[3α,5α-dihydroxy-2β-(3-oxooctyl)cyclopent-1β-yl]-2,4-pentadienoate and
4. racemic ethyl 7-[3α,5α-dihydroxy-2β-(3-oxobutyl)-cyclopent-1β-yl]-2,4,6-heptatienoate.

Similarly, substituting other 3α,5α-acetals of racemic ethyl 7-[3α,5α-dihydroxy-2β-(3-oxooctyl)cyclopent-1β-yl]-2,4,6-heptatrienoate and other 3α,5α-acetals of the 3α,5α-dihydroxy compounds named following Preparation 29, for example, the 3α,5α-acetals of racemic ethyl 7-[3α,5α-dihydroxy-2β-(3-oxooctyl)cyclopent-1β-yl]-2,4,6-heptatrienoate wherein the acetal radical is derived from formaldehyde, acetaldehyde, propionaldehyde, chloral, p-bromobenzaldehyde, p-chlorobenzaldehyde, p-fluorobenzaldehyde, p-carbomethoxybenzaldehyde and 2,4,6-trichlorobenzaldehyde for the 3α,5α-p-nitrobenzylidene derivative of racemic ethyl 7-[3α,5α-dihydroxy-2β-(3-oxooctyl)cyclopent-1β-yl]-2,4,6-heptatrienoate as starting materials in the procedure of Preparation 29 is productive of the corresponding free 3α,5α-diols.

Substituting other alkyl esters of structure 10A in place of the methyl and ethyl esters named following .Example 34 as starting materials in the process of Example 34 is productive of the corresponding alkyl esters of structure IB.

Following the procedure of Preparation 29, but substituting for the 3α,5α-p-nitrobenzylidene derivative of racemic ethyl 7-[3α,5α-dihydroxy-2β-(3-oxooctyl)cyclopent-1β-yl]-2,4,6-heptatrienoate as starting material:

1. the 3α,5α-acetal of a racemic alkyl [3α,5α-dihydroxy-2β-(3-oxoalkyl)cyclopent-1β-yl] acrylate,
2. the 3α,5α-acetal of a racemic alkyl 5-[3α,5α-dihydroxy-2β-(3-oxoalkyl)cyclopent-1βyl𝜋-2,4-pentadienoate,
3. the 3α,5α-acetal of a racemic alkyl 3-methyl-5-[3α,5α-dihydroxy-2β-(3-oxoalkyl)cycolpent-1β-yl]-2,4-pentadienoate and
4. the 3α,5α-acetal of a racemic alkyl 7-[3α,5α-dihydroxy-2β-(3-oxoalkyl)cyclopent-1β-yl]-2,4,6-heptatrienoate is productive of 1. a racemic alkyl [3α,5α-dihydroxy-2β-(3-oxoalkyl)cyclopent-1β-yl] acrylate,
2. a racemic alkyl 5-[3α,5α-dihydroxy-2β-(3-oxoalkyl)cyclopent-1β-yl]-2,4-pentadienoate,
3. a racemic alkyl 3-methyl-5-[3α,5α-dihydroxy-2β-(3-oxoalkyl)cyclopent-1β-yl]-2,4-pentadienoate and
4. a racemic alkyl 7-[3α,5αdihydroxy-2β-(3-oxoalkyl)cyclopent-1β-yl]-2,4,6-heptatrienoate.

PREPARATION 30

Racemic ethyl trans-[3α,5α-dihydroxy-2β-(3-oxooctyl)cyclopent-1β-yl] acrylate (IB)

A solution of 0.623 g. of the 3α,5α-p-nitrobenzylidene derivative of racemic ethyl trans-[3α,5α-dihydroxy-2β-(3-oxooctyl)cyclopent-1β-yl] acrylate and 25 drops of concentrated sulfuric acid in a mixture of 50 ml. of acetone and 25 ml. of water was heated for one hour under reflux and then cooled. The acetone was then removed by evaporation under diminished pressure and the aqueous residue was extracted with methylene chloride. The methylene chloride solution was dried and chromatographed over Florisil. Elution with Skellysolve B containing 25–40% acetone and evaporation of the eluates gave 0.342 g. of an oil comprising racemic ethyl trans-[3α,5α-dihydroxy-2β-(3-oxooctyl)cyclopent-1β-yl] acrylate which on crystallization from ethyl acetate-Skellysolve B gave an analytical sample having a melting point of 80°–81° C., I.R. absorption maxima at 3260, 1705, 1650, 1175, 1095 and 1030 cm.$^{-1}$, and the following analysis:

Calc'd. for $C_{18}H_{30}O_5$: C, 66.23; H, 9.26. Found : C, 66.53; H, 9.25.

PREPARATION 31

Racemic ethyl 7-[3α,5α-dihydroxy-2β-(3-oxooctyl)cyclopent-1β-yl]-heptanoate (IA)

A mixture of 10.0 g. (0.0264 mole) of racemic ethyl 7-[3α,5α-dihydroxy-2β-(3-oxooctyl)cyclopent-1β-yl]-2,4,6-heptatrienoate (10B), 1.0 g. of 5% rhodium on alumina and 200 ml. of 95% ethanol was hydrogenated on the Parr apparatus at room temperature. After 2.5 hours 91% of the theoretical 3 moles of hydrogen had been absorbed and hydrogen uptake had ceased. The catalyst was removed by filtration and the filtrate was evaporated to give a syrup which was dissolved in 50% ethyl acetate/cyclohexane and chromatographed over 500 g. of silica gel. Elution with ethyl acetate and evaporation of the eluate gave a colorless oil comprising racemic ethyl 7-[3α,5α-dihydroxy-2β-(3-oxooctyl)cyclopent-1β-yl]-heptanoate showing a single spot, $R_f \sim 0.23$ when chromatographed on a silica gel thin-layer chromatography plate using 2 parts of ethyl acetate to 1 part of cyclohexane for development. Sulfuric acid charring gave an initial orange color of the spot. Nuclear magnetic resonance analysis supported the structure.

Following the procedure of Preparation 31 but substituting for racemic ethyl 7-[3α,5α-dihydroxy-2β-(3-oxooctyl)cyclopent-1β-yl]-2,4,6-heptatrienoate as starting material the following compounds of formula IB:

1. racemic ethyl trans-[3α,5α-dihydroxy-2β-(3-oxooctyl)cyclopent-1β-yl] acrylate,
2. racemic methyl 5-[3α,5α-dihydroxy-2β-(3-oxooctyl)cyclopent-1β-yl]-2,4-pentadienoate, ;8c
3. racemic methyl 3-methyl-5-[3α,5α-dihydroxy-2β-(3oxooctyl)cyclopent-1β-yl]-2,4-pentadienoate and
4. racemic ethyl 7-[3α,5α-dihydroxy-2β-(3-oxobutyl)-cyclopent-1β-yl]-2,4,6-heptatrienoate is productive of 1. racemic ethyl 3-[3α,5α-dihydroxy-2β-(3-oxooctyl)-cyclopent-1β-yl] propionate,
2. racemic methyl 5-[3α,5α-dihydroxy-2β-(3-oxooctyl)cyclopent-1β-yl] pentanoate,
3. racemic methyl 3-methyl-5-[3α,5α-dihydroxy-2β-(3-oxooctyl)cyclopent-1β-yl] pentanoate and
4. racemic ethyl 7-[3α,5α-dihydroxy-2β-(3-oxobutyl)-cyclopent-1β-yl] heptanoate.

Substituting other alkyl esters of formula IB as starting materials in the process of Preparation 31 in place of the methyl and ethyl esters of formula IB named following Preparation 31 is productive of the corresponding alkyl esters of formula IA.

PREPARATION 32

Racemic 7-[3α,5α-dihydroxy-2β-(3-oxooctyl)cyclopent-1β-yl] heptanoic acid (IA)

A mixture of 1.00 g. (0.0026 mole) of racemic ethyl 7-[3α,5α-dihydroxy-2β-(3-oxooctyl)cyclopent-1β-yl] heptanoate (IA) and 100 ml. of 0.5 N potassium hydroxide in 80% methanol was heated under reflux under a nitrogen atmosphere for 4 hrs. The mixture was concentrated to about ⅓ volume by evaporation under reduced pressure, then diluted with water and washed with methylene chloride. The aqueous phase was acidified with dilute hydrochloric acid and extracted several times with ethyl acetate. The ethyl acetate extracts were combined, washed with aqueous sodium chloride, dried and evaporated under reduced pressure to give a residue. The thus obtained residue was chromatographed on 50 g. of acid washed silica gel. The column was eluted with 250 ml. of 60% ethyl acetate-40% benzene and 500 ml. of ethyl acetate. The ethyl acetate fractions were evaporated to give 528 mg. of product which crystallized slowly on standing at about 10° C. Recrystallization of this material from anhydrous ether gave racemic 7-[3α,5α-dihydroxy-2β-(3-oxooctyl)cyclopent-1β-yl] heptanoic acid as fine prisms having a melting point of 66°–67° C., I.R. absorption maxima at 3460, 3400, 2900, 1710, 1700, 1235, 1225, 1205, 1185, 1115 and 1075 cm$^{-1}$, and the following analysis:

Calc'd. for $C_{20}H_{36}O_5$: C, 67.38; H, 10.18. Found : C, 67.10; H, 10.25.

Following the procedure of Preparation 32 but substituting for racemic ethyl 7-[3α,5α-dihydroxy-2β-(3-oxooctyl)cyclopent-1β-yl] heptanoate (IA) as starting material other esters of formulas 10A, IB, and IA, for example:

1. the 3α,5α-p-nitrobenzylidene derivative of racemic ethyl 7-[3α,5α-dihydroxy-2β-(3-oxooctyl)cyclopent-1β-yl]-2,4,6-heptatrienoate (10A),
2. the 3α,5α-p-nitrobenzylidene derivative of racemic ethyl trans-[3α,5α-dihydroxy-2β-(3-oxooctyl)cyclopent-1β-yl] acrylate (10A),
3. the 3α,5α-p-nitrobenzylidene derivative of racemic methyl 5-[3α,5α-dihydroxy-2β-(3-oxooctyl)cyclopent-1β-yl]-2,4-pentadienoate (10A),
4. the 3α,5α-p-nitrobenzylidene derivative of racemic methyl 3-methyl-5-[3α,5α-dihydroxy-2β-(3-oxooctyl)cyclopent-1β-yl]-2,4-pentadienoate (10A),
5. the 3α,5α-p-nitrobenzylidene derivative of racemic ethyl 7-[3α,5α-dihydroxy-2β-(3-oxobutyl)cyclopent-1β-yl]-2,4,6-heptatrienoate (10A),
6. racemic ethyl 7-[3α,5α-dihydroxy-2β-(3-oxooctyl)-cyclopent-1β-yl]-2,4,6-heptatrienoate (IB),
7. racemic ethyl trans-[3α,5α-dihydroxy-2β-(3-oxooctyl)cyclopent-1β-yl] acrylate (IB),
8. racemic methyl 5-[3α,5α-dihydroxy-2β-(3-oxooctyl)cyclopent-1β-yl]-2,4-pentadienoate (IB),
9. racemic methyl 3-methyl-5-[3α,5α-dihydroxy-2β-(3-oxooctyl)cyclopent-1β-yl]-2,4-pentadienoate (IB),
10. racemic ethyl 7-[3α,5α-dihydroxy-2β-(3-oxobutyl)cyclopent-1β-yl]-2,4,6-heptatrienoate (IB),
11. racemic ethyl 3-[3α,5α-dihydroxy-2β-(3-oxooctyl)cyclopent-1β-yl] propionate (IA),
12. racemic methyl 5-[3α,5α-dihydroxy-2β-(3-oxooctyl)cyclopent-1β-yl] pentanoate (IA),
13. racemic methyl 3-methyl-5-[3α,5α-dihydroxy-2β-(3-oxooctyl)cyclopent-1β-yl] pentanoate (IA), and
14. racemic ethyl 7-[3α,5α-dihydroxy-2β-(3-oxobutyl)cyclopent-1β-yl] heptanoate (IA), is productive of the corresponding free acids.

PREPARATION 33

Racemic methyl 7-[3α,5α-dihydroxy-2β-(3-oxooctyl)cyclopent-1β-yl] heptanoate (IA)

A solution of 0.2 g. of racemic 7-[3α,5α-dihydroxy-2β-(3-oxooctyl)cyclopent-1β-yl] heptanoic acid (IA) in a mixture of 1 ml. of methanol and 9 ml. of diethyl ether is mixed at room temperature with excess diazomethane in ether and allowed to stand for about 15 minutes. The mixture is then evaporated to dryness under diminished pressure to obtain a residue comprising racemic methyl 7-[3α,5α-dihydroxy-2β-(3-oxooctyl)cyclopent-1β-yl] heptanoate (IA), Following the procedure of Preparation 33 but substituting for diazomethane other diazoalkanes, for example, diazoethane, diazobutane, 1-diazo-2-ethylhexane, cyclohexyldiazomethane, 1-diazo-2-propene, diazododecane, and the like, gives ethyl, butyl, 2-ethylhexyl, cyclohexylmethyl, allyl, lauryl, and the like esters of racemic 7-[3α,5α-dihydroxy-2β-(3-oxooctyl)-cyclopent-1β-yl] heptanoic acid.

Following the procedure of Preparation 33 but substituting for 7-[3α,5α-dihydroxy-2β-(3-oxooctyl)cyclopent-1β-yl] heptanoic acid as starting material other free acids of formulas 10A, IB, and IA, for example, the free acids corresponding to the esters named following Preparation 32, is productive of the methyl esters of these acids. Similarly, substituting other diazoalkanes, for example, those named above, is productive of the corresponding alkyl esters of the acids of formulas 10A, IB, and IA.

PREPARATION 34

Racemic ethyl 7-[3α,5α-dihydroxy-2β-(3-hydroxyoctyl)cyclopent-1β-yl] heptanoate (IVD)

To a solution of 1.0 g. of racemic ethyl 7-[3α,5α-dihydroxy-2β-(3-oxooctyl)cyclopent-1β-yl] heptanoate (IA, from Preparation 31), in 40 ml. of tetrahydrofuran under a nitrogen atmosphere is added 3.5 g. of lithium tri-tert-butoxy aluminum hydride in portions over a period of 3 to 4 minutes. The solution is stirred for 3 hrs. at room temperature, concentrated to about one third volume by evaporation under reduced pressure, carefully acidified with dilute hydrochloric acid, and extracted with ethyl acetate. The ethyl acetate extract is washed with water, dried and evaporated under reduced pressure to give a gum comprising racemic ethyl 7-[3α,5α-dihydroxy-2β-(3-hydroxyoctyl)cyclopent-1β-yl] heptanoate (IV D) which can be further purified by chromatographing over silica gel, eluting with ethyl acetate to obtain the desired product.

EXAMPLE 1

Racemic ethyl 7-(4,4aα,5,6,7,7aβ-hexahydro-6α-hydroxy-2-pentylcyclopenta[b]pyran-5β-yl)-2,4,6-heptatrienoate (IIB) and racemic ethyl 7-(2,3,4,4aβ,5,6,7,7aβ-octahydro-6α-hydroxy-2-pentylidenecyclopenta[b]pyran-5β-yl)-2,4,6-heptatrienoate (IIB')

A solution of 5.0 g. of racemic ethyl 7-[3α,5α-dihydroxy-2β-(3-oxooctyl)cyclopent-1β-yl]-2,4,6-heptatrienoate (IB) in 100 ml. of toluene was heated under reflux in a nitrogen atmosphere for 40 hrs. while water was removed with a water trap. The solvent was then evaporated under reduced pressure leaving a residue comprising racemic ethyl 7-(4,4aα,5,6,7,7aβ-hexahydro-6α-hydroxy-2-pentylcyclopenta[b]pyran-5β-yl)-2,4,6-heptatrienoate (IIB) and the corresponding compound designated IIB'. The thus obtained residue was dissolved in a mixture of 20% ethyl acetate and 80% cyclohexane and chromatographed over 125 g. of silica gel. Elution with a mixture of 20% ethyl acetate and 80% cyclohexane followed by evaporation of the eluate gave 2.82 g. of a mixture comprising racemic ethyl 7-(4,4aα,5,6,7,7aβ-hexahydro-6α-hydroxy-2-pentylcyclopenta[b]pyran-5β-yl)-2,4,6-heptatrienoate and racemic ethyl 7-(2,3,4,4aα,5,6,7,7aβ-octahydro-6α-hydroxy-2-pentylidenecyclopenta[b]pyran-5β-yl)-2,4,6-heptatrienoate (IIB') as a yellow oil having the following analysis:

U.V.: $\lambda_{max}$ (EtOH): 304 mμ, E = 14,300, shoulder at 265 Mμ. I.R.: ($CH_2Cl_2$ solution): Principal bands at 3500, 1730, 1680, 1645, 1605, 1140 and 1015 cm$^{-1}$.

T.L.C. (Silica gel developed with 100% ethyl acetate) one spot, $R_f$ 76.

The spot turned black when sprayed with 50% sulfuric acid. The purified mixture comprising racemic ethyl 7-(4,4a$\alpha$5,6,7,7a$\beta$-hexahydro-6$\alpha$-hydroxy-2-pentylcyclopenta[b]pyran-5$\beta$-yl)-2,4,6-heptatrienoate (IIB) and racemic ethyl 7-(2,3,4,4a$\alpha$,5,6,7,7a$\beta$-octahydro-6$\alpha$-hydroxy-2-pentylidenecyclopenta[b]pyran-5$\beta$-yl)-2,4,6-heptatrienoate (IIB') can be used as a starting material in following Examples or can be separated by, for example, repeated chromatography over silica gel, reversed phase partition chromatography on siliconized celite, or preparative thin layer chromatography into components IIB and IIB', each of which can be used as a starting material in following Examples in place of an equal weight of the mixture.

Following the procedure of Example 1 but substituting for racemic ethyl 7-[3$\alpha$,5$\alpha$-dihydroxy-2$\beta$-(3-oxooctyl)cyclopent-1$\beta$-yl]-2,4,6-heptatrienoate as starting material the following compounds:

1. racemic ethyl trans-[3$\alpha$,5$\alpha$-dihydroxy-2$\beta$-(3-oxooctyl)cyclopent-1$\beta$-yl]acrylate (IB)
2. racemic methyl 5-[3$\alpha$,5$\alpha$-dihydroxy-2$\beta$-(3-oxooctyl)cyclopent-1$\beta$-yl]-2,4-pentadienoate (IB)
3. racemic methyl 3-methyl-5-[3$\alpha$,5$\alpha$-dihydroxy-2$\beta$-(3-oxooctyl)cyclopent-1$\beta$-yl]-2,4-pentadienoate (IB) and
4. racemic ethyl 7-[3$\alpha$,5$\alpha$-dihydroxy-2$\beta$-(3-oxobutyl)-cyclopent-1$\beta$-yl]-2,4,6-heptatrienoate (IB)

is productive of 1. racemic ethyl trans-(4,4a$\alpha$,5,6,7,7a$\beta$-hexahydro-6$\alpha$-hydroxy-2-pentylcyclopenta[b]pyran-5$\beta$-yl)-acrylate (IIB),
2. racemic methyl 5-(4,4a$\alpha$,5$\beta$6,7,7a$\beta$-hexahydro-6$\alpha$-hydroxy-2-pentylcyclopenta[b]pyran-5$\beta$-yl)-2,4-pentadienoate (IIB),
3. racemic methyl 3-methyl-5-(4,4a$\alpha$,5,6,7,7a$\beta$-hexahydro-6$\alpha$-hydroxy-2-pentylcyclopenta[b]pyran-5$\beta$-yl)-2,4-pentadienoate (IIB) and
4. racemic ethyl 7-(4,4a$\alpha$,5,6,7,7a$\beta$-hexahydro-6$\alpha$-hydroxy-2-methylcyclopenta[b]pyran-5$\beta$-yl)-2,4,6-heptatrienoate (IIB), and the corresponding compounds designated IIB'.

Substituting other alkyl esters of formula IB as starting materials in the process of Example 1 in place of the methyl and ethyl esters of formula IB named following Example 1 is productive of the corresponding esters of formula IIB andd IIB'.

Substituting the free acids of formula IB as starting materials in the process of Example 1, for example racemic 7-[3$\alpha$,5$\alpha$-dihydroxy-2$\beta$-(3-oxooctyl)cyclopent-1$\beta$-yl]-2,4,6-heptatrienoic acid (IB) and other free acids corresponding to the esters named following Example 1 is productive of the free acids of formula IIB, for example racemic 7-(4,4a$\alpha$,5,6,7,7a$\beta$-hexahydro-6$\alpha$-hydroxy-2-pentylcyclopenta[b]pyran-5$\beta$-yl)-2,4,6-heptatrienoic acid and the other free acids of formula IIB and IIB' corresponding to the esters of formula IIB named following Example 1. The free acids are purified by chromatography over acid washed silica gel and elution with a mixture of ethyl acetate, and benzene, or by other conventional means for purifying prostanoic acids.

EXAMPLE 2

Racemic ethyl 7-(4,4a$\alpha$,5,6,7,7a$\beta$-hexahydro-6$\alpha$-hydroxy-2-pentylcyclopenta[b]pyran-5$\beta$-yl)heptanoate (IIA) and racemic ethyl 7-(2,3,4,4a$\alpha$,5,6,7,7a$\beta$-octahydro-6$\alpha$-hydroxy-2-pentylidenecyclopenta[b]pyran-5$\beta$-yl)-heptanoate (IIA')

A solution of 4.5 g. of racemic ethyl 7-[3$\alpha$,5$\alpha$-dihydroxy-2$\beta$-(3-oxooctyl)cyclopent-1$\beta$-yl)heptanoate (IA) in 100 ml. of toluene was heated under reflux in a nitrogen atmosphere for 20 hrs. while water was removed with a water trap. The solvent was then evaporated under reduced pressure to give a residue comprising racemic ethyl 7-(4,4a$\alpha$,5,6,7,7a$\beta$-hexahydro-6$\beta$-hydroxy-2-pentylcyclopenta[b]pyran-5$\beta$-yl) -heptanoate (IIA) and the corresponding compound of formula IIA'. The thus obtained residue was dissolved in a mixture of 40% ethyl acetate and 60% cyclohexane and poured onto a chromatographic column containing 250 g. of silica gel. Elution with a mixture of 40% ethyl acetate and 60% cyclohexane followed by evaporation of the eluate gave 3.23 g. of a residue comprising racemic ethyl 7-(4,4a$\alpha$,5,6,7,7a$\beta$-hexahydro-6$\alpha$-hydroxy-2-pentylcyclopenta[b]pyran-5$\beta$-yl)heptanoate and racemic ethyl 7-(2,3,4,4a$\alpha$,5,6,7,7a$\beta$-octahydro-6$\alpha$-hydroxy-2-pentylidenecyclopenta[b]pyran-5$\beta$-yl)heptanoate (IIA') as a yellow oil having the following analysis:

I.R. ($CH_2Cl_2$ solution). Principle bands at 3425, 1750, 1690, 1190 and 1040 $cm^{-1}$. T.L.C. (Silica gel developed with 50% EtOAc - 50% cyclohexane): 1 spot, $R_f$ 0.60. The spot turned orange red when sprayed with 50% sulfuric acid. N.M.R. 273 c.p.s. (broad), 248 c.p.s. (quartet) 76 c.p.s. (triplet) and 54 c.p.s. (triplet).

The purified mixture comprising racemic ethyl 7-(4,4a$\alpha$,5,6,7,7a$\beta$-hexahydro-6$\alpha$-hydroxy-2-pentylcyclopenta[b]pyran-5$\beta$-yl)heptanoate (IIA) and racemic ethyl 7-(2,3,4,4a$\alpha$,5,6,7,7a$\beta$-octahydro-6$\alpha$-hydroxy-2-pentylidenecyclopenta[b]pyran-5$\beta$-yl)heptanoate (IIA') can be used as a starting material in subsequent Examples or can be separated by, for example, repeated chromatography over silica gel, reversed phase partition chromatography on siliconized celite, or preparative thin layer chromatography into components IIA and IIA', each of which can be used as a starting material in following Examples in place of an equal weight of the mixture.

Following the procedure of Example 2, but substituting for racemic ethyl 7-[3$\alpha$,5$\alpha$-dihydroxy-2$\beta$-(3-oxooctyl)cyclopent-1$\beta$-yl]heptanoate as starting material the following compounds:

1. racemic ethyl 3-[3$\alpha$,5$\alpha$-dihydroxy-2$\beta$-(3-oxooctyl)cyclopent-1$\beta$-yl]propionate, (IA)
2. racemic methyl 5-[3$\alpha$,5$\alpha$-dihydroxy-2$\beta$-(3-oxooctyl)cyclopent-1$\beta$-yl]pentanoate, (IA)
3. racemic methyl 3-methyl-5-[3$\alpha$,5$\alpha$-dihydroxy-2$\beta$-(3-oxooctyl)cyclopent-1$\beta$-yl]pentanoate (IA) and
4. racemic ethyl 7-[3$\alpha$,5$\alpha$-dihydroxy-2$\beta$-(3-oxobutyl)-cyclopent-1$\beta$-yl]heptanoate (IA)

is productive of 1. racemic ethyl 3-[4,4a$\alpha$,5,6,7,7a$\beta$-hexahydro-6$\alpha$-hydroxy-2-pentylcyclopenta[b]pyran-5$\beta$-yl)propionate, (IIA), 2. racemic methyl 5-(4,4aα,5,6,7,7aβ-hexahydro-6α-hydroxy-2-pentylcyclopenta[b]pyran-5β-yl)pentanoate, (IIA),
3. racemic methyl 3-methyl-5-(4,4aα,5,6,7,7aβ-hexahydro-6α-hydroxy-2-pentylcyclopenta[b]pyran-5β-yl)pentanoate (IIA) and
4. racemic ethyl 7-(4,4aα,5,6,7,7aβ-hexahydro-6α-hydroxy-2-methylcyclopenta[b]pyran-5β-yl)heptanoate (IIA), and the corresponding compounds of formula IIA'.

Substituting other alkyl esters of formula IA as starting materials in the process of Example 2 in place of the methyl and ethyl esters of formula IA named following Example 2 is productive of the corresponding alkyl esters of formulas IIA and IIA'.

Substituting the free acids of formula IA as starting materials in the process of Example 2, for example racemic 7-(3α,5α-dihydroxy-2β-3-(oxooctyl)cyclopent-1β-yl]heptanoic acid (IA) and other free acids corresponding to the esters of formula IA named following Example 2 is productive of the free acids of formula IIA, for example racemic 7-(4,4aα,5,6,7,7aβ-hexahydro-6α-hydroxy-2-pentylcyclopenta[b]pyran-5β-yl)heptanoic acid and the other free acids of formulas IIA and IIA' corresponding to the esters of formula IIA named following Example 2. The free acids of formulas IIA and IIA' can be purified by chromatography over acid washed silica gel, or by other conventional means for purifying prostanoic acids.

EXAMPLE 3

Racemic ethyl 7-(4,4aα,5,6,7,7aβ-hexahydro-6α-hydroxy-2-pentylcyclopenta[b]pyran-5β-yl)heptanoate (IIA) and racemic ethyl 7-(2,3,4,4aα,5,6,7,7aβ-octahydro-6α-hydroxy-2-pentylidenecyclopenta[b]pyran-5β-yl)-2,4,6-heptatrienoate (IIA').

A mixture of 10.0 g. of racemic ethyl 7-(4,4aα,5,6,7,7aβ-hexahydro-6α-hydroxy-2-pentyl-cyclopenta[b]-pyran-5β-yl)-2,4,6-heptatrienoate, (IIB), and the corresponding compound designated IIB' 1.0 g. of 5% rhodium on alumina and 200 ml. of 95% ethanol is hydrogenated at room temperature until the uptake of hydrogen ceases. The catalyst is removed by filtration and the filtrate is evaporated to give a residue comprising racemic ethyl 7-(4,4aα,5,6,7,7aβ-hexahydro-6α-hydroxy-2-pentylcyclopenta[b]pyran-5β-yl)heptanoate, (IIA) and the corresponding compound of formula IIA'. The thus obtained residue is further purified by chromatography over silica gel as described in Example 2.

Substituting other compounds of formula IIB and IIB' as starting materials in the process of Example 3 in place of the named mixture of compounds of formulas IIB and IIB' is productive of the corresponding compounds of formulas IIA and IIA'.

EXAMPLE 4

Racemic ethyl 7-(4,4aα,5,6,7,7aβ-hexahydro-6-oxo-2-pentylcyclopenta[b]pyran-5β-yl)heptanoate (IIIA), racemic ethyl 7-(2,3,4,4aα,5,6,7,7aβ-octahydro-6-oxo-2-pentylidenecyclopenta[b]pyran-5β-yl)-heptanoate (IIIA'), and racemic ethyl 7-[3α-hydroxy-5-oxo-2β-(3-oxooctyl)cyclopent-1β-yl]heptanoate (IVA).

A solution of 1.22 g. of a mixture comprising racemic ethyl 7-(4,4aα,5,6,7,7aβ-hexahydro-6α-hydroxy-2-pentylcyclopenta[b]pyran-5β-yl)heptanoate (IIA) and racemic ethyl 7-(2,3,4,4aα,5,6,7,7aβ-octahydro-6α-hydroxy-2-pentylidenecyclopenta[b]pyran-5β-yl)heptanoate (IIA') in 10 ml. of pyridine was cooled in an ice bath and stirred while adding 1.2 g. of chromic anhydride. Stirring was continued. After 5–10 minutes the mixture thickened. The cooling bath was removed and the mixture was stirred for 2 hrs. longer, then was diluted with aqueous sodium bisulfite and extracted 4 times with methylene chloride. The methylene chloride extracts were combined, washed with aqueous sodium chloride, dried, and evaporated to give a residue comprising a mixture of racemic ethyl 7-(4,4aα,5,6,7,7aβ-hexahydro-6-oxo-2-pentylcyclopenta[b]pyran-5β-yl)heptanoate (IIIA), racemic ethyl 7-(2,3,4,4aα,5,6,7,7aβ-octahydro-6-oxo-2-pentylidenecyclopenta[b]pyran-5β-yl)-heptanoate (IIIA') and racemic ethyl 7-[3α-hydroxy-5-oxo-2β-(3-oxooctyl)cyclopent-1β-yl]heptanoate (IVA). The thus obtained residue was dissolved in a mixture of 20% ethyl acetate and 80% cyclohexane and chromatographed on 50 g. of silica gel. Elution with a mixture of 20% ethyl acetate and 80% cyclohexane and evaporation of the eluates gave 0.82 g. of a mixture comprising racemic ethyl 7-(4,4aα,5,6,7,7aβ-hexahydro-6-oxo-2-pentylcyclopenta[b]pyran-5β-yl)heptanoate (IIIA) and racemic ethyl 7-(2,3,4,4aα,5,6,7,7aβ-octahydro-6-oxo-2-pentylidenecyclopenta[b]pyran-5β-yl)heptanoate (IIIA') having the following analysis:
I.R. ($CH_2Cl_2$ solution): Principal bands at 1750, 1740, 1670, 1190, 1885, 1115, 1085 and 1035 cm$^{-1}$. N.M.R.: Absorption bands at 279 c.p.s., 248 c.p.s. (quartet) and 74 c.p.s. (triplet). T.L.C. (Silica gel, developed with 66% ethyl acetate in cyclohexane) One spot, $R_f$ 0.69. The spot turned orange when sprayed with 50% sulfuric acid.

Elution of the silica gel column with 100% ethyl acetate and evaporation of the eluates gave 0.14 g. of racemic ethyl 7-[3α-hydroxy-5-oxo-2β-(3-oxooctyl)-cyclopent-1β-yl]heptanoate (IVA) having the following analysis:
I.R. ($CH_2Cl_2$ solution): Principal bands at 3610, 1670, 1650 (shoulder), 1390, 1195 and 1020 cm$^{-1}$. T.L.C. (Silica gel, developed with 66% ethyl acetate in cyclohexane) One spot, $R_f$ 0.51. The spot turned yellow when sprayed with 50% sulfuric acid.

The purified mixture comprising racemic ethyl 7(4,4aα,5,6,7,7aβ-hexahydro-6-oxo-2-pentylcyclopenta[b]pyran-5β-yl)heptanoate (IIIA) and racemic ethyl 7-(2,3,4,4aα,5,6,7,7aβ-octahydro-6-oxo-2-pentylidenecyclopenta[b]pyran-5β-yl)heptanoate (IIIA') can be used as a starting material in subsequent Examples or can be separated by, for example, repeated chromatography over silica gel, reversed phase partition chromatography on siliconized celite, or preparative thin layer chromatography, into the formula IIIA and IIIA' components, each of which can be used as a starting material in subsequent examples in place of an equal weight of the mixture.

Following the procedure of Example 4 but substituting for racemic ethyl 7-(4,4aα,5,6,7,7aβ-hexahydro-6α-hydroxy-2-pentylcyclopenta[b]pyran-5β-yl)-heptanoate (IIA) and the corresponding compound of formula IIA' as starting material the following compounds:

1. racemic ethyl 3-(4,4aα5,6,7,7aβ-hexahydro-6α-hydroxy-2-pentylcyclopenta[b]pyran-5β-yl)propionate (IIA),
2. racemic methyl 5-(4,4aα,5,6,7,7aβ-hexahydro-6α-hydroxy-2-pentylcyclopenta[b]pyran-5β-yl)pentanoate (IIA),
3. racemic methyl 3-methyl-5-(4,4aα,5,6,7,7aβ-hexahydro-6α-hydroxy-2-pentylcyclopenta[b]pyran-5β-yl)pentanoate (IIA), and
4. racemic ethyl 7-(4,4aα,5,6,7,7aβ-hexahydro-6α-hydroxy-2-methylcyclopenta[b]pyran-5β-yl)pentanoate (IIA), and the corresponding compounds of formula IIA' is productive of 1. racemic ethyl 3-(4,4aα,5,6,7,7aβ-hexahydro-6-oxo-2-pentylcyclopenta[b]pyran-5β-yl)propionate (IIIA) and racemic ethyl 3-[3α-hydroxy-5-oxo-2β-(3-oxooctyl)-cyclopent-1β-yl]propionate (IVA).
2. racemic ethyl 5-(4,4aα,5,6,7,7aβ-hexahydro-6-oxo-2-pentylcyclopenta[b]pyran-5β-yl)pentanoate (IIIA) and racemic methyl 5-[3α-hydroxy-5-oxo-2β-(3-oxooctyl)-cyclopent-1β-yl]pentanoate (IVA),
3. racemic methyl 3-methyl-5-(4,4aα,5,6,7,7aβ-hexahydro-6-oxo-2-pentylcyclopenta[b]pyran-5β-yl)pentanoate (IIIA) and racemic methyl 3-methyl-5-[3α-hydroxy-5-oxo-2β-(3-oxooctyl)cyclopent-1β-yl]pentanoate (IVA), and
4. racemic ethyl 7-(4,4aα,5,6,7,7aβ-hexahydro-6-oxo-2-methylcyclopenta[b]pyran-5β-yl)heptanoate (IIIA) and racemic ethyl 7-[3α-hydroxy-5-oxo-2β-(3-oxobutyl)cyclopent-1β-yl]heptanoate (IVA), and the corresponding compounds designated IIIA'.

Substituting other alkyl esters of formulas IIA and IIA' as starting materials in the process of Example 4 in place of the methyl and ethyl esters of formula IIA named following Example 4 is productive of the corresponding alkyl esters of formulas IIIA, IIIA', and IVA. Substituting the free acids of formula IIA and IIA' as starting materials in the process of Example 4, for example racemic 7-(4,4aα,5,6,7,7aβ-hexahydro-6α-hydroxy-2-pentylcyclopenta[b]pyran-5β-yl)heptanoic acid (IIA) and other free acids corresponding to the esters of formula IIA named following Example 4 is productive of the free acids of formulas IIIA, IIIA' and IVA, for example racemic 7-(4,4aα,5,6,7,7aβ-hexahydro-6-oxo-2-pentylcyclopenta[b]pyran-5β-yl)-heptanoic acid (IIIA) and racemic 7-[3α-hydroxy-5-oxo-2β-(3-oxooctyl)cyclopent-1β-yl]heptanoic acid (IVA) and the other free acids of formulas IIIA, IIIA' and IVA corresponding to the esters of formulas IIIA and IVA named following Example 4.

EXAMPLE 5

Racemic ethyl 7-[3α-hydroxy-5-oxo-2β-(3-oxooctyl)cyclopent-1β-yl]heptanoate (IVA)

Following the procedure of Example 4 but substituting for racemic ethyl 7-(4,4aα,5,6,7,7aβ-hexahydro-6-oxo-2-pentylcyclopenta[b]pyran-5β-yl)heptanoate (IIIA) as starting material other compounds of formula IIIA, for example the compounds of formula IIIA named following Example 4, is productive of the corresponding compounds of formula IVA.

Following the procedure of Example 4 but substituting for racemic ethyl 7-(4,4aα,5,6,7,7aβ-hexahydro-6-oxo-2-pentylcyclopenta[b]pyran-5β-yl)heptanoate (III) as starting material a mixture of racemic ethyl 7-(4,4aα,5,6,7,7aβ-hexahydro-6-oxo-2-pentylcyclopenta[b]pyran-5β-yl)heptanoate (III) and racemic ethyl 7-(2,3,4,4aα,5,6,6,7aβ-octahydro-6-oxo-2-pentylidenecyclopenta[b]pyran-5β-yl)heptanoate (IIIA') is productive of racemic ethyl 7-[3α-hydroxy-5-oxo-2β-(3-oxooctyl)cyclopent-1β-yl]heptanoate (IVA).

EXAMPLE 6

Racemic ethyl 7-[3α-hydroxy-5-oxo-2β-(3-oxooctyl)cyclopent-1β-yl]heptanoate (IVA) and racemic ethyl 7-[5-oxo-2β-(3-oxooctyl)-3-cyclopenten-1β-yl]heptanoate (VA)

A solution of 700 mg. of a mixture comprising racemic ethyl 7(4,4aα,5,6,7,7aβ-hexahydro-6-oxo-2-pentylcyclopenta[b]pyran-5β-yl)heptanoate (IIIA) and racemic ethyl 7-(2,3,4,4aα,5,6,7aβ-octahydro-6-oxo-2-pentylidenecyclopenta[b]pyran-5β-yl)heptanoate (IIIA') in about 10 ml. of acetone was treated with about 3 ml. of 5% hydrochloric acid and allowed to stand at room temperature for 2 hrs., then was neutralized with aqueous sodium bicarbonate. Most of the acetone was removed by evaporation under diminished pressure and the residue was extracted with methylene chloride. The methylene chloride extract was dried and evaporated giving a residue comprising racemic ethyl 7-[3α-hydroxy-5-oxo-2β-(3-oxooctyl)cyclopent-1β-yl]-heptanoate (IVA) and racemic ethyl 7-[5-oxo-2β-(3-oxooctyl)-3-cyclopenten-1β-yl]heptanoate (VA). The thus obtained residue was dissolved in a mixture of 33% ethyl acetate and 67% cyclohexane and chromatographed over 100 g. of silica gel. The column was eluted with a mixture of 33% ethyl acetate and 67% cyclohexane and the eluates were evaporated to give 400 mg. of racemic ethyl 7-[5-oxo-2β-(3-oxooctyl)-3-cyclopenten-1β-yl]heptanoate (VA), identified by U.V., I.R., T.L.C. and N.M.R. analysis. Further elution of the silica gel column with a mixture of 50% ethyl acetate and 50% cyclohexane and evaporation of the eluates gave 200 mg. of racemic ethyl 7[3α-hydroxy-5-oxo-2β-(3-oxooctyl)cyclopent-1β-yl]heptanoate (IVA), identified by I.R., T.L.C. and N.M.R. analysis.

EXAMPLE 7

Racemic 7-[3α-hydroxy-5-oxo-2β-(3-oxooctyl)cyclopent-1β-yl]heptanoic acid (IVA)

A solution of 0.25 g. of a mixture comprising racemic ethyl 7-(4,4aα,5,6,7,7aβ-hexahydro-6-oxo-2-pentylcyclopenta[b]pyran-5β-yl)heptanoate (IIIA) and racemic ethyl 7[2,3,4,4aα,5,6,7,7aβ-octahydro-6-oxo-2-pentylidenecyclopenta[b]pyran-5β-yl)heptanoate (IIIA') in 8 ml. of 95% ethanol was mixed with a solution of 0.25 g. of potassium carbonate in 2 ml. of water and the mixture was heated under reflux under a nitrogen atmosphere for 3 hrs., then the mixture was evaporated to dryness under reduced pressure to give a residue comprising the potassium salt of racemic 7-(4,4aα,5,6,7,7aβ-hexahydro-6-oxo-2-pentylcyclopenta[b]pyran-5β-yl)-heptanoic acid (IIIA) and the potassium salt of racemic 7-2,3,4,4aα,5,6,7,7aβ-octahydro-6-oxo-2-pentylidenecyclopenta[b]pyran-5β-yl)-heptanoic acid (IIIA'). The residue was dissolved in water, acidified with acetic acid, and extracted with ethyl acetate. The ethyl acetate extract was washed with aqueous sodium chloride, dried over magnesium sulfate, and evaporated to give a residue comprising racemic 7-[3α-hydroxy-5-oxo-2β-(3-oxooctyl)-cyclopent-1β-yl]heptanoic acid (IVA). The thus obtained residue was dissolved in benzene and chromatographed over 25 g. of acid-washed silica gel. The column was eluted with 50% ethyl acetate in benzene and the eluates evaporated to give 0.20 g. of racemic 7-[3α-hydroxy-5-oxo-2β-(3-oxooctyl)-cyclopent-1β-yl]heptanoic acid (IVA), having the following analysis:

I.R. ($CH_2Cl_2$ solution): Principle bands at 3450, 1760, 1750 (sh.), 1395, 1195 and 1040 $cm^{-1}$.

Following the procedure of Example 7 but substituting for racemic ethyl 7-(4,4aα,5,6,7,7aβ-hexahydro-6-oxo-2-pentylcyclopenta[b]pyran-5β-yl)-heptanoate (IIIA) as starting material the following compounds:

1. racemic ethyl 3-(4,4aα,5,6,7,7aβ-hexahydro-6-oxo-2-pentylcyclopenta[b]pyran-5β-yl)propionate (IIIA),
2. racemic methyl 5-(4,4aα,5,6,7,7aβ-hexahydro-6-oxo-2-pentylcyclopenta[b]pyran-5β-yl)pentanoate (IIIA),
3. racemic methyl 3-methyl-5-(4,4aα,5,6,7,7aβ-hexahydro-6-oxo-2-pentylcyclopenta[b]pyran-5β-yl)pentanoate (IIIA),
4. racemic ethyl 7-(4,4aα,5,6,7,7aβ-hexahydro-6-oxo-2-methylcyclopenta[b]pyran-[5β-yl)heptanoate (IIIA) and the corresponding compounds designated IIIA', and the like, is productive of 1. racemic 3-[3α-hydroxy-5-oxo-2β-(3-oxooctyl)-cyclopent-1βyl]propionic acid (IVA),
2. racemic 5-[3α-hydroxy-5-oxo-2β-(3-oxooctyl)-cyclopent-1β-yl]pentanoic acid (IVA),
3. racemic 3-methyl-5-[3α-hydroxy-5-oxo-2β-(3-oxooctyl)cyclopent-1β-yl]pentanoic acid (IVA),
4. racemic 7-[3α-hydroxy-5-oxo-2β-(3-oxobutyl)-cyclopent-1β-yl]heptanoic acid (IVA), and the like.

EXAMPLE 8

Racemic ethyl 7-[5-oxo-2β-(3-oxooctyl)-3-cyclopenten-1β-yl]heptanoate (VA)

A solution of 150 mg. of racemic ethyl 7-[3α-hydroxy-5-oxo-2β-(3-oxooctyl)cyclopent-1β-yl]heptonate (IVA) in 3 ml. of 90% acetic acid was heated at 60° under a nitrogen atmosphere for 20 hours. The solvent was then evaporated under reduced pressure giving a residue comprising racemic ethyl 7-[5-oxo-2β-(3-oxooctyl)-3-cyclopenten-1β-yl]heptanoate (VA). The thus-obtained residue was dissolved in a mixture of 20% ethyl acetate and 80% cyclohexane and chromatographed over 15 g. of silicagel. Elution with a mixture of 20% ethyl acetate and 80% cyclohexane and evaporation of the eluates gave racemic ethyl 7-[5-oxo-2β-(3-oxooctyl)-3-cyclopenten-1β-yl]heptanoate (VA) having the following analysis:

U.V. (95% ethanol): λ max. 220 mμ.
I.R. (Oil, neat on plate): Principal bonds at 1750, 1720, 1595, 1190 and 1030 $cm^{-1}$.
N.M.R. 454 c.p.s. (quartet), 356 c.p.s. (quartet), 247 c.p.s. (quartet), 76 c.p.s. (triplet) and 53 c.p.s.
T.L.C. (Silicagel, eluted with 50% ethyl acetate-50% cyclohexane): $R_f$ = 0.54. Spot turns yellow then brown when sprayed with 50% sulfuric acid.

Following the procedure of Example 8 but substituting for racemic ethyl 7-[3α-hydroxy-5-oxo-2β-(3-oxooctyl)cyclopent-1β-yl]heptanoate (IVA) as starting material other compounds of formula IVA, for example:

1. racemic ethyl 3-[3α-hydroxy-5-oxo-2β-(3-oxooctyl)cyclopent-1β-yl]propionate (IVA),
2. racemic methyl 5-[3α-hydroxy-5-oxo-2β-(3-oxooctyl)cyclopent-1β-yl]pentanoate (IVA),
3. racemic methyl 3-methyl-5-[3α-hydroxy-5-oxo-2β-(3-oxooctyl)cyclopent-1β-yl]pentanoate (IVA),
4. racemic ethyl 7-[3α-hydroxy-5-oxo-2β-(3-oxobutyl)cyclopent-1β-yl]heptanoate (IVA), and the like, is productive of 1. racemic ethyl 3-[5-oxo-2β-(3-oxooctyl)-3-cyclopenten-1β-yl]propionate (VA),
2. racemic ethyl 5-[5-oxo-2β-(3-oxooctyl)-3-cyclopenten-1β-yl]pentanoate (VA),
3. racemic methyl 3-methyl-5-[5-oxo-2β-(3-oxooctyl)-3-cyclopenten-1β-yl]pentanoate (VA),
4. racemic ethyl 7-[5-oxo-2β-(3-oxobutyl)-3-cyclopenten-1β-yl]heptanoate (VA), and the like.

Substituting the free acids of formula IVA as starting materials in the process of Example 8, for example racemic 7-[3α-hydroxy-5-oxo-2β-(3-oxooctyl)cyclopent-1β-yl]heptanoic acid (IVA) and other free acids corresponding to the esters of formula IVA named following Example 8 is productive of the free acids of formula VA, for example racemic 7-[5-oxo-2β-(3-oxooctyl)-3-cyclopenten-1β-yl]heptanoic acid (VA) and the other free acids of formula VA corresponding to the esters of formula VA named following Example 8. The free acids of formula VA can be purified by chromatography over acid washed silica gel, or by other conventional means for purifying prostanoic acids.

EXAMPLE 9

Racemic ethyl 7-[5-oxo-2β-(3-oxooctyl)cyclopent-1β-yl]heptanoate (VIA)

A solution of 400 mg. of racemic ethyl 7-[5-oxo-2β-(3-oxooctyl)-3-cyclopenten-1β-yl]heptanoate (VA) in 25 ml. of ethyl acetate is hydrogenated at atmospheric pressure using 125 mg. of 5% palladium on carbon catalyst. The hydrogenation is stopped after about one mole equivalent of hydrogen is absorbed. The catalyst is separated by filtration and the filtrate is evaporated under reduced pressure giving a residue. The thus-obtained residue is dissolved in a mixture of 20% ethyl acetate and 80% cyclohexane, and chromatographed on 35 g. of silica gel. The column is eluted with a mixture of 20% ethyl acetate and 80% cyclohexane, then with a mixture of 33% ethyl acetate and 67% cyclohexane. The eluate fractions are evaporated and the residues showing I.R. absorption at 1750 cm$^{-1}$ and little or no I.R. absorption at 1595 cm$^{-1}$ are combined. The combined residues comprising racemic ethyl 7-[5-oxo-2$\beta$-(3-oxooctyl)cyclopent-1$\beta$-yl]heptanoate (VIA) can be further purified by chromatography over Florisil (synthetic magnesium silicate) using hexane containing 5% acetone as eluant.

Following the procedure of Example 9 but substituting for racemic ethyl 7-[5-oxo-2$\beta$-(3-oxooctyl)-3-cyclopenten-1$\beta$-yl]heptanoate (VA) as starting material other compounds of formula VA, for example:

1. racemic ethyl 3-[5-oxo-2$\beta$-(3-oxooctyl)-3-cyclopenten-1$\beta$-yl]propionate (VA),
2. racemic methyl 5-[5-oxo-2$\beta$-(3-oxooctyl)-3-cyclopenten-1$\beta$yl]pentanoate (VA),
3. racemic methyl 3-methyl-5-[5-oxo-2$\beta$-(3-oxooctyl)-3-cyclopenten-1$\beta$-yl]pentanoate (VA),
4. racemic ethyl 7-[5oxo-2$\beta$-(3-oxobutyl)-3-cyclopenten-1$\beta$-yl]heptanoate (VA), and the like, is productive of 1. racemic ethyl 3-[5-oxo-2$\beta$-(3-oxooctyl)cyclopentan-1$\beta$-yl]propionate (VIA),
2. racemic methyl 5-[5-oxo-2$\beta$-(3-oxooctyl)cyclopentan-1$\beta$-yl]pentanoate (VIA),
3. racemic methyl 3methyl-5-[5-oxo-2$\beta$-(3-oxooctyl)-cyclopentan-1$\beta$-yl]pentanoate (VIA),
4. racemic ethyl 7-[5-oxo-2$\beta$-(3-oxobutyl)cyclopentan-1$\beta$-yl]heptanoate (VIA), and the like.

Substituting the free acids of formula VA as starting materials in the process of Example 9, for example racemic 7-[5-oxo-2$\beta$-(3-oxooctyl)-3-cyclopenten-1$\beta$-yl]heptanoic acid (VA) and the other free acids of formula VA corresponding to the esters of formula VA named following Example 9 is productive of the free acids of formula VIA, for example racemic 7-[5-oxo-2$\beta$-(3-oxooctyl)cyclopentan-1$\beta$-yl]heptanoic acid (VIA) and the other free acids of formula VIA named following Example 9. The free acids of formula VIA can be purified by chromatography over acid washed silica gel or by other convention means for purifying prostanoic acids.

EXAMPLE 10

Racemic ethyl
7-[3$\alpha$-hydroxy-5oxo-2$\beta$(3-oxo-1-octenyl)cyclopent-1$\beta$-yl]heptanoate (IVB)

A mixture of 10 g. of racemic ethyl 7-[3$\alpha$-hydroxy-5-oxo-2$\beta$-(3-oxooctyl)cyclopent-1$\beta$-yl]heptanoate (IVA), 10 g. of selenium dioxide, and 500 ml. of tetrahydrofuran is heated under reflux under a nitrogen atmosphere until TLC analysis of a sample indicates substantial absence of starting material. The reaction mixture is then cooled and filtered through Celite (diatomaceous earth filter aid). The filtrate is evaporated under reduced pressure giving a residue which is dissolved in ethyl acetate and filtered. The filtrate is washed with aqueous ammonium sulfide, dilute aqueous ammonia, dilute hydrochloric acid, aqueous sodium becarbonate and water, then is dried over anhydrous sodium sulfate and evaporated under reduced pressure to give a residue comprising racemic ethyl 7-[3$\alpha$-hydroxy-5-oxo-2$\beta$-(3-oxo-1-octenyl)cyclopent-1$\beta$-yl]heptanoate (IVB). The thus-obtained residue is dissolved in a small amount of ethyl acetate in cyclohexane and chromatographed over 1000 g. of silica gel, eluting with increasing amounts of ethyl acetate in cyclohexane. The eluate fractions are evaporated to dryness and the residues identified by possession of U.V. absorption at 231–234 m$\mu$ and development of absorption at 278 m$\mu$ on treatment with 0.5 N sodium hydroxide at 37°C. are considered to give racemic ethyl 7-[3$\alpha$-hydroxy-5-oxo-2$\beta$-(3-oxo-1-octenyl)cyclopent-1$\beta$-yl]heptanoate (IVB).

Following the procedure of Example 10 but substituting for racemic ethyl 7-[3$\alpha$-hydroxy-5-oxo-2$\beta$-(3-oxooctyl)cyclopent-1$\beta$-yl]heptanoate (IVA) as starting material other compounds of formula IVA, and compounds of formulas VA and VIA, for example:

1. racemic ethyl 3-[3$\alpha$-hydroxy-5-oxo-2$\beta$-(3-oxooctyl)cyclopent-1$\beta$-yl]propionate (IVA),
2. racemic methyl 5-[3$\alpha$-hydroxy-5-oxo-2$\beta$-(3-oxooctyl)cyclopent-1$\beta$-yl]pentanoate (IVA),
3. racemic methyl 3-methyl-5-[3$\alpha$-hydroxy-5-oxo-2$\beta$-(3-oxooctyl)cyclopent-1$\beta$-yl]pentanoate (IVA),
4. racemic ethyl 7-[3$\alpha$-hydroxy-5-oxo-2$\beta$-(3-oxobutyl)cyclopent-1$\beta$-yl]heptanoate (IVA),
5. racemic ethyl 7-[5-oxo-2$\beta$-(3-oxooctyl)cyclopent-1$\beta$-yl]heptanoate (VIA),
6. racemic ethyl 3-[5-oxo-2$\beta$-(3-oxooctyl)cyclopent-1$\beta$-yl]propionate (VIA),
7. racemic methyl 5-[5-oxo-2$\beta$-(3-oxooctyl)cyclopent-1$\beta$-yl]pentanoate (VIA),
8. racemic methyl 3-methyl-5-[5-oxo-2$\beta$-(3-oxooctyl)-cyclopent-1$\beta$-yl]pentanoate (VIA),
9. racemic ethyl 7-[5-oxo-2$\beta$-(3-oxobutyl)cyclopent-1$\beta$-yl]heptanoate (VIA), and the like, is productive of:

1. racemic ethyl 3-[3$\alpha$-hydroxy-5-oxo-2$\beta$-(3-oxo-1-octenyl)cyclopent-1$\beta$-yl]propionate (IVB),
2. racemic methyl 5-[3$\alpha$-hydroxy-5-oxo-2$\beta$-(3-oxo-1-octenyl)cyclopent-1$\beta$-yl]pentanoate (IVB),
3. racemic methyl 3-methyl-5-[3$\alpha$-hydroxy-5-oxo-2$\beta$-(3-oxo-1-octenyl)cyclopent-1$\beta$-yl]pentanoate (IVB),
4. racemic ethyl 7-[3$\alpha$-hydroxy-5-oxo-2$\beta$-(3-oxo-1-butenyl)cyclopent-1$\beta$-yl]heptanoate (IVB),
5. racemic ethyl 7-[5-oxo-2$\beta$-(3-oxo-1-octenyl)cyclopent-1$\beta$-yl]heptanoate (VIB),
6. racemic ethyl 3-[5-oxo-2$\beta$-(3-oxo-1-octenyl)cyclopent-1$\beta$-yl]propionate (VIB),
7. racemic methyl 5-[5-oxo-2$\beta$-(3-oxo-1-octenyl)cyclopent-1$\beta$-yl]pentanoate (VIB),
8. racemic methyl 3-methyl-5-[5-oxo-2$\beta$-(3-oxo-1-octenyl)cyclopent-1$\beta$-yl]pentanoate (VIB),
9. racemic ethyl 7-[5-oxo-2$\beta$-(3-oxo-1-butenyl)cyclopent-1$\beta$-yl]heptanoate (VIB), and the like.

Substituting the free acids of formulas IVA and VIA as starting materials in the process of Example 10, for example racemic 7-[3$\alpha$-hydroxy-5-oxo-2$\beta$-(3-oxooctyl)cyclopent-1β-yl]heptanoic acid (IVA) and the other free acids of formulas IVA and VIA corresponding to the esters of formulas IVA and VIA named following Example 10 is productive of the free acids of formulas IVB and VIB, for example racemic 7-[3α-hydroxy-5-oxo-2β-(3-oxo-1-octenyl)cyclopent-1β-yl]heptanoic acid (IVB) and the other free acids of formulas IVB and VIB corresponding to the esters of formulas IVB and VIB named following Example 10. The free acids of formulas IVB and VIB can be purified by chromatography over acid washed silica gel or by other conventional means for purifying prostanoic acids.

It is to be noted that in these further examples only those compounds with a 3-hydroxy-5-oxo structure in the 5-member ring (i.e., derived from IVA) will give a product which when treated with base gives a 278 mμ absorption in the U.V.

EXAMPLE 11

Racemic ethyl 7-[5-oxo-2β-(3-oxo-1-octenyl)-3-cyclopenten-1β-yl]heptanoic acid (VB)

Following the procedure of Example 8 but substituting for racemic ethyl 7-[3α-hydroxy-5-oxo-2β-(3-oxooctyl)cyclopent-1β-yl]heptonate (IVA) as starting material a compound of formula IVB, for example:

1. racemic ethyl 7-[3α-hydroxy-5-oxo-2β-(3-oxo-1-octenyl)cyclopent- 1β-yl]heptanoate (IVB),
2. racemic ethyl 3-[3α-hydroxy-5-oxo-2β-(3-oxo-1-octenyl)cyclopent-1β-yl]propionate (IVB),
3. racemic methyl 5-[3α-hydroxy-5-oxo-2β-(3-oxo-1-octenyl)cyclopent-1β-yl]pentanoate (IVB),
4. racemic methyl 3-methyl-5-[3α-hydroxy-5-oxo-2β-(3-oxo-1-octenyl)cyclopent-1β-yl]pentanoate (IVB),
5. racemic ethyl 7-[3α-hydroxy-5-oxo-2β-(3-oxo-1-butenyl)cyclopent-1β-yl]heptanoate (IVB), the free acids corresponding to the above esters, and the like, are productive of:

1. racemic ethyl 7-[5-oxo-2β-(3-oxo-1-octenyl)-3-cyclopenten-1β-yl]heptanoate (VB),
2. racemic ethyl 3-[5-oxo-2β-(3-oxo-1-octenyl)-3-cyclopenten-1β-yl]propionate (VB),
3. racemic methyl 5-[5-oxo-2β-(3-oxo-1-octenyl)-3-cyclopenten-1β-yl]pentanoate (VB),
4. racemic methyl 3-methyl-5-[5-oxo-2β-(3-oxo-1-octenyl)-3-cyclopenten-1β-yl]pentanoate (VB),
5. racemic ethyl 7-[5-oxo-2β-(3-oxo-1-butenyl)-3-cyclopenten-1β-yl]heptanoate (VB), the free acids corresponding to the above esters, and the like.

EXAMPLE 12

Racemic ethyl 7-[3α-hydroxy-5-oxo-2β-(3-hydroxyoctyl) cyclopent-1β-yl]heptanoate (IVC)

A solution of 300 mg. of racemic ethyl 7-[3α-hydroxy-5-oxo-2β-(3-oxooctyl)cyclopent-1β-yl]heptanoate (IVA) in 30 ml. of methanol is cooled in an ice bath and stirred while 0.25 molecular equivalent of sodium borohydride in 100 ml. of cold methanol is added in portions over a 2 minute period. Stirring while cooling with the ice bath is continued for 20 min., then at room temperature for 1 hr. The reaction mixture is then neutralized with dilute aqueous acetic acid and concentrated by evaporation under reduced pressure to about ⅔ volume, and 25 ml. of water is added after which concentration is continued until most of the methanol has been removed. The residual mixture is acidified with dilute hydrochloric acid, and extracted three times with ether. The ether extracts are combined, washed with water, dried, and evaporated under reduced pressure to give a residue comprising racemic ethyl 7-[3α-hydroxy-5-oxo-2β-(3-hydroxyoctyl)cyclopent-1β-yl]heptanoate (IVC), which can be further purified by chromatographing over silica gel, eluting with ethyl acetate to obtain the desired product.

Following the procedure of Example 12 but substituting for racemic ethyl 7-[3α-hydroxy-5-oxo-2β-(3-oxooctyl)cyclopent-1β-yl]heptanoate (IVA) as starting material other compounds of formula IVA and compounds of formulas VA, VIA, IVB, VB and VIB, for example:

1. racemic ethyl 3-[3α-hydroxy-5-oxo-2β-(3-oxooctyl)cyclopent-1β-yl]propionate (IVA),
2. racemic methyl 5-[3α-hydroxy-5-oxo-2β-(3-oxooctyl)cyclopent-1β-yl]pentanoate (IVA),
3. racemic methyl 3-methyl-5-[3α-hydroxy-5-oxo-2β-(3-oxooctyl)cyclopent-1β-yl]pentanoate (IVA),
4. racemic ethyl 7-[3α-hydroxy-5-oxo-2β-(3-oxobutyl)cyclopent-1β-yl]heptanoate (IVA),
5. racemic ethyl 7-[5-oxo-2β-(3-oxooctyl)-3-cyclopenten-1β-yl]heptonate (VA),
6. racemic ethyl 3-[5-oxo-2β-(3-oxooctyl)-3-cyclopenten-1β-yl]propionate (VA),
7. racemic methyl 5-[5-oxo-2β-(3-oxooctyl)-3-cyclopenten-1β-yl]pentanoate (VA),
8. racemic methyl 3-methyl-5-[5-oxo-2β-(3-oxooctyl)-3-cyclopenten-1β-yl]pentanoate (VA),
9. racemic ethyl 7-[5-oxo-2β-(3-oxobutyl)-3-cyclopenten-1β-yl]heptanoate (VA),
10. racemic ethyl 7-[5-oxo-2β-(3-oxooctyl)-cyclopent-1β-yl]heptanoate (VIA),
11. racemic ethyl 3-[5-oxo-2β-(3-oxooctyl)cyclopent-1β-yl]propionate (VIA),
12. racemic methyl 5-[5-oxo-2β-(3-oxooctyl)cyclopent-1β-yl]pentanoate (VIA),
13. racemic methyl 3-methyl-5-[5-oxo-2β-(3-oxooctyl)cyclopent-1β-yl]pentanoate (VIA),
14. racemic ethyl 7-[5-oxo-2β-(3-oxobutyl)cyclopent-1β-yl]heptanoate (VIA),
15. racemic ethyl 7-[3α-hydroxy-5-oxo-2β-(3-oxo-1-octenyl)cyclopent-1β-yl]heptanoate (IVB),
16. racemic ethyl 3-[3α-hydroxy-5-oxo-2β-(3-oxo-1-octenyl)cyclopent-1β-yl]propionate (IVB),
17. racemic methyl 5-[3α-hydroxy-5-oxo-2β-(3-oxo-1-octenyl)cyclopent-1β-yl]pentanoate (IVB),
18. racemic methyl 3-methyl-5-[3α-hydroxy-5-oxo-2β-(3-oxo-1-octenyl)cyclopent-1β-yl]pentanoate (IVB),
19. racemic ethyl 7-[3α-hydroxy-5-oxo-2β-(3-oxo-1-butenyl)cyclopent-1β-yl]heptanoate (IVB),
20. racemic ethyl 7-[5-oxo-2β-(3-oxo-1-octenyl)-3-cyclopenten-1β-yl]heptanoate (VB),
21. racemic ethyl 3-[5-oxo-2β-(3-oxo-1-octenyl)-3-cyclopenten-1β-yl]propionate (VB),
22. racemic methyl 5-[5-oxo-2β-(3-oxo-1-octenyl)-3-cyclopenten-1β-yl]pentanoate (VB), 23. racemic methyl 3-methyl-5-[5-oxo-2β-(3-oxo-1-octenyl)-3-cyclopenten-1β-yl]pentanoate (VB),
24. racemic ethyl 7-[5-oxo-2β-(3-oxo-1-butenyl)-3-cyclopenten-1β-yl]heptanoate (VB),
25. racemic ethyl 7-[5-oxo-2β-(3-oxo-1-octenyl)cyclopent-1β-yl]heptanoate (VIB),
26. racemic ethyl 3-[5-oxo-2β-(3-oxo-1-octenyl)cyclopent-1β-yl]propionate (VIB),
27. racemic methyl 5-[5-oxo-2β-(3-oxo-1-octenyl)cyclopent-1β-yl]pentanoate (VIB),
28. racemic methyl 3-methyl-5-[5-oxo-2β-(3-oxo-1-octenyl)cyclopent-1β-yl]pentanoate (VIB),
29. racemic ethyl 7-[5-oxo-2β-(3-oxo-1-butenyl)cyclopent-1β-yl]heptanoate (VIB), and the like, is productive of 1. racemic ethyl 3-[3α-hydroxy-5-oxo-2β-(3-hydroxyoctyl)cyclopent-1β-yl]propionate (IVC),
2. racemic methyl 5-[3α-hydroxy-5-oxo-2β-(3-hydroxyoctyl)cyclopent-1β-yl]pentanoate (IVC),
3. racemic methyl 3-methyl-5-[3α-hydroxy-5-oxo-2β-(3-hydroxyoctyl)cyclopent-1β-yl]pentanoate (IVC),
4. racemic ethyl 7-[3α-hydroxy-5-oxo-2β-(3-hydroxybutyl)cyclopent-1β-yl]heptanoate (IVC),
5. racemic ethyl 7-[5-oxo-2β-(3-hydroxyoctyl)-3-cyclopenten-1β-yl]heptanoate (VC),
6. racemic ethyl 3-[5-oxo-2β-(3-hydroxyoctyl)-3-cyclopenten-1β-yl]propionate (VC),
7. racemic methyl 5-[5-oxo-2β-(3-hydroxyoctyl)-3-cyclopenten-1β-yl]pentanoate (VC),
8. racemic methyl 3-methyl-5-[5-oxo-2β-(3-hydroxyoctyl)-3-cyclopenten-1β-yl]pentanoate (VC),
9. racemic ethyl 7-[5-oxo-2β-(3-hydroxybutyl)-3-cyclopenten-1β-yl]heptanoate (VC),
10. racemic ethyl 7-[5-oxo-2β-(3-hydroxyoctyl)cyclopent-1β-yl]heptanoate (VIC),
11. racemic ethyl 3-[5-oxo-2β-(3-hydroxyoctyl)cyclopent-1β-yl]propionate (VIC),
12. racemic methyl 5-[5-oxo-2β-(3-hydroxyoctyl)cyclopent-1β-yl] pentanoate (VIC),
13. racemic methyl 3-methyl-5-[5-oxo-2β-(3-hydroxyoctyl)cyclopent-1β-yl]pentanoate (VIC),
14. racemic ethyl 7-[5-oxo-2β-(3-hydroxybutyl)cyclopent-1β-yl]heptanoate (VIC),
15. racemic ethyl 7-[3α-hydroxy-5-oxo-2β-(3-hydroxy-1-octenyl)cyclopent-1β-yl]heptanoate (IVC),
16. racemic ethyl 3-[3α-hydroxy-5-oxo-2β-(3-hydroxy-1-octenyl)cyclopent-1β-yl]propionate (IVC),
17. racemic methyl 5-[3α-hydroxy-5-oxo-2β-(3-hydroxy-1-octenyl)cyclopent-1β-yl]pentanoate (IVC),
18. racemic methyl 3-methyl-5-[3α-hydroxy-5-oxo-2β-(3-hydroxy-1-octenyl)cyclopent-1β-yl]pentanoate (IVC),
19. racemic ethyl 7-[3α-hydroxy-5-oxo-2β-(3-hydroxy-1-butenyl)cyclopent-1β-yl]heptanoate (IVC),
20. racemic ethyl 7-[5-oxo-2β-(3-hydroxy-1-octenyl)-3-cyclopenten-1β-yl]heptanoate (VC),
21. racemic ethyl 3-[5-oxo-2β-(3-hydroxy-1-octenyl)-3-cyclopenten-1β-yl]propionate (VC),
22. racemic methyl 5-[5-oxo-2β-(3-hydroxy-1-octenyl)-3-cyclopenten-1β-yl]pentanoate (VC),
23. racemic methyl 3-methyl-5-[5-oxo-2β-(3-hydroxy-1-octenyl)-3-cyclopenten-1β-yl]pentanoate (VC),
24. racemic ethyl 7-[5-oxo-2β-(3-hydroxy-1-butenyl)-3-cyclopenten-1β-yl]heptanoate (VC),
25. racemic ethyl 7-[5-oxo-2β-(3-hydroxy-1-octenyl)cyclopent-1β-yl]heptanoate (VIC),
26. racemic ethyl 3-[5-oxo-2β-(3-hydroxy-1-octenyl)cyclopent-1β-yl]propionate (VIC),
27. racemic methyl 5-[5-oxo-2β-(3-hydroxy-1-octenyl)cyclopent-1β-yl]pentanoate (VIC),
28. racemic methyl 3-methyl-5-[5-oxo-2β-(3-hydroxy-1-octenyl)cyclopent-1β-yl]pentanoate (VIC),
29. racemic ethyl 7-[5-oxo-2β-(3-hydroxy-1-butenyl)cyclopent-1β-yl]heptanoate (VIC), and the like.

Substituting the free acids of formulas IVA, VA, VIA, IVB, VB and VIB as starting materials in the process of Examples 12, for example racemic 7-[3α-hydroxy-5-oxo-2β-(3-oxooctyl)cyclopent-1β-yl]heptanoic acid (IVA) and the other free acids of formulas IVA, VA, VIA, IVB, VB and VIB corresponding to the esters of formulas IVA, VA, VIA, IVB, VB and VIB named following Example 12 is productive of the free acids of formulas IVC, VC and VIC, for example racemic 7-[3α-hydroxy-5-oxo-2β-(3-hydroxyoctyl)cyclopent-1β-yl]heptanoic acid (IVC) and the other free acids of formulas IVC, VC and VIC corresponding to the esters of formulas IVC, VC and VIC named following Example 12. The free acids of formulas IVC, VC and VIC can be purified by chromatography over acid washed silica gel or by other conventional means for purifying prostanoic acids.

EXAMPLE 13

Racemic ethyl 7-[3α,5α-dihydroxy-2β-(3-hydroxyoctyl)cyclopent-1β-yl]heptanoate (IV D) and racemic ethyl 7-[3α,5β-dihydroxy-2β-(3-hydroxyoctyl)cyclopent-1β-yl]heptanoate (IV D).

A solution of 300 mg. of racemic ethyl 7-[3α-hydroxy-5-oxo-2β-(3-oxooctyl)cyclopent-1β-yl]heptanoate (IV A) in 30 ml. of methanol is cooled in an ice bath and stirred while a cold mixture of 1 g. of sodium borohydride and 100 ml. of methanol is added in portions over a 2-minute period. Stirring while cooling with the ice bath is continued for 20 minutes, then stirring is continued while the mixture is allowed to warm to room temperature. The mixture is then neutralized with dilute aqueous acetic acid and evaporated under reduced pressure to about ⅔ volume, after which 25 ml. of water is added and concentration is continued until most of the methanol has been removed. The residual mixture is acidified with dilute hydrochloric acid and extracted three times with ether. The ether extracts are combined, washed with water, dried, and evaporated under reduced pressure to give a residue comprising racemic ethyl 7-[3α,5α-dihydroxy-2β-(3-hydroxyoctyl)cyclopent-1β-yl]heptanoate (IV D) and racemic ethyl 7-[3α,5β-dihydroxy-2β-(3-hydroxyoctyl)cyclopent-1β-yl]heptanoate (IV D).

The thus-obtained residue is dissolved in ethyl acetate and chromatographed over 30 g. of silica gel. The column is eluted with ethyl acetate taking 30 ml. fractions and the eluate fractions are evaporated. The residues obtained are examined by thin layer chromatography (silica gel developed with ethyl acetate) and the fractions comprising racemic ethyl 7-[3α,5α-dihydroxy-2β-(3-hydroxyoctyl)cyclopent-1β-yl]heptanoate (IV D) are identified by comparison with a reference sample, obtained for example as in Preparation 34. Those fractions forming an elution peak having a similar but distinctly different mobility are combined as racemic ethyl 7-[3α,5β-dihydroxy-2β-(3-hydroxyoctyl)cyclopent-1β-yl]heptanoate (IV D). The 5β-hydroxy compound is eluted after the 5α.

Following the procedure of Example 13 but substituting for racemic ethyl 7-[3α-hydroxy-5-oxo-2β-(3-oxooctyl)cyclopent-1β-yl]heptanoate (IV A) as starting material other compounds of formula IV A and compounds of formulas V A, VI A, IV B, V B, and VI B, for example:

1. racemic ethyl 3-[3α-hydroxy-5-oxo-2β-(3-oxooctyl)cyclopent-1β-yl]propionate (IV A),
2. racemic methyl 5-[3α-hydroxy-5-oxo-2β-(3-oxooctyl)cyclopent-1β-yl]pentanoate (IV A),
3. racemic methyl 3-methyl-5-[3α-hydroxy-5-oxo-2β-(3-oxooctyl)cyclopent-1β-yl]pentanoate (IV A),
4. racemic ethyl 7-[3α-hydroxy-5-oxo-2β-(3-oxobutyl)cyclopent-1β-yl]heptanoate (IV A),
5. racemic ethyl 7-[5-oxo-2β-(3-oxooctyl)-3-cyclopenten-1β-yl]-heptanoate (V A),
6. racemic ethyl 3-[5-oxo-2β-(3-oxooctyl)-3-cyclopenten-1β-yl]propionate (V A),
7. racemic methyl 5-[5-oxo-2β-(3-oxooctyl)-3-cyclopenten-1β-yl]pentanoate (V A),
8. racemic methyl 3-methyl-5-[5-oxo-2β-(3-oxooctyl)-3-cyclopenten-1β-yl]pentanoate (V A),
9. racemic ethyl 7-[5-oxo-2β-(3-oxobutyl)-3-cyclopenten-1β-yl]-heptanoate (V A),
10. racemic ethyl 7-[5-oxo-2β-(3-oxooctyl)cyclopent-1β-yl]-heptanoate (VI A),
11. racemic ethyl 3-[5-oxo-2β-(3-oxooctyl)cyclopent-1β-yl]-propionate (VI A),
12. racemic methyl 5-[5-oxo-2β-(3-oxooctyl)cyclopent-1β-yl]pentanoate (VI A),
13. racemic methyl 3-methyl-5-[5-oxo-2β-(3-oxooctyl)cyclopent-1β-yl]pentanoate (VI A),
14. racemic ethyl 7-[5-oxo-2β-(3-oxobutyl)cyclopent-1β-yl]heptanoate (VI A),
15. racemic ethyl 7-[3α-hydroxy-5-oxo-2β-(3-oxo-1-octenyl)cyclopent-1β-yl]heptanoate (IV B),
16. racemic ethyl 3-[3α-hydroxy-5-oxo-2β-(3-oxo-1-octenyl)cyclopent-1β-yl]propionate (IV B),
17. racemic methyl 5-[3α-hydroxy-5-oxo-2β-(3-oxo-1-octenyl)cyclopent-1β-yl]pentanoate (IV B),
18. racemic methyl 3-methyl-5-[3α-hydroxy-5-oxo-2β-(3-oxo-1-octenyl)cyclopent-1β-yl]pentanoate (IV B),
19. racemic ethyl 7-[3α-hydroxy-5-oxo-2β-(3-oxo-1-butenyl)cyclopent-1β-yl]heptanoate (IV B),
20. racemic ethyl 7-[5-oxo-2β-(3-oxo-1-octenyl)-3-cyclopenten-1β-yl]heptanoate (V B),
21. racemic ethyl 3-[5-oxo-2β-(3-oxo-1-octenyl)-3-cyclopenten-1β-yl]propionate (V B),
22. racemic methyl 5-[5-oxo-2β-(3-oxo-1-octenyl)-3-cyclopenten-1β-yl]pentanoate (V B),
23. racemic methyl 3-methyl-5-[5-oxo-2β-(3-oxo-1-octenyl)-3-cyclopenten-1β-yl]pentanoate (V B),
24. racemic ethyl 7-[5-oxo-2β-(3-oxo-1-butenyl)-3-cyclopenten-1β-yl]heptanoate (V B),
25. racemic ethyl 7-[5-oxo-2β-(3-oxo-1-octenyl)cyclopent-1β-yl]heptanoate (VI B),
26. racemic ethyl 3-[5-oxo-2β-(3-oxo-1-octenyl)cyclopent-1β-yl]propionate (VI B),
27. racemic methyl 5-[5-oxo-2β-(3-oxo-1-octenyl)cyclopent-1β-yl]pentanoate (VI B),
28. racemic methyl 3-methyl-5-[5-oxo-2β-(3-oxo-1-octenyl)cyclopent-1β-yl]pentanoate (VI B),
29. racemic ethyl 7-[5-oxo-2β-(3-oxo-1-butenyl)cyclopent-1β-yl]heptanoate (VI B).

and the like, is productive of 1. racemic ethyl 3-[3α,5α-dihydroxy-2β-(3-hydroxyoctyl)cyclopent-1β-yl]propionate (IV D) and racemic ethyl 3-[3α,5β-dihydroxy-2β-(3-hydroxyoctyl)cyclopent-1β-yl]propionate (IV D),
2. racemic methyl 5-[3α,5α-dihydroxy-2β-(3-hydroxyoctyl)cyclopent-1β-yl]pentanoate (IV D) and racemic methyl 5-[3α,5β-dihydroxy-2β-(3-hydroxyoctyl)cyclopent-1β-yl]pentanoate (IV D),
3. racemic methyl 3-methyl-5-[3α,5α-dihydroxy-2β-(3-hydroxyoctyl)cyclopent-1β-yl]pentanoate (IV D) and racemic methyl 3-methyl-5-[3α,5β-dihydroxy-2β-(3-hydroxyoctyl)cyclopent-1β-yl]pentanoate (IV D),
4. racemic ethyl 7-[3α,5α-dihydroxy-2β-(3-hydroxybutyl)cyclopent-1β-yl]heptanoate (IV D) and racemic ethyl 7-[3α,5β-dihydroxy-2β-(3-hydroxybutyl)cyclopent-1β-yl]heptanoate (IV D),
5. racemic ethyl 7-[5α-hydroxy-2β-(3-hydroxyoctyl)-3-cyclopenten-1β-yl]heptanoate (V D) and racemic ethyl 7-[5β-hydroxy-2β-(3-hydroxyoctyl)-3-cyclopenten-1β-yl]heptanoate (V D),
6. racemic ethyl 3-[5α-hydroxy-2β-(3-hydroxyoctyl)-3-cyclopenten-1β-yl]propionate (V D) and racemic ethyl 3-[5β-hydroxy-2β-(3-hydroxyoctyl)-3-cyclopenten-1β-yl]propionate (V D),
7. racemic methyl 5-[5α-hydroxy-2β-(3-hydroxyoctyl)-3-cyclopenten-1β-yl]pentanoate (V D) and racemic methyl 5-[5β-hydroxy-2β-(3-hydroxyoctyl)-3-cyclopenten-1β-yl]pentanoate (V D),
8. racemic methyl 3-methyl-5-[5α-hydroxy-2β-(3-hydroxyoctyl)-3-cyclopenten-1β-yl]pentanoate (V D) and racemic methyl 3-methyl-5-[5β-hydroxy-2β-(3-hydroxyoctyl)-3-cyclopenten-1β-yl]pentanoate (V D),
9. racemic ethyl 7-[5α-hydroxy-2β-(3-hydroxybutyl)-3-cyclopenten-1β-yl]heptanoate (V D) and racemic ethyl 7-[5β-hydroxy-2β-(3-hydroxybutyl)-3-cyclopenten-1β-yl]heptanoate (V D),
10. racemic ethyl 7-[5α-hydroxy-2β-(3-hydroxyoctyl)cyclopent-1β-yl]heptanoate (VI D) and racemic ethyl 7-[5β-hydroxy-2β-(3-hydroxyoctyl)cyclopent-1β-yl]heptanoate (VI D),
11. racemic ethyl 3-[5α-hydroxy-2β-(3-hydroxyoctyl)cyclopent-1β-yl]propionate (VI D) and racemic ethyl 3-[5β-hydroxy-2β-(3-hydroxyoctyl)cyclopent-1β-yl]propionate (VI D),
12. racemic methyl 5-[5α-hydroxy-2β-(3-hydroxyoctyl)cyclopent-1β-yl]pentanoate (VI D) and racemic methyl 5-[5β-hydroxy-2β-(3-hydroxyoctyl)cyclopent-1β-yl]pentanoate (VI D),
13. racemic methyl 3-methyl-5-[5α-hydroxy-2β-(3-hydroxyoctyl)cyclopent-1β-yl]pentanoate (VI D) and racemic methyl 3-methyl-5-[5β-hydroxy-2β-(3-hydroxyoctyl)cyclopent-1β-yl]pentanoate (VI D),
14. racemic ethyl 7-[5α-hydroxy-2β-(3-hydroxybutyl)cyclopent-1β-yl]heptanoate (VI D) and racemic ethyl 7-[5β-hydroxy-2β-(3-hydroxybutyl)cyclopent-1β-yl]heptanoate (VI D),
15. racemic ethyl 7-[3α,5α-dihydroxy-2β-(3-hydroxy-1-octenyl)cyclopent-1β-yl]heptanoate (IV D) and racemic ethyl 7-[3α,5β-dihydroxy-2β-(3-hydroxy-1-octenyl)cyclopent-1β-yl]heptanoate (IV D),
16. racemic ethyl 3-[3α,5α-dihydroxy-2β-(3-hydroxy-1-octenyl)cyclopent-1β-yl]propionate (IV D) and racemic ethyl 3-[3α,5β-dihydroxy-2β-(3-hydroxy-1-octenyl)cyclopent-1β-yl]propionate (IV D), 17. racemic methyl 5-[3α,5α-dihydroxy-2β-(3-hydroxy-1-octenyl)cyclopent-1β-yl]pentanoate (IV D) and racemic methyl 5-[3α,5β-dihydroxy-2β-(3-hydroxy-1-octenyl)cyclopent-1β-yl]pentanoate (IV D), 18. racemic methyl 3-methyl-5-[3α,5α-dihydroxy-2β-(3-hydroxy-1-octenyl)cyclopent-1β-yl]pentanoate (IV D) and racemic methyl 3-methyl-5-[3α,5β-dihydroxy-2β-(3-hydroxy-1-octenyl)cyclopent-1β-yl]pentanoate (IV D), 19. racemic ethyl 7-[3α,5α-dihydroxy-2β-(3-hydroxy-1-butenyl)cyclopent-1β-yl]heptanoate (IV D) and racemic ethyl 7-[3α,5β-dihydroxy-2β-(3-hydroxy-1-butenyl)cyclopent-1β-yl]heptanoate (IV D), 20. racemic ethyl 7-[5α-hydroxy-2β-(3-hydroxy-1-octenyl)-3-cyclopenten-1β-yl]heptanoate (V D) and racemic ethyl 7-[5β-hydroxy-2β-(3-hydroxy-1-octenyl)-3-cyclopenten-1β-yl]heptanoate (V D), 21. racemic ethyl 3-[5α-hydroxy-2β-(3-hydroxy-1-octenyl)-3-cyclopenten-1β-yl]propionate (V D) and racemic ethyl 3-[5β-hydroxy-2β-(3-hydroxy-1-octenyl)-3-cyclopenten-1β-yl]propionate (V D), 22. racemic methyl 5-[5α-hydroxy-2β-(3-hydroxy-1-octenyl)-3-cyclopenten-1β-yl]pentanoate (V D) and racemic methyl 5-[5β-hydroxy-2β-(3-hydroxy-1-octenyl)-3-cyclopenten-1β-yl]pentanoate (V D), 23. racemic methyl 3-methyl-5-[5α-hydroxy-2β-(3-hydroxy-1-octenyl)-3-cyclopenten-1β-yl]pentanoate (V D) and racemic methyl 3-methyl-5-[5β-hydroxy-2β-(3-hydroxy-1-octenyl)-3-cyclopenten-1β-yl]pentanoate (V D), 24. racemic ethyl 7-[5α-hydroxy-2β-(3-hydroxy-1-butenyl)-3-cyclopenten-1β-yl]heptanoate (V D) and racemic ethyl 7-[5β-hydroxy-2β-(3-hydroxy-1-butenyl)-3-cyclopenten-1β-yl]heptanoate (V D), 25. racemic ethyl 7-[5α-hydroxy-2β-(3-hydroxy-1-octenyl)cyclopent-1β-yl]heptanoate (VI D) and racemic ethyl 7-[5β-hydroxy-2β-(3-hydroxy-1-octenyl)cyclopent-1β-yl]heptanoate (VI D), 26. racemic ethyl 3-[5α-hydroxy-2β-(3-hydroxy-1-octenyl)cyclopent-1β-yl]propionate (VI D) and racemic ethyl 3-[5β-hydroxy-2β-(3-hydroxy-1-octenyl)cyclopent-1β-yl]propionate (VI D), 27. racemic methyl 5-[5α-hydroxy-2β-(3-hydroxy-1-octenyl)cyclopent-1β-yl]pentanoate (VI D) and racemic methyl 5-[5β-hydroxy-2β-(3-hydroxy-1-octenyl)cyclopent-1β-yl]pentanoate (VI D), 28. racemic methyl 3-methyl-5-[5α-hydroxy-2β-(3-hydroxy-1-octenyl)cyclopent-1β-yl]pentanoate (VI D) and racemic methyl 3-methyl-5-[5β-hydroxy-2β-(3-hydroxy-1-octenyl)cyclopent-1β-yl]pentaonate (VI D), 29. racemic ethyl 7-[5α-hydroxy-2β-(3-hydroxy-1-butenyl)cyclopent-1β-yl]heptanoate (VI D) and racemic ethyl 7-[5β-hydroxy-2β-(3-hydroxy-1-butenyl)cyclopent-1β-yl]heptanoate (VI D), and the like.

Substituting the free acids of formulas IV A, V A, VI A, IV B, V B and VI B as starting materials in the process of Example 13, for example racemic 7-[3α-hydroxy-5-oxo-2β-(3-oxooctyl)cyclopent-1β-yl]heptanoic acid (IV A) and the other free acids of formulas IV A, V A, VI A, IV B, V B, and VI B corresponding to the esters of formulas IV A, V A, VI A, IV B, V B and VI B named following Example 13 is productive of the free acids of formulas IV D, V D and VI D, for example racemic 7-[3α,5α(and 5β)-dihydroxy-2β-(3-hydroxyoctyl)cyclopent-1β-yl]heptanoic acid (IV D) and the other free acids of formulas IV D, V D and VI D corresponding to the esters of formulas IV D, V D and VI D named following Example 13. The free acids of formulas IV D, V D and VI D can be purified by chromatography over acid washed silica gel or by other conventional means for purifying prostanoic acids.

EXAMPLE 14

Racemic ethyl 7-(4,4aα,5,6,7,7aβ-hexahydro-2-pentyl-6-oxocyclopenta[b]pyran-5-ylidene)-3,5-heptadienoate (III B), racemic ethyl 7-(2,3,4,4aα,5,6,7,7aβ-octahydro-2-pentylidene-6-oxocyclopenta[b]pyran-5-ylidene)-3,5-heptadienoate (III B') and racemic ethyl 7-[3α-hydroxy-5-oxo-2β-(3-oxooctyl)cyclopentylidene]-3,5-heptadienoate (III E)

A solution of 6.8 g. of a mixture comprising racemic ethyl 7-(4,4aα,5,6,7,7aβ-hexahydro-6α-hydroxy-2-pentylcyclopenta[b]-pyran-5β-yl)-2,4,6-heptatrienoate (II B) and racemic ethyl 7-(2,3,4,4aα,5,6,7,7aβ-octahydro-6α-hydroxy-2-pentylidenecyclopenta[b]pyran-5β-yl)-2,4,6-heptatrienoate (II B') in a mixture of 30 ml. of anhydrous dimethyl sulfoxide, 30 ml. of benzene, 1.6 ml. of pyridine, and 0.8 ml. of trifluoroacetic acid is prepared and stirred under nitrogen at room temperature (about 25° C.) while 12.4 g. of dicyclohexylcarbodiimide is added. Stirring is continued for about 20 hours. Ether is then added followed by a solution of 5.4 g. of oxalic acid in 50 ml. of methanol. Stirring is continued for another hour, then about 600 ml. of water is added and the mixture is filtered to remove the insoluble dicyclohexylurea. The organic phase in the filtrate is separated and washed with saturated aqueous sodium bicarbonate solution, then with water, and dried over anhydrous sodium sulfate. The thus-obtained solution is evaporated under reduced pressure to give a residue comprising racemic ethyl 7-(4,4aα,5,6,7,7aβ-hexahydro-2-pentyl-6-oxocyclopenta[b]pyran-5-ylidene)-3,5-heptadienoate (III B), racemic ethyl 7-(2,3,4,4aα,5,6,7,7aβ-octahydro-2-pentylidene-6-oxocyclopenta[b]-pyran-5-ylidene)-3,5-heptadienoate (III B'), and racemic ethyl 7-[3α-hydroxy-5-oxo-2β-(3-oxooctyl)cyclopentylidene]-3,5-heptadienoate (III E). The products of formulas III B and III B' can be separated from the product of formula III E by chromatography over silica gel using increasing percentages of ethyl acetate in cyclohexane for elution. The fractions are identified by their characteristic behavior on thin layer chromatography and by their infrared spectra. When only racemic ethyl 7-[3α-hydroxy-5-oxo-2β-(3-oxooctyl)cyclopentylidene]-3,5-heptadienoate (III E) is desired, the residue comprising racemic ethyl 7-(4,4aα,5,6,7,7aβ-hexahydro-6α-hydroxy-2-pentylcyclopenta[b]pyran-5-ylidene)-3,5-heptadienoate (III B), the corresponding compound of formula III B' and racemic ethyl 7-[3α-hydroxy-5-oxo-2β-(3-oxooctyl)cyclopentylidene]-3,5-heptadienoate (III E) is dissolved in about 100 ml. of acetone and 10 ml. of 0.1 N hydrochloric acid is added. The mixture is allowed to stand about 1 hour at room temperature then is neutralized with aqueous sodium bicarbonate and evaporated under reduced pressure until most of the acetone is removed. The residue is extracted with methylene chloride and the methylene chloride extract is evaporated under reduced pressure to give a residue comprising racemic ethyl 7-[3α-hydroxy-5-oxo-2β-(3-oxooctyl)cyclopentylidene]-3,5-heptadienoate (III E), which can be further purified by chromatography over silica gel as described above.

Following the procedure of Example 14 but substituting for racemic ethyl 7-(4,4aα,5,6,7,7aβ-hexahydro-6α-hydroxy-2-pentylcyclopenta[b]pyran-5β-yl)-2,4,6-heptatrienoate (II B) as starting material other compounds of formula II B and II B', for example:

1. racemic ethyl (4,4aα,5,6,7,7aβ-hexahydro-6α-hydroxy-2-pentylcyclopenta[b]pyran-5β-yl)acrylate (II B),
2. racemic methyl 5-(4,4aα,5,6,7,7aβ-hexahydro-6α-hydroxy-2-pentylcyclopenta[b]pyran-5β-yl)-2,4-pentadienoate (II B),
3. racemic methyl 3-methyl-5-(4,4aα,5,6,7,7aβ-hexahydro-6α-hydroxy-2-pentylcyclopenta[b]pyran-5β-yl)-2,4-pentadienoate (II B),
4. racemic ethyl 7-(4,4aα,5,6,7,7aβ-hexahydro-6α-hydroxy-2-methylcyclopenta[b]pyran-5β-yl)-2,4,6-heptatrienoate (II B), and the corresponding compounds of formula II B' and the like, is productive of:

1. racemic ethyl 3-(4,4aα,5,6,7,7aβ-hexahydro-2-pentyl-6-oxocyclopenta[b]pyran-5-ylidene)propionate (III B) and racemic ethyl 3-[3α-hydroxy-5-oxo-2β-(3-oxooctyl)cyclopentylidene]propionate (III E),
2. racemic methyl 5-(4,4aα,5,6,7,7aβ-hexahydro-2-pentyl-6-oxocyclopenta[b]pyran-5-ylidene)-3-pentanoate (III B) and racemic methyl 5-[3α-hydroxy-5-oxo-2β-(3-oxooctyl)cyclopentylidene]-3-pentenoate (III E),
3. racemic methyl 3-methyl-5-(4,4aα,5,6,7,7aβ-hexahydro-2-pentyl-6-oxocyclopenta[b]pyran-5-ylidene)-3-pentenoate (III B) and racemic methyl 3-methyl-5-[3α-hydroxy-5-oxo-2β-(3-oxooctyl)cyclopentylidene]-3-pentenoate (III E),
4. racemic ethyl 7-(4,4aα,5,6,7,7aβ-hexahydro-2-methyl-6-oxocyclopenta[b]pyran-5-ylidene)-3,5-heptadienoate (III B) and racemic ethyl 7-[3α-hydroxy-5-oxo-2β-(3-oxobutyl)cyclopentylidene]-3,5-heptadienoate (III E), and the corresponding compounds of formula III B', and the like.

EXAMPLE 15

Racemic ethyl 7-[3α-hydroxy-5-oxo-2β-(3-oxooctyl)cyclopent-1α-yl]heptanoate (III D)

A solution of 2.50 g. of racemic ethyl 7-[3α-hydroxy-5-oxo-2β-(3-oxooctyl)cyclopentylidene]-3,5-heptadienoate (III E) in 50 ml. of ethanol is hydrogenated in an atmospheric pressure hydrogenator in the presence of 0.2 g. of 5% rhodium on alumina catalyst. After about the theoretical amount of hydrogen has been absorbed, hydrogenation is stopped. The catalyst is removed by filtration and the filtrate is evaporated under diminished pressure to give a residue comprising racemic ethyl 7-[3α-hydroxy-5-oxo-2β-(3-oxooctyl)-cyclopent-1α-yl]heptanoate (III D). The residue thus obtained is dissolved in 1:1 cyclohexane-ethyl acetate and chromatographed over 150 g. of silica gel, eluting with 1:1 cyclohexane-ethyl acetate. Those fractions which, after evaporation of the solvent, show the presence of ethyl 7-[3α-hydroxy-5-oxo-2β-(3-oxooctyl)cyclopent-1α-yl]heptanoate (III D) by infrared analysis and thin layer chromatography are combined.

Following the procedure of Example 15 but substituting for racemic ethyl 7-[3α-hydroxy-5-oxo-2β-(3-oxooctyl)cyclopentylidene]-3,5-heptadienoate (III E) as starting material other compounds of formula III E, for example:

1. racemic ethyl 3-[3α-hydroxy-5-oxo-2β-(3-oxooctyl)cyclopentylidene]propionate (III E),
2. racemic methyl 5-[3α-hydroxy-5-oxo-2β-(3-oxooctyl)cyclopentylidene]-3-pentenoate (III E),
3. racemic methyl 3-methyl-5-[3α-hydroxy-5-oxo-2β-(3-oxooctyl)cyclopentylidene]-3-pentenoate (III E),
4. racemic ethyl 7-[3α-hydroxy-5-oxo-2β-(3-oxobutyl)cyclopentyldene]-3,5-heptadienoate (III E), and the like, is productive of:

1. racemic ethyl 3-[3α-hydroxy-5-oxo-2β-(3-oxooctyl)cyclopent-1α-yl]propionate (III D),
2. racemic methyl 5-[3α-hydroxy-5-oxo-2β-(3-oxooctyl)cyclopent-1α-yl]pentanoate (III D),
3. racemic methyl 3-methyl-5-[3α-hydroxy-5-oxo-2β-(3-oxooctyl)cyclopent-1α-yl]pentanoate (III D),
4. racemic ethyl 7-[3α-hydroxy-5-oxo-2β-(3-oxobutyl)cyclopent-1α-yl]heptanoate (III D), and the like.

EXAMPLE 16

Racemic ethyl 7-(4,4aα,5,6,7,7aβ-hexahydro-6-oxo-2-pentylcyclopenta[b]pyran-5α-yl)heptanoate (III C)

A solution of 10.0 g. of racemic ethyl 7-(4,4aα,5,6,7,7aβ-hexahydro-6-oxo-2-pentylcyclopenta[b]pyran-5β-yl)heptanoate (III A) in 3500 ml. of dioxane is irradiated in a quartz, water cooled reactor using an unfiltered high pressure Hanovia mercury vapor lamp until substantial isomerization has taken place as judged by analysis of aliquots by thin layer chromatography. The solvent is then removed by evaporation under reduced pressure leaving a residue comprising racemic ethyl 7-(4,4aα,5,6,7,7aβ-hexahydro-6-oxo-2-pentylcyclopenta[b]pyran-5α-yl)heptanoate (III C) which can be further purified by chromatography over silica gel.

Alternatively, heating a solution of 1 g. of racemic ethyl 7-(4,4aα,5,6,7,7aβ-hexahydro-6-oxo-2-pentylcyclopenta[b]pyran-5β-yl)heptanoate (III A) in 50 ml. of ethanol in the presence of about 250 mg. of pre-reduced 30% palladium on carbon catalyst under reflux under an atmosphere of nitrogen is also productive of racemic ethyl 7-(4,4aα,5,6,7,7aβ-hexahydro-6-oxo-2-pentylcyclopenta[b]pyran-5α-yl)heptanoate (III C). Raney nickel, platinum, or cobalt hydrocarbonyl can be substituted for the palladium on carbon catalyst.

Following the procedure of Example 16, but substituting for racemic ethyl 7-(4,4aα,5,6,7,7aβ-hexahydro-6-oxo-2-pentylcyclopenta[b]pyran-5β-yl)heptanoate (III A) as starting material a mixture comprising racemic ethyl 7-(4,4aα,5,6,7,7aβ-hexahydro-6-oxo-2-pentylcyclopenta[b]pyran-5β-yl)heptanoate (III A) and racemic ethyl 7-(2,3,4,4aα,5,6,7,7aβ-octahydro-6-oxo- 2-pentylidenecyclopenta[b]pyran-5β-yl)heptanoate (III A') is productive of a mixture comprising racemic ethyl 7-(4,4aα,5,6,7,7aβ-hexahydro-6-oxo-2-pentylcyclopenta[b]pyran-5α-yl)heptanoate (III C) and racemic ethyl 7-(2,3,4,4aα,5,6,7,7aβ-octahydro-6-oxo-2-pentylidenecyclopenta[b]pyran-5α-yl)heptanoate (III C').

Following the procedure of Example 16, but substituting for racemic ethyl 7-(4,4aα,5,6,7,7aβ-hexahydro-6-oxo-2-pentylcyclopenta[b]pyran-5β-yl)heptanoate (III A) as starting material other compounds of formula III A and III A', for example:

1. racemic ethyl 3-(4,4aα,5,6,7,7aβ-hexahydro-6-oxo-2-pentylcyclopenta[b]pyran-5β-yl)propionate (III A),
2. racemic methyl 5-(4,4aα,5,6,7,7aβ-hexahydro-6-oxo-2-pentylcyclopenta[b]pyran-5β-yl)pentanoate (III A),
3. racemic methyl 3-methyl-5-(4,4aα,5,6,7,7aβ-hexahydro-6-oxo-2-pentylcyclopenta[b]pyran-5β-yl)pentanoate (III A),
4. racemic ethyl 7-(4,4aα,5,6,7,7aβ-hexahydro-6-oxo-2-methylcyclopenta[b]pyran-5β-yl)heptanoate (III A), the corresponding compounds designated III A', and the like, is productive of:

1. racemic ethyl 3-(4,4aα,5,6,7,7aβ-hexahydro-6-oxo-2-pentylcyclopenta[b]pyran-5α-yl)propionate (III C),
2. racemic methyl 5-(4,4aα,5,6,7,7aβ-hexahydro-6-oxo-2-pentylcyclopenta[b]pyran-5α-yl)pentanoate (III C),
3. racemic methyl 3-methyl-5-(4,4aα,5,6,7,7aβ-hexahydro-6-oxo-2-pentylcyclopenta[b]pyran-5α-yl)pentanoate (III C),
4. racemic ethyl 7-(4,4aα,5,6,7,7aβ-hexahydro-6-oxo-2-methylcyclopenta[b]pyran-5α-yl)heptanoate (III C), the corresponding compounds designated III C', and the like.

EXAMPLE 17

Racemic ethyl 7-[3α-hydroxy-5-oxo-2β-(3-oxooctyl)cyclopent-1α-yl]heptanoate (III D)

Following the procedure of Example 5 but substituting for racemic ethyl 7-(4,4aα,5,6,7,7aβ-hexahydro-6-oxo-2-pentylcyclopenta[b]pyran-5β-yl)heptanoate (III A) and the corresponding compound designated III A' as starting material racemic ethyl 7-(4,4aα,5,6,7,7aβ-hexahydro-6-oxo-2-pentylcyclopenta[b]pyran-5α-yl)heptanoate (III C) and the corresponding compound designated III C' is productive of racemic ethyl 7-[3α-hydroxy-5-oxo-2β-(3-oxooctyl)cyclopent-1α-yl]heptanoate (III D).

In like manner, following the procedure of Example 5 but substituting as starting material other compounds of formula III C and III C', for example those named following Example 16, is productive of the corresponding compounds of formula III D.

EXAMPLE 18

Racemic 4-butyl-3a,4,5,6,7,7aα-hexahydro-2,5-dioxo-1β-indaneheptanoic acid (VII) and bisoxime A solution of 125 mg. of racemic 7-[3α-hydroxy-5-oxo-2β-(3-oxooctyl)cyclopent-1β-yl]-heptanoic acid (IVA) in 10 ml. of ethanol was mixed with 10 ml. of 1 N aqueous sodium hydroxide and the mixture was heated at 80° C. for 2 hrs. under a nitrogen atmosphere, then was concentrated under reduced pressure until most of the ethanol had been removed. The remaining solution was made acid with dilute hydrochloric acid and extracted with ethyl acetate. The ethyl acetate extract was washed with aqueous sodium chloride, dried, and evaporated under diminished pressure to give 116 mg. of a residue comprising racemic 4-butyl-3a,4,5,6,7,7aα-hexahydro-2,5-dioxo-1β-indaneheptanoic acid (VII). The thus obtained residue was dissolved in benzene and chromatographed over silica gel. Elution with 20% ethyl acetate—80% benzene and evaporation of the eluates gave racemic 4-butyl-3a,4,5,6,7,7aα-hexahydro-2,5-dioxo-1β-indaneheptanoic acid (VII) having the following analysis:

I. R. (CH$_2$Cl$_2$ solution): Principle bands at 3400, 3150, 2680, 1750, 1720 and 1245 cm$^{-1}$. N.M.R. Principal bands: 53 c.p.s. (triplet) and 138 c.p.s. (broad multiplet).

A solution of 173 mg. of racemic 4-butyl-3a,4,5,6,7aα-hexahydro-2,5-dioxo-1β-indaneheptanoic acid (VII) in 2 ml. of methanol was mixed with a solution of 350 mg. of hydroxylamine hydrochloride and 400 mg. of sodium acetate in a mixture of 2 ml. of methanol and 2 ml. of water and allowed to stand overnight at room temperature. A white crystalline precipitate separated. The mixture was chilled and the precipitate was collected by filtration, washed with aqueous methanol and dried. The thus obtained product was recrystallized from aqueous methanol to give racemic 4-butyl-3a,4,5,6,7,7aα-hexahydro-2,5-dioxo-1β-indaneheptanoic acid bisoxime as fine needles melting at 198°–200° C. (dec.) and having the following analysis:

Calcd. for C$_{20}$H$_{34}$O$_4$N$_2$: C, 65.54; H, 9.35; N, 7.65 Found: C, 65.17; H, 9.35; N, 7.46. I.R.: Principal bands (Nujol) at 3250, 3130, 2620, 2540, 1695, 1660, 1290, 1205, 955, 940, and 928 cm$^{-1}$.

Racemic 4-butyl-3a,4,5,6,7,7aα-hexahydro-2,5-dioxo-1β-indaneheptanoic acid has CNS depressant activity and is useful as a sedative for mammals, including humans. It can be administered orally or parenterally in the dosage forms ordinarily employed for such administration.

Following the procedure of Example 18, but substituting for racemic 7-[3α-hydroxy-5-oxo-2β-(3-oxooctyl)cyclopent-1β-yl]heptanoic acid (IVA) as starting material other compounds of formula IVA, for example:

1. racemic 3-[3α-hydroxy-5-oxo-2β-(3-oxooctyl)-cyclopent-1β-yl]propionic acid (IVA),
2. racemic 5-[3α-hydroxy-5-oxo-2β-(3-oxooctyl)-cyclopent-1β-yl]pentanoic acid (IVA),
3. racemic 3-methyl-5-[3α-hydroxy-5-oxo-2β-(3-oxooctyl)cyclopent-1β-yl]pentanoic acid (IVA),
4. racemic 7-[3α-hydroxy-5-oxo-2β-(3-oxobutyl)-cyclopent-1β-yl]heptanoic acid (IVA), and the like is productive of 1. racemic 4-butyl-3a,4,5,6,7,7aα-hexahydro-2,5-dioxo-1β-indanepropionic acid (VII),
2. racemic 4-butyl-3a,4,5,6,7,7aα-hexahydro-2,5,-dioxo-1β-indanepentanoic acid (VII),
3. racemic 3-methyl-4-butyl-3a,4,5,6,7,7aα-hexahydro-2,5-dioxo-1β-indanepentanoic acid (VII),
4. racemic 3aα,4,5,6,7,7aα-hexahydro-2,5-dioxo-1β-indaneheptanoic acid (VII), and the like.

EXAMPLE 19

Racemic
7[5-oxo-2β-(3-oxooctyl)-3-cyclopenten-(1β-yl]heptanoic acid (VA).

Following the procedure of Preparation 32 but substituting for racemic ethyl 7-[3α,5α-dihydroxy-2β-(3-oxooctyl)cyclopent-1β-yl]heptanoate (1B) as starting material racemic ethyl 7-[5-oxo-2β-(3-oxooctyl)-3-cyclopenten-1β-yl]-heptanoate (VA) is productive of racemic 7-[5-oxo-2β-(3-oxooctyl)-3-cyclopenten-1β-yl]heptanoic acid (VA).

In like manner, substituting other esters of formula VA and esters of formulas VIA, VB, VIB, VC, VIC, VD, VID, IIIE, and IIID for example:

1. racemic ethyl 3-[5-oxo-2β-(3-oxooctyl)-3-cyclopenten-1β-yl]propionate (VA),
2. racemic methyl 5-[5-oxo-2β-(3-oxooctyl)-3-cyclopenten-1β-yl]pentanoate (VA),
3. racemic methyl 3-methyl-5-[5-oxo-2β-(3-oxooctyl)-3-cyclopenten-1β-yl]pentanoate (VA),
4. racemic ethyl 7-[5-oxo-2β-(3-oxobutyl)-3-cyclopenten-1β-yl]heptanoate (VA),
5. racemic ethyl 7-[5-oxo-2β-(3-oxooctyl)-cyclopent-1β-yl]heptanoate (VIA),
6. racemic ethyl 3-[5-oxo-2β-(3-oxooctyl)-cyclopent-1β-yl]propionate (VIA),
7. racemic methyl 5-[5-oxo-2β-(3-oxooctyl)-cyclopent-1β-yl]pentanoate (VIA),
8. racemic methyl 3-methyl-[5-oxo-2β-(3-oxooctyl)-cyclopent-1β-yl]pentanoate (VIA),
9. racemic ethyl 7-[5-oxo-2β-(3-oxobutyl)-cyclopent-1β-yl]heptanoate (VIA),
10. racemic ethyl 7-[5-oxo-2β-(3-oxo-1-octenyl)-3-cyclopenten-1β-yl]heptanoate (VB),
11. racemic ethyl 3-[5-oxo-2β-(3-oxo-1-octenyl)-3-cyclopenten-1β-yl]propionate (VB),
12. racemic methyl 5-[5-oxo-2β-(3-oxo-1-octenyl)-3-cyclopenten-1β-yl]pentanoate (VB),
13. racemic methyl 3-methyl-5-[5-oxo-2β-(3-oxo-1-octenyl)-3-cyclopenten-1β-yl]pentanoate (VB),
14. racemic ethyl 7-[5-oxo-2β-(3-oxo-1-butenyl)-3-cyclopenten-1β-yl]heptanoate (VB),
15. racemic ethyl 7-[5-oxo-2β-(3-oxo-1-octenyl)-cyclopent-1β-yl]heptanoate (VIB),
16. racemic ethyl 3-[5-oxo-2β-(3-oxo-1-octenyl)-cyclopent-1β-yl]propionate (VIB),
17. racemic methyl 5-[5-oxo-2β-(3-oxo-1-octenyl)-cyclopent-1β-yl]pentanoate (VIB),
18. racemic methyl 3-methyl-5-[5-oxo-2β-(3-oxo-1-octenyl) cyclopent-1β-yl]pentanoate (VIB),
19. racemic ethyl 7-[5-oxo-2β-(3-oxo-1-butenyl)-cyclopent-1β-yl]heptanoate (VIB),
20. racemic ethyl 7-[5-oxo-2β-(3-hydroxyoctyl)-3-hydroxyoctyl)-3-cyclopenten-1β-yl]heptanoate (VC),
21. racemic ethyl 3-[5-oxo-2β-(3-hydroxyoctyl)- 3-cyclopenten-1β-yl]propionate (VC),
22. racemic methyl 5-[5-oxo-2β(3-hydroxyoctyl)-3-cyclopenten-1β-yl]pentanoate (VC),
23. racemic methyl 3-methyl-5-[5-oxo-2β-(3-hydroxyoctyl)-3-cyclopenten-1β-yl]pentanoate (VC),
24. racemic ethyl 7-[5-oxo-2β-(3-hydroxybutyl)-3-cyclopenten-2β-yl]heptanoate (VC),
25. racemic ethyl 7-[5-oxo-2β-(3-hydroxyoctyl)-cyclopent-1β-yl]heptanoate (VIC),
26. racemic ethyl 3-[5-oxo-2β-(3-hydroxyoctyl)-cyclopent-1β-yl]propionate (VIC),
27. racemic methyl 5-[5-oxo-2β-(3-hydroxyoctyl)-cyclopent-1β-yl]pentanoate (VIC),
28. racemic methyl 3-methyl-5-[5-oxo-2β-(3-hydoxyoctyl)-cyclopent-1β-yl]pentanoate (VIC),
29. racemic ethyl 7-[5-oxo-2β-(3-hydroxybutyl)-cyclopent-1β-yl]heptanoate (VIC),
30. racemic ethyl 7-[5-oxo-2β-(3-hydroxy-1-octenyl)-3-cyclopenten-1β-yl]heptanoate (VC),
31. racemic ethyl 3-[5-oxo-2β-(3-hydroxy-1-octenyl)-3-cyclopenten-1β-yl]propionate (VC),
32. racemic methyl 5-[5-oxo-2β-(3-hydroxy-1-octenyl)-3-cyclopenten-1β-yl]pentanoate (VC),
33. racemic methyl 3-methyl-5-[5-oxo-1β-(3-hydroxy-1-octenyl)-3-cyclopenten-1β-yl]pentanoate (VC),
34. racemic ethyl 7-[5-oxo-2β-(3-oxo-1-butenyl)-3-cyclopenten-1β-yl]heptanoate (VC),
35. racemic ethyl 7-[5-oxo-2β-(3-oxo-1-octenyl)-cyclopent-1β-yl]heptanoate (VIC),
36. racemic ethyl 3-[5-oxo-2β-(3-oxo-1-octenyl)-cyclopent-1β-yl]propionate (VIC),
37. racemic methyl 5-[5-oxo-2β(3-oxo-1-octenyl)-cyclopent-1β-yl]pentanoate (VIC),
38. racemic methyl 3-methyl-5-[5-oxo-2β-(3-oxo-1-octenyl)cyclopent-1β-yl]pentanoate (VIC),
39. racemic ethyl 7-[5-oxo-2β-(3-oxo-1-butenyl)-cyclopent-1β-yl]heptanoate (VIC),
40. racemic ethyl 7-[5α-hydroxy-2β-(3-hydroxyoctyl)-3-cyclopenten-1β-yl]heptanoate (VD),
41. racemic ethyl 7-[5β-hydroxy-2β-(3-hydroxyoctyl)-3-cyclopenten-1β-yl]heptanoate (VD),
42. racemic ethyl 3-[5α-hydroxy-2β-(3-hydroxyoctyl)-3-cyclopenten-1β-yl]propionate (VD),
43. racemic ethyl 3-[5β-hydroxy-2β-(3-hydroxyoctyl)-3-cyclopenten-1β-yl]propionate (VD),
44. racemic methyl 5-[5α-hydroxy-2β-(3-hydroxyoctyl)-3-cyclopenten-1β-yl]pentanoate (VD),
45. racemic methyl 5-[5β-hydroxy-2β-(3-hydroxyoctyl)-3-cyclopenten-1β-yl]pentanoate (VD),
46. racemic methyl 3-methyl-5-[5α-hydroxy-2β-(3-hydroxyoctyl)-3-cyclopenten-1β-yl]pentanoate (VD),
47. racemic methyl 3-methyl-5-[5β-hydroxy-2β-(3-hydroxyoctyl)-3-cyclopenten-1β-yl]pentanoate (VD),
48. racemic ethyl 7-[5α-hydroxy-2β-(3-hydroxybutyl-3-cyclopenten-1β-yl]heptanoate (VD),
49. racemic ethyl 7-[5β-hydroxy-2β-(3-hydroxybutyl)-3-cyclopenten-1β-yl]heptanoate (VD),
50. racemic ethyl 7-[5α-hydroxy-2β-(3-hydroxyoctyl)-cyclopent-1β-yl]heptanoate (VID),
51. racemic ethyl 7-[5β-hydroxy-2β-(3-hydroxyoctyl)-cyclopent-1β-yl]heptanoate (VID),
52. racemic ethyl 3-[5α-hydroxy-2β-(3-hydroxyoctyl)-cyclopent-1β-yl]propionate (VID),
53. racemic ethyl 3-[5β-hydroxy-2β-(3-hydroxyoctyl)-cyclopent-1β-yl]propionate (VID),
54. racemic methyl 5-[5α-hydroxy-2β-(3-hydroxyoctyl)-cyclopent-1β-yl]pentanoate (VID), 55. racemic methyl 5-[5β-hydroxy-2β-(3-hydroxyoctyl)-cyclopent-1β-yl]pentanoate (VID),
56. racemic methyl 3-methyl-5-[5α-hydroxy-2β-(3-hydroxyoctyl)cyclopent-1β-yl]pentanoate (VID),
57. racemic methyl 3-methyl-5-[5β-hydroxy-2β-(3-hydroxyoctyl)cyclopent-1β-yl]pentanoate (VID),
58. racemic ethyl 7-[5α-hydroxy-2β-(3-hydroxybutyl)-cyclopent-1β-yl]heptanoate (VID),
59. racemic ethyl 7-[5β-hydroxy-2β-(3-hydroxybutyl)-cyclopent-1β-yl]heptanoate (VID),
60. racemic ethyl 7-[5α-hydroxy-2β(3-hydroxy-1-octenyl)-3-cyclopenten-1β-yl]heptanoate (VD),
61. racemic ethyl 7-[5β-hydroxy-2β-(3-hydroxy-1-octenyl)-3-cyclopenten-1β-yl]heptanoate (VD),
62. racemic ethyl 3-[5α-hydroxy-2β-(3-hydroxy-1-octenyl)-3-cyclopenten-1β-yl]propionate (VD),
63. racemic ethyl 3-[5β-hydroxy-2β-(3-hydroxy-1-octenyl)-3-cyclopenten-1β-yl]propionate (VD),
64. racemic methyl 5-[5α-hydroxy-2β-(3-hydroxy-1-octenyl)-3-cyclopenten-1β-yl]pentanoate (VD),
65. racemic methyl 5-[5β-hydroxy-2β-(3-hydroxy-1-octenyl)-3-cyclopenten-1β-yl]pentanoate (VD),
66. racemic methyl 3-methyl-5-[5α-hydroxy-2β-(3-hydroxy-1-octenyl)-3-cyclopenten-1β-yl]pentanoate (VD),
67. racemic methyl 3-methyl-5-[5β-hydroxy-2β-(3-hydroxy-1-octenyl)-3-cyclopenten-1β-yl]pentanoate (VD),
68. racemic ethyl 7-[5α-hydroxy-2β-(3-hydroxy-1-butenyl)-3-cyclopenten-1β-yl]heptanoate (VD),
69. racemic ethyl 7-[5β-hydroxy-2β-(3-hydroxy-1-butenyl)-3-cyclopenten-1β-yl]heptanoate (VD),
70. racemic ethyl 7-[5α-hydroxy2β-(3-hydroxy-1-octenyl)cyclopent-1β-yl]heptanoat (VID),
71. racemic ethyl 7-[5β-hydroxy-2β-(3-hydroxy-1-octenyl)cyclopent-1β-yl]heptanoate (VID),
72. racemic ethyl 3-[5α-hydroxy-2β-(3-hydroxy-1-octenyl)cyclopent-1β-yl]propionate (VID),
73. racemic ethyl 3-[5β-hydroxy-2β-(3-hydroxy-1-octenyl)cyclopent-1β-yl]propionate (VID),
74. racemic methyl 5-[5α-hydroxy-2β-(3-hydroxy-1-octenyl)cyclopent-1β-yl]pentanoate (VID),
75. racemic methyl 5-[5β-hydroxy-2β-(3-hydroxy-1-octenyl)cyclopent-1β-yl]pentanoate (VID),
76. racemic methyl 3-methyl-5-[5α-hydroxy-2β-(3-hydroxy-1-octenyl)cyclopent-1β-yl]pentanoate (VID),
77. racemic methyl 3-methyl-5-[5β-hydroxy-2β-(3-hydroxy-1-octenyl)cyclopent-1β-yl]pentanoate (VID),
78. racemic ethyl 7-[5α-hydroxy-2β-(3-hydroxy-1-butenyl)cyclopent-1β-yl]heptanoate (VID),
79. racemic ethyl 7-[5β-hydroxy-2β-(3-hydroxy-1-butenyl)cyclopent-1β-yl]heptanoate (VID),
80. racemic ethyl 7-[3α-hydroxy-5-oxo-2β-(3-oxooctyl)cyclopentylidene]-3,5-heptadienoate (IIIE),
81. racemic ethyl 3-[3α-hydroxy-5-oxo-2β-(3-oxooctyl-cyclopentylidene]propionate (IIIE),
82. racemic methyl 5-[3α-hydroxy-5-oxo-2β-(3-oxooctyl)cyclopentylidene]-3-pentenoate (IIIE),
83. racemic methyl 3-methyl-5-[3α-hydroxy-5-oxo-2β-(3-oxooctyl)cyclopentylidene]-3pentenoate (IIIE),
84. racemic ethyl 7-[3α-hydroxy-5-oxo-2β-(3-oxobutyl)cyclopentylidene]-3,5-heptadienoate (IIIE),
85. racemic ethyl 7-[3α-hydroxy-5-oxo-2β-(3-oxooctyl)cyclopent-1α-yl]heptanoate (IIID),
86. racemic ethyl 3-[3α-hydroxy-5-oxo-2β-(3-oxooctyl)cyclopent-1α-yl]propionate (IIID),
87. racemic methyl 5-[3α-hydroxy-5-oxo-2β-(3-oxooctyl)cyclopent-1α-yl]pentanoate (IIID),
88. racemic methyl 3-methyl-5-[3α-hydroxy-5-oxo-2β-(3-oxooctyl)cyclopent-1α-yl]pentanoate (IIID),
89. racemic ethyl 7-[3α-hydroxy-5-oxo-2β-(3-oxobutyl)cyclopent-1α-yl]heptanoate (IIID), and the like as starting materials in the procedure of Preparation 32 is productive of the corresponding free acids.

EXAMPLE 20

Racemic methyl 7-[3α-hydroxy-5-oxo-2β-(3-oxooctyl)cyclopent-1β-yl]heptanoate (IVA)

A solution of 0.2 g. of racemic 7-[3α-hydroxy-5-oxo-2β-(3-oxooctyl)cyclopent-1β-yl]-heptanoic acid (IVA) in a mixture of 1 ml. of methanol and 9 ml. of diethyl ether is mixed at room temperature (about 25°C.) with excess diazomethane in diethyl ether and allowed to stand for about 15 minutes. The mixture is then evaporated to dryness under reduced pressure to obtain a residue comprising racemic methyl 7-[3α-hydroxy-5-oxo-2β-(3-oxooctyl)cyclopent-1β-yl]heptanoate (IVA).

Following the procedure of Example 20 but substituting for diazomethane other diazoalkanes, for example diazoethane, diazobutane, 1-diazo-2-ethylhexane, cyclohexyldiazomethane, 1-diazo-2-propene, diazododecane, and the like, gives ethyl, butyl, 2-ethylhexyl, cyclohexylmethyl, allyl, lauryl and the like esters of racemic 7-[3α-hydroxy-5-oxo-2β-(3-oxooctyl)-cyclopent-1β-yl]heptanoic acid (IVA).

Following the procedure of Example 20 but substituting for racemic 7-[3α-hydroxy-5-oxo-2β-(3-oxooctyl)-cyclopent-1β-yl]-heptanoic acid as starting material other free acids of formulas IVA, VA, VIA, IVB, IVC, VC, VIC, IVD, VD, VID, IIIE and IIID, for example the free acids corresponding to the esters named following Example 20, is productive of the methyl esters of these acids. Similarly, substituting other diazoalkanes, for example those named above, for diazomethane is productive of the corresponding alkyl esters of formulas IVA, VA, VIA, IVB, VB, VIB, IVC, VC, VIC, IVD, VD, VID, IIIE and IIID.

EXAMPLE 21

Racemic ethyl 7-[3α-acetoxy-5-oxo-2β-(3-oxooctyl)cyclopent-1β-yl]heptanoate (IVA)

A mixture of 0.2 g. of racemic ethyl 7-[3α-hydroxy-5-oxo-2β-(3-oxooctyl)cyclopent-1β-yl]-heptanoate (IVA), 1 ml. of acetic anhydride and 1 ml. of pyridine is allowed to stand at room temperature for about 16 hrs., then is poured into 50 ml. of ether and washed several times with dilute hydrochloric acid, then with aqueous sodium bicarbonate. The ether solution is dried over sodium sulfate and evaporated under reduced pressure to give a residue comprising racemic ethyl 7-[3α-acetoxy-5-oxo-2β-(3-oxooctyl)cyclopent-1β-yl]heptanoate (IVA). The thus obtained residue is chromatographed over silica gel and eluted with cyclohexane-ethyl acetate mixtures containing increasing proportions of ethyl acetate. Evaporation of the eluates gives fractions comprising essentially pure racemic ethyl 7-[3α-acetoxy-5-oxo-2β-(3-oxooctyl)cyclopent-1β-yl]heptanoate (IVA). The eluate fractions are chosen by thin-layer chromatographic analysis using plates coated with silica gel and developing with 33% ethyl acetate - 67% cyclohexne.

Following the procedure of Example 21 but substituting propionic anhydride, butyric anhydride, acrylic anhydride, crotonic anhydride, cyclohexanecarboxylic anhydride, benzoic anhydride, napthoic anhydride, p-chlorophenoxyacetic anhydride, furoic anhydride, and a luric anhydride, and the like, there is obtained the corresponding racemic ethyl 7-[3α-acyloxy-5-oxo-2β-(3-oxooctyl)cyclopent-1β-yl]heptanoate (IVA).

Following the procedure of Example 21, treating compounds of formulas IVA and IVB wherein Y is hydrogen with an acid anhydride, for example those named above, is productive of the corresponding monoacylate of formulas IVA and IVB.

Following the procedure of Example 21, treating compounds of formulas VC and VIC wherein Y' is hydrogen with an acid anhydride, for example those named above, is productive of the corresponding monoacylates of formulas VC and VIC.

Following the procedure of Example 21, treating compounds of formula IVC wherein Y and Y' are hydrogen with an acid anhydride, for example those named above is productive of the corresponding diacylates of formula IVC.

Following the procedure of Example 21, treating compounds of formulas VD and VID wherein Y' and Y'' are hydrogen with an acid anhydride, for example those named above, is productive of the corresponding diacylates of formulae VD and VID.

Following the procedure of Example 21, treating compounds of formulas IVD wherein Y, Y', and Y'' are hydrogen with an acid anhydride, for example those named above, is productive of the corresponding triacylates of formula IVD.

We claim:

1. A racemic compound of the formula:

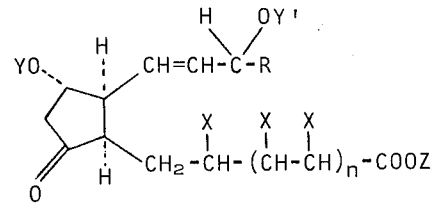

wherein R is an alkyl group containing from one to 8 carbon atoms, inclusive, X is hydrogen or methyl with the proviso that not more than one methyl group can be present in a given side chain, Y and Y' are hydrogen or alkanoyl of one to 12 carbon atoms, inclusive, Z is hydrogen, a hydrocarbyl group of one to 12 carbon atoms, inclusive, or a pharmacologically acceptable cation, and $n$ is 0, 1 or 2.

2. A compound according to claim 1 wherein X, Y, and Y' are hydrogen and $n$ is 2.

3. A compound according to claim 2 wherein R is pentyl.

4. A compound according to claim 3 wherein Z is hydrogen.

5. A compound according to claim 3 wherein Z is ethyl.

* * * * *

UNITED STATES PATENT AND TRADEMARK OFFICE
CERTIFICATE OF CORRECTION

PATENT NO. : 3,984,455
DATED : October 5, 1976
INVENTOR(S) : Philip F. Beal, III, et al.

It is certified that error appears in the above-identified patent and that said Letters Patent are hereby corrected as shown below:

Column 36, line 43: " -5β-alkyl1α,3α,4α,5α- " should read: -- -5β-alkyl-1α,3α,4α,5α- --.
Column 36, line 45: " -alkyl1α,3α,4β,5β- " should read: -- -alkyl-1α,3α4β,5β- --.
Column 37, lines 51-52: "carboxaldehyde, racemic 3α,5α-dihydroxy-2β-(3-oxohexyl)cyclopentane-1β-carboxaldehyde, racemic" should read: -- carboxaldehyde, racemic 3α,5α-dihydroxy-2β-(3-oxopentyl)cyclopentane-1β-carboxaldehyde, racemic 3α,5α-dihydroxy-2β(3-oxohexyl)cyclopentane-1β-carboxaldehyde, racemic --.
Column 47, line 7: "1βyl π-" should read: -- 1β-yl- --.
Column 50, line 41: 4αβ," should read: -- 4aα, --.
Column 52, line 16: "6β-" should read: -- 6α- --.
Column 59, line 58: "2β(3-oxo-" should read: -- 2-(3β-oxo- --.
Column 77, line 5: "cyclohexne" should read: -- cyclohexane --.

Signed and Sealed this

Thirteenth Day of June 1978

[SEAL]

Attest:

RUTH C. MASON
Attesting Officer

DONALD W. BANNER
Commissioner of Patents and Trademarks